US012303362B2

(12) United States Patent
Dean

(10) Patent No.: US 12,303,362 B2
(45) Date of Patent: May 20, 2025

(54) INTERNET OF THINGS (IOT) SOLUTION FOR MANAGEMENT OF URINARY INCONTINENCE

(71) Applicant: DriQ Health, Inc., Philadelphia, PA (US)

(72) Inventor: Gregory Dean, Philadelphia, PA (US)

(73) Assignee: DRIQ HEALTH, INC., Philadelphia, PA (US)

( * ) Notice: Subject to any disclaimer, the term of this patent is extended or adjusted under 35 U.S.C. 154(b) by 871 days.

(21) Appl. No.: 17/436,271

(22) PCT Filed: Mar. 4, 2020

(86) PCT No.: PCT/US2020/021034
§ 371 (c)(1),
(2) Date: Sep. 3, 2021

(87) PCT Pub. No.: WO2020/181010
PCT Pub. Date: Sep. 10, 2020

(65) Prior Publication Data
US 2022/0168154 A1    Jun. 2, 2022

Related U.S. Application Data

(60) Provisional application No. 62/980,416, filed on Feb. 23, 2020, provisional application No. 62/926,054,
(Continued)

(51) Int. Cl.
*A61F 13/42*    (2006.01)
*A61F 13/84*    (2006.01)
*H04W 4/38*    (2018.01)

(52) U.S. Cl.
CPC .............. *A61F 13/42* (2013.01); *A61F 13/84* (2013.01); *H04W 4/38* (2018.02); *A61F 2013/424* (2013.01); *A61F 2013/8479* (2013.01)

(58) Field of Classification Search
CPC ........ A61F 5/4404; A61F 5/443; G01M 3/16; G08B 21/182
See application file for complete search history.

(56) References Cited

U.S. PATENT DOCUMENTS 5,016,645 A * 5/1991 Williams ............. A61N 1/0587
607/129
6,171,289 B1 * 1/2001 Millot ..................... A61F 5/443
604/336

(Continued)

FOREIGN PATENT DOCUMENTS

CN    102222257 A    10/2011
CN    107530214 A    1/2018
(Continued)

OTHER PUBLICATIONS

International Application No. PCT/US2020/021034, International Preliminary Report on Patentability, Mailed On Sep. 16, 2021, 14 pages.
(Continued)

*Primary Examiner* — Guy K Townsend
(74) *Attorney, Agent, or Firm* — Kilpatrick Townsend & Stockton LLP

(57) ABSTRACT

The present disclosure relates to an intelligent internet of things (IoT) monitoring system, and in particular to techniques (e.g., systems, methods, computer program products storing code or instructions executable by one or more processors) for the implementation of an IoT solution to manage urinary incontinence. Some aspects are directed to the concept of a management platform that allows for end users such as health care providers, caretakers, or medical personnel to manage and monitor one or more subjects through one or more client devices using a network of sensors and IoT devices. Other aspects are directed the concept of a data analysis system configured to train and
(Continued)

deploy one or more prediction models for analysis and tracking metrics of health or wellbeing for the one or more subjects.

16 Claims, 32 Drawing Sheets

Related U.S. Application Data filed on Oct. 25, 2019, provisional application No. 62/813,318, filed on Mar. 4, 2019.

(56) References Cited

U.S. PATENT DOCUMENTS

| | | | |
|---|---|---|---|
| 6,685,683 B1* | 2/2004 | Clok | A61L 24/0021 604/344 |
| 7,066,919 B1* | 6/2006 | Sauerland | A61F 5/44 604/327 |
| 7,670,289 B1* | 3/2010 | McCall | A61M 1/3655 210/651 |
| 7,977,529 B2 | 7/2011 | Bergman et al. | |
| 8,398,603 B2* | 3/2013 | Thirstrup | A61B 5/746 602/41 |
| 8,409,158 B2* | 4/2013 | Edvardsen | A61F 5/443 604/335 |
| 8,821,464 B2* | 9/2014 | Hanuka | A61F 5/441 604/333 |
| 9,066,812 B2* | 6/2015 | Edvardsen | A61F 5/443 |
| 9,107,776 B2 | 8/2015 | Bergman et al. | |
| 9,216,104 B2* | 12/2015 | Thirstrup | A61F 5/4404 |
| 9,308,332 B2* | 4/2016 | Heppe | A61M 1/30 |
| 9,322,797 B1* | 4/2016 | Lastinger | G01N 27/12 |
| 9,629,964 B2* | 4/2017 | Wuepper | G01M 3/16 |
| 9,867,934 B2* | 1/2018 | Heppe | A61M 1/3656 |
| 9,928,341 B2* | 3/2018 | Angelides | G16H 40/67 |
| 10,016,298 B2* | 7/2018 | Thirstrup | A61F 13/42 |
| 10,251,793 B1 | 4/2019 | Li | |
| 10,500,084 B2* | 12/2019 | Hansen | A61B 5/7405 |
| 10,531,977 B2* | 1/2020 | Schoess | A61F 5/445 |
| 10,792,184 B2* | 10/2020 | Hvid | A61M 3/0216 |
| 10,799,385 B2* | 10/2020 | Hansen | G01M 3/40 |
| 10,849,781 B2* | 12/2020 | Hansen | G01N 27/041 |
| 10,874,541 B2* | 12/2020 | Seres | G01K 3/10 |
| 10,987,243 B2* | 4/2021 | Thirstrup | A61B 5/746 |
| 11,096,818 B2* | 8/2021 | Thirstrup | A61F 13/02 |
| 11,135,084 B2* | 10/2021 | Seres | A61F 5/443 |
| 11,406,525 B2* | 8/2022 | Seres | A61B 5/4848 |
| 11,471,318 B2* | 10/2022 | Hansen | A61F 5/448 |
| 11,491,042 B2* | 11/2022 | Seres | G01F 23/261 |
| 11,517,469 B2* | 12/2022 | Hansen | A61F 5/445 |
| 11,529,253 B2* | 12/2022 | Hansen | A61F 5/4404 |
| 11,534,323 B2* | 12/2022 | Hansen | A61F 2/64 |
| 11,540,937 B2* | 1/2023 | Hansen | A61F 5/445 |
| 11,547,595 B2* | 1/2023 | Hansen | A61F 5/44 |
| 11,547,596 B2* | 1/2023 | Hansen | A61F 5/44 |
| 11,559,423 B2* | 1/2023 | Speiermann | A61F 5/445 |
| 11,559,426 B2* | 1/2023 | Sletten | A61F 5/44 |
| 11,589,811 B2* | 2/2023 | Hansen | A61F 5/4404 |
| 11,590,015 B2* | 2/2023 | Hansen | A61F 13/15577 |
| 11,607,334 B2* | 3/2023 | Hansen | A61F 5/44 |
| 11,612,508 B2* | 3/2023 | Hansen | A61F 5/445 604/336 |
| 11,612,509 B2* | 3/2023 | Hansen | A61F 5/443 604/344 |
| 11,612,512 B2* | 3/2023 | Hansen | A61B 5/4851 604/332 |
| 11,622,719 B2* | 4/2023 | Hansen | A61B 5/0002 600/301 |
| 11,627,891 B2* | 4/2023 | Hansen | G06T 7/74 382/128 |
| 11,628,084 B2* | 4/2023 | Hansen | A61F 5/443 604/344 |
| 11,654,043 B2* | 5/2023 | Hansen | A61F 5/445 604/344 |
| 11,679,021 B2* | 6/2023 | Hansen | A61F 5/445 604/344 |
| 11,701,248 B2* | 7/2023 | Hansen | A61F 5/4404 604/318 |
| 11,730,622 B2* | 8/2023 | Hansen | A61F 5/4404 604/336 |
| 11,737,907 B2* | 8/2023 | Hansen | A61F 5/443 604/332 |
| 11,896,512 B2* | 2/2024 | Liddle | A61F 5/445 |
| 2002/0145525 A1 | 10/2002 | Friedman et al. | |
| 2004/0078219 A1* | 4/2004 | Kaylor | G16H 40/67 600/300 |
| 2004/0100376 A1* | 5/2004 | Lye | A61B 5/411 600/300 |
| 2005/0032525 A1 | 2/2005 | Gasbarro | |
| 2005/0101841 A9* | 5/2005 | Kaylor | G16H 40/67 600/300 |
| 2006/0194324 A1* | 8/2006 | Faries | A61B 46/10 436/1 |
| 2007/0049883 A1* | 3/2007 | Ales, III | A61F 13/42 604/361 |
| 2007/0270774 A1* | 11/2007 | Bergman | G16H 40/60 604/361 |
| 2008/0275327 A1* | 11/2008 | Faarbaek | A61B 5/6833 600/382 |
| 2009/0105785 A1* | 4/2009 | Wei | A61N 1/36132 600/301 |
| 2010/0030167 A1* | 2/2010 | Thirstrup | A61F 5/4404 340/657 |
| 2012/0143154 A1* | 6/2012 | Edvardsen | A61F 5/4404 604/336 |
| 2012/0143155 A1* | 6/2012 | Edvardsen | A61F 5/443 604/318 |
| 2012/0268278 A1* | 10/2012 | Lewis | A61B 5/002 340/573.5 |
| 2013/0036802 A1* | 2/2013 | Johnson | A61F 13/42 73/74 |
| 2013/0060213 A1* | 3/2013 | Hanuka | A61F 5/441 604/344 |
| 2013/0231620 A1* | 9/2013 | Thirstrup | A61F 5/445 604/344 |
| 2014/0200538 A1* | 7/2014 | Euliano | A61F 13/42 604/361 |
| 2015/0250639 A1* | 9/2015 | Thirstrup | A61F 13/00051 156/278 |
| 2015/0257923 A1* | 9/2015 | Thirstrup | A61F 13/42 604/318 |
| 2015/0352357 A1* | 12/2015 | Wei | A61N 1/36007 604/385.03 |
| 2016/0220164 A1 | 8/2016 | Lewis et al. | |
| 2017/0140103 A1* | 5/2017 | Angelides | A61F 5/4404 |
| 2017/0224253 A1* | 8/2017 | Berlin | G08B 21/22 |
| 2017/0340474 A1* | 11/2017 | Thirstrup | A61B 5/746 |
| 2017/0348137 A1* | 12/2017 | Hvid | A61M 3/0295 |
| 2017/0360592 A1* | 12/2017 | Carrubba | A61F 5/445 |
| 2018/0021184 A1* | 1/2018 | Monson | H01Q 9/0457 340/573.5 |
| 2018/0116878 A1* | 5/2018 | MacNaughton | G08B 21/20 |
| 2018/0325744 A1* | 11/2018 | Weidman | A61F 13/51498 |
| 2019/0133810 A1* | 5/2019 | Seres | A61B 5/445 |
| 2019/0133811 A1* | 5/2019 | Seres | A61F 5/4404 |
| 2019/0133812 A1* | 5/2019 | Seres | A61F 5/443 |
| 2019/0142623 A1* | 5/2019 | Schoess | A61F 5/443 604/336 |
| 2019/0192332 A1* | 6/2019 | Hansen | A61B 5/742 |
| 2019/0192333 A1* | 6/2019 | Hansen | A61B 5/6833 |
| 2019/0192334 A1* | 6/2019 | Hansen | A61F 5/445 |
| 2019/0374372 A1* | 12/2019 | Seres | A61B 5/6802 |
| 2020/0100931 A1* | 4/2020 | Schoess | A61F 5/445 |
| 2020/0188161 A1* | 6/2020 | Seres | G01K 13/00 |
| 2020/0246174 A1* | 8/2020 | Hansen | A61F 5/443 |
| 2020/0246175 A1* | 8/2020 | Hansen | G01M 3/16 |
| 2020/0246176 A1* | 8/2020 | Hansen | A61F 5/445 |
| 2020/0246177 A1* | 8/2020 | Hansen | A61F 5/445 |
| 2020/0306074 A1* | 10/2020 | Speiermann | A61F 5/4404 |

(56) References Cited

U.S. PATENT DOCUMENTS

| | | | | |
|---|---|---|---|---|
| 2020/0330258 A1* | 10/2020 | Hansen | .................... | A61F 5/44 |
| 2020/0330260 A1* | 10/2020 | Hansen | .................. | G16H 50/30 |
| 2020/0337880 A1* | 10/2020 | Hansen | .................. | A61F 5/443 |
| 2020/0337881 A1* | 10/2020 | Hansen | .................. | A61F 5/4404 |
| 2020/0337882 A1* | 10/2020 | Hansen | ................ | A61F 5/4404 |
| 2020/0337883 A1* | 10/2020 | Hansen | ................ | A61F 5/4404 |
| 2020/0375499 A1* | 12/2020 | Hansen | ................ | A61B 5/4216 |
| 2020/0375782 A1* | 12/2020 | Hansen | .................. | G01M 3/40 |
| 2020/0375783 A1* | 12/2020 | Hansen | ........... | H04M 1/724094 |
| 2020/0375784 A1* | 12/2020 | Hansen | .................. | A61F 5/443 |
| 2020/0375785 A1* | 12/2020 | Hansen | .................. | G16H 30/40 |
| 2020/0375786 A1* | 12/2020 | Hansen | .................. | A61F 5/443 |
| 2020/0383637 A1* | 12/2020 | Hansen | ................ | A61B 5/7405 |
| 2020/0383818 A1* | 12/2020 | Hansen | .................... | A61F 5/44 |
| 2020/0383819 A1* | 12/2020 | Sletten | .................... | A61F 5/44 |
| 2020/0383820 A1* | 12/2020 | Hansen | .................. | G16H 40/40 |
| 2020/0383821 A1* | 12/2020 | Hansen | .................... | A61F 5/44 |
| 2020/0390587 A1* | 12/2020 | Svanegaard | ........... | G16H 40/40 |
| 2020/0390588 A1* | 12/2020 | Hansen | ................ | A61F 5/4404 |
| 2020/0390589 A1* | 12/2020 | Hansen | ................ | A61F 5/4404 |
| 2020/0395120 A1* | 12/2020 | Svanegaard | .......... | G06F 3/0482 |
| 2020/0405229 A1* | 12/2020 | Svanegaard | .......... | A61B 5/4851 |
| 2020/0405230 A1* | 12/2020 | Svanegaard | .......... | A61B 5/6813 |
| 2021/0000635 A1* | 1/2021 | Hansen | .................. | A61F 5/443 |
| 2021/0015654 A1* | 1/2021 | Hansen | .................. | A61F 5/443 |
| 2021/0085511 A1* | 3/2021 | Hansen | .................. | A61F 5/445 |
| 2021/0085512 A1* | 3/2021 | Hansen | .................. | A61B 5/0002 |
| 2021/0361464 A1* | 11/2021 | Larsen | .................... | A61F 5/443 |
| 2021/0361466 A1* | 11/2021 | Hansen | ................ | A61F 5/4404 |
| 2021/0361467 A1* | 11/2021 | Hansen | ................ | A61F 5/4404 |
| 2021/0369197 A1* | 12/2021 | Hansen | ................ | A61B 5/7435 |
| 2021/0369488 A1* | 12/2021 | Hansen | ................ | A61F 5/4404 |
| 2021/0369489 A1* | 12/2021 | Hansen | .................. | A61F 5/443 |
| 2021/0369490 A1* | 12/2021 | Hansen | ................ | A61F 5/4404 |
| 2022/0000652 A1* | 1/2022 | Thirstrup | ................ | A61F 5/443 |
| 2022/0378602 A1* | 12/2022 | Hansen | ................ | A61F 5/4404 |
| 2023/0059470 A1* | 2/2023 | Hansen | .................. | A61F 5/443 |
| 2023/0064734 A1* | 3/2023 | Hansen | .................. | A61F 5/443 |
| 2023/0105402 A1* | 4/2023 | Hansen | .................. | A61F 5/448 |
| | | | | 604/344 |
| 2023/0117727 A1* | 4/2023 | Hansen | .................... | G06T 7/70 |
| | | | | 604/327 |
| 2023/0118594 A1* | 4/2023 | Speiermann | ..... | A61B 5/150809 |
| | | | | 604/318 |
| 2023/0190509 A1* | 6/2023 | Hansen | .................. | A61F 5/443 |
| | | | | 604/336 |
| 2023/0233357 A1* | 7/2023 | Hansen | ................ | A61B 5/4255 |
| | | | | 604/332 |
| 2023/0293335 A1* | 9/2023 | Hansen | .................. | A61F 5/443 |
| | | | | 604/344 |

FOREIGN PATENT DOCUMENTS

| | | |
|---|---|---|
| JP | 2015128477 A | 7/2015 |
| WO | 2011054045 A1 | 5/2011 |
| WO | 2016090492 A1 | 6/2016 |
| WO | 2016187568 A1 | 11/2016 |
| WO | 2018098300 | 5/2018 |
| WO | WO-2018098300 A1 * 5/2018 ........... A61B 5/0022 |

OTHER PUBLICATIONS

International Application No. PCT/US2020/021034, "Invitation to Pay Additional Fees and, Where Applicable, Protest Fee", May 7, 2020, 4 pages.

International Application No. PCT/US2020/050025, International Search Report and Written Opinion, Mailed On Feb. 2, 2021, 10 pages.

International Application No. PCT/US2020/050025, "Invitation to Pay Additional Fees And, Where Applicable, Protest Fee", Nov. 17, 2020, 2 pages.

International Application No. PCT/US2020/021034, International Search Report and Written Opinion, Mailed On Jul. 24, 2020, 19 pages.

European Application No. EP20766887.2, Extended European Search Report, Mailed On Nov. 17, 2022, 6 pages.

Chinese Application No. CN202080087414.6, Office Action, Mailed On Jan. 4, 2023, 14 pages.

Singapore Application No. SG11202109681V, Written Opinion, Mailed On Feb. 3, 2023, 10 pages.

* cited by examiner

INTERNET OF THINGS (IOT) SOLUTION FOR MANAGEMENT OF URINARY INCONTINENCE

CROSS-REFERENCE TO RELATED APPLICATIONS

The present application is a U.S. National Stage of International Application No. PCT/US2020/021034, filed Mar. 4, 2020, entitled, "INTERNET OF THINGS (IOT) SOLUTION FOR MANAGEMENT OF URINARY INCONTINENCE," which claims the benefit of priority to U.S. Provisional Application No. 62/980,416, filed Feb. 23, 2020, entitled "INTERNET OF THINGS (IOT) SOLUTION FOR MANAGEMENT OF URINARY INCONTINENCE," U.S. Provisional Application No. 62/926,054, filed Oct. 25, 2019, entitled "REMOTE VOLUME MEASUREMENT USING A PASSIVE LINEAR RFID TAG ARRAY IN CONJUNCTION WITH A UHF RFID TRANSCEIVER AND IoT GATEWAY" and U.S. Provisional Application No. 62/813,318, filed Mar. 4, 2019, entitled "INTERNET OF THINGS ENABLED BED-WETTING AND MOBILITY ALARM," the entire contents of which are incorporated herein by reference for all purposes.

FIELD

The present disclosure relates to an intelligent internet of things (IoT) monitoring system, and in particular to techniques (e.g., systems, methods, computer program products storing code or instructions executable by one or more processors) for the implementation of an IoT solution to manage urinary incontinence.

BACKGROUND

Urinary incontinence can be defined in general as the loss of bladder control and resulting involuntary leakage of urine. Numerous physical disorders contribute to urinary incontinence including urologic, gynecologic, and neurologic disorders, and functional impairments such as dementia and lack of mobility (including bed restraints). In particular, there are several different types of urinary incontinence including urge, stress, mixed, overflow, and functional incontinence. Urge incontinence is involuntary leakage accompanied or immediately proceeded by urgency, and indicates detrusor overactivity. Stress incontinence is involuntary leakage from effort or exertion, or from sneezing or coughing, and is usually related to increased urethral mobility, poor intrinsic sphincter function, or weak pelvic floor muscles. Mixed incontinence is the combination of urge and stress incontinence. Overflow incontinence is associated with overdistention of the bladder caused by obstruction (e.g., enlarged prostate) or a neurological condition (e.g., spinal cord injury). Functional incontinence is leakage in the presence of an intact lower urinary tract system and is due to functional limitations such as decreased mobility, cognitive impairment, or dressing apraxia.

Urinary incontinence is commonly encountered in nursing home residents (e.g., affecting over 50% of nursing home residents), and is associated with significant morbidity and utilization of health care resources. Nursing home residents typically suffer from a variety of conditions including chronic disease, cognitive impairment, and functional limitations. Although the etiology of urinary incontinence in long-term care residents is usually multifactorial, dementia and functional impairments including immobility are the primary risk factors. Immobility increases the likelihood of incontinence among nursing home residents by preventing them from getting to the toilet; whereas dementia reduces their motivation to do so. Other potentially modifiable risk factors include poor pelvic floor muscle contraction, constipation, poorly controlled diabetes, delirium, systolic hypertension, parkinsonism, arthritis, back problems, hearing and visual impairment, recurrent urinary tract infections, medications (e.g., benzodiazepines, tranquilizers, antidepressants, hypnotics, and diuretics), high caffeine intake, smoking, and obesity.

Urinary incontinence management typically focuses on identifying and treating underlying causes, such as detrusor instability, urinary tract infections, diet- or medication-induced diarrhea, constipation and fecal impaction. Despite appropriate management, residents may remain incontinent because of dementia and health or restraint-related immobility. Typically nursing homes lack the staff and financial resources to provide residents with sufficiently frequent toileting assistance (including prompted voiding). Use of special undergarments and absorbent pads is the usual practice for urinary incontinence management. Practice guidelines specify that a resident's soiled garments should be changed and skin cleansed in a timely fashion. However, little data exists describing the amount of time required to implement incontinence management activities, and there is even less data about how better skin cleansing might improve outcomes. Nonetheless, skin exposure to urine due to infrequent resident undergarment and absorbent pad changes can produce a significant increase in skin wetness, with increased rubbing and abrasion, predisposing the perineal area to skin irritation and impairing the healing process of pressure ulcers. Accordingly, the need exists for improved techniques to manage urinary incontinence.

SUMMARY

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a method including: obtaining, by a data processing system, input data; parsing, by the data processing system, the input data to identify sensor data from a sensor; and comparing, by the data processing system, a first energy level and a second energy level from the sensor data to one or more energy levels associated with a dry or normalized condition for an environment in which the sensor is deployed, where the first energy level is obtained at a first time and the second energy level is obtained at a second time that is after the first time. The method also includes determining, by the data processing system, the first energy level is associated with the dry or normalized condition based on the comparison; determining, by the data processing system, the second energy level is associated with a moisture event based on the comparison; and in response to determining the second energy level is associated with a moisture event, determining, by the data processing system, a subject associated with the sensor has had an incontinence event. The method also includes determining, by the data processing system, the sensor data does not include a third energy level within a predefined period of time after receipt of the second energy level at the second time; in response to determining the sensor data does not include the third energy level, determining, by the data processing system, a undergarment or absorbent pad associated with the subject has become saturated; and providing, by the data processing system, a user interface displaying information concerning the incontinence event and the undergarment or absorbent pad associated with the subject has become saturated. Other embodiments of this aspect include corresponding computer systems, apparatus, and computer programs recorded on one or more computer storage devices, each configured to perform the actions of the methods.

Implementations may include one or more of the following features. The method where the parsing includes grouping the sensor data from the sensor over a window of time based on a unique identifier associated with the sensor. The method where the determining the second energy level is associated with the moisture event includes determining a change between the first energy level and the second energy level exceeds a predetermined energy threshold associated with the moisture event or the second energy level exceeds a predetermined energy threshold associated with the moisture event. The method where the first energy level is a first impedance value and the second energy level is a second impedance value different from the first impedance value. Implementations of the described techniques may include hardware, a method or process, or computer software on a computer-accessible medium.

One general aspect includes a method including: obtaining, by a data processing system, input data; parsing, by the data processing system, the input data to identify sensor data from a sensor; and comparing, by the data processing system, a first energy level and a second energy level from the sensor data to one or more energy levels associated with a dry or normalized condition for an environment in which the sensor is deployed, where the first energy level is obtained at a first time and the second energy level is obtained at a second time that is after the first time. The method also includes determining, by the data processing system, the first energy level is associated with the dry or normalized condition based on the comparison of the first energy level to the second energy level; determining, by the data processing system, the second energy level is associated with a moisture event based on the comparison; and in response to determining the second energy level is associated with a moisture event, determining, by the data processing system, a subject associated with the sensor has had an incontinence event. The method also includes determining, by the data processing system, the sensor data includes a third energy level within a predefined period of time after receipt of the second energy level at the second time; and in response to determining the sensor data does include the third energy level, comparing, by the data processing system, the third energy level to the second energy level. The method also includes determining, by the data processing system, the third energy level is associated with a drying event based on the comparison of the third energy level to the second energy level; in response to determining the third energy level is associated with a drying event, determining, by the data processing system, a undergarment or absorbent pad associated with the subject is unsaturated; and providing, by the data processing system, a user interface displaying information concerning the incontinence event and the undergarment or absorbent pad associated with the subject is unsaturated. Other embodiments of this aspect include corresponding computer systems, apparatus, and computer programs recorded on one or more computer storage devices, each configured to perform the actions of the methods.

Implementations may include one or more of the following features. The method where the parsing includes grouping the sensor data from the sensor over a window of time based on a unique identifier associated with the sensor. The method where the determining the second energy level is associated with the moisture event includes determining a change between the first energy level and the second energy level exceeds a predetermined energy threshold associated with the moisture event or the second energy level exceeds a predetermined energy threshold associated with the moisture event. The method where the determining the third energy level is associated with a drying event includes determining a change between the second energy level and the third energy level exceeds a predetermined drying threshold associated with a drying event or the third energy level exceeds a predetermined drying threshold associated with a drying event. The method where the first energy level is a first impedance value and the second energy level is a second impedance value different from the first impedance value, and the third energy level is a third impedance value different from the first impedance value and the second impedance value. Implementations of the described techniques may include hardware, a method or process, or computer software on a computer-accessible medium.

One general aspect includes a method including: obtaining, by a data processing system, input data; parsing, by the data processing system, the input data to identify sensor data from a sensor; and comparing, by the data processing system, a first energy level and a second energy level from the sensor data to one or more energy levels associated with a stationary position, where the first energy level is obtained at a first time and the second energy level is obtained at a second time that is after the first time. The method also includes determining, by the data processing system, the first energy level is associated with the stationary position based on the comparison. The method also includes determining, by the data processing system, the second energy level is associated with a motion event based on the comparison. The method also includes in response to determining the second energy level is associated with a motion event, determining, by the data processing system, a subject associated with the sensor has moved; and determining, by the data processing system, the sensor data includes a third energy level within a predefined period of time after receipt of the second energy level at the second time. The method also includes in response to determining the sensor data includes the third energy level, determining, by the data processing system, the third energy level is different from the second energy level and the third energy level exceeds a predetermined activity threshold associated with an activity. The method also includes predicting, by a prediction model of the data processing system, the activity is a subject rolling over in bed or getting out of bed based on a pattern of the sensor data, the determination of the motion event, and the determination that the third energy level is different from the second energy level and the third energy level exceeds the predetermined activity threshold. The method also includes recording, by the data processing system, the prediction that the subject has rolled over in bed or gotten out of bed. Other embodiments of this aspect include corresponding computer systems, apparatus, and computer programs recorded on one or more computer storage devices, each configured to perform the actions of the methods.

Implementations may include one or more of the following features. The method where the parsing includes grouping the sensor data from the sensor over a window of time based on a unique identifier associated with the sensor. The method where the determining the second energy level is associated with the motion event includes determining a change between the first energy level and the second energy level exceeds a predetermined energy threshold associated with the motion event or the second energy level exceeds a predetermined energy threshold associated with the motion event. The method where the first energy level is a first impedance value and the second energy level is a second impedance value different from the first impedance value, and the third energy level is a third impedance value different from the first impedance value and the second impedance value. Implementations of the described techniques may include hardware, a method or process, or computer software on a computer-accessible medium.

One general aspect includes an absorbent article including: a liquid permeable top sheet. The absorbent article also includes an absorbent material disposed under the liquid permeable top sheet. The absorbent article also includes a nonabsorbent material disposed adjacent to at least a portion of the liquid permeable top sheet or the absorbent material. The absorbent article also includes a liquid impermeable back sheet disposed over the absorbent material such that the absorbent material is disposed between the liquid permeable top sheet and the liquid impermeable back sheet. The absorbent article also includes one or more attachment structures attached to the liquid impermeable back sheet, where the one or more attachment structures are structured to hold one or more sensors.

Implementations may include one or more of the following features. The absorbent article where the one or more attachment structures are one or more sleeve structures. The absorbent article where a first attachment structure of the one or more attachment structures is attached to the liquid impermeable back sheet on an anterior side of the liquid impermeable back sheet over an interface between the underlying absorbent material and the nonabsorbent material. The absorbent article where a second attachment structure of the one or more attachment structures is attached to the liquid impermeable back sheet over an outer margin of the nonabsorbent material. The absorbent article where a fourth attachment structure of the one or more attachment structures is attached to the liquid impermeable back sheet on a posterior side of the liquid impermeable back sheet over an interface between the underlying absorbent material and the nonabsorbent material. The absorbent article where a third attachment structure of the one or more attachment structures is attached to the liquid impermeable back sheet on an anterior side of the liquid impermeable back sheet over the underlying absorbent material. The absorbent article where the one or more attachment structures are a magnetic structure. The absorbent article further including the one or more sensors, where each sensor of the one or more sensors is disposed in a respective attachment structure of the one or more attachment structures. The absorbent article where the one or more sensors are one or more radio frequency identification (RFID) sensors.

One general aspect includes an absorbent article including: a liquid permeable top sheet. The absorbent article also includes an absorbent material disposed under the liquid permeable top sheet. The absorbent article also includes a nonabsorbent material disposed adjacent to at least a portion of the liquid permeable top sheet or the absorbent material. The absorbent article also includes a liquid impermeable back sheet disposed over the absorbent material such that the absorbent material is disposed between the liquid permeable top sheet and the liquid impermeable back sheet. The absorbent article also includes one or more sensors attached to the liquid impermeable back sheet.

Implementations may include one or more of the following features. The absorbent article where the one or more sensors are one or more radio frequency identification (RFID) sensors. The absorbent article where a first sensor of the one or more sensors is attached to the liquid impermeable back sheet on an anterior side of the liquid impermeable back sheet over an interface between the underlying absorbent material and the nonabsorbent material. The absorbent article where a second sensor of the one or more sensors is attached to the liquid impermeable back sheet over an outer margin of the nonabsorbent material. The absorbent article where a third sensor of the one or more sensors is attached to the liquid impermeable back sheet on an anterior side of the liquid impermeable back sheet over the underlying absorbent material. The absorbent article where a fourth sensor of the one or more sensors is attached to the liquid impermeable back sheet on a posterior side of the liquid impermeable back sheet over an interface between the underlying absorbent material and the nonabsorbent material.

One general aspect includes a system including: an absorbent article including: a liquid permeable top sheet, an absorbent material disposed under the liquid permeable top sheet, a nonabsorbent material disposed adjacent to at least a portion of the liquid permeable top sheet or the absorbent material, a liquid impermeable back sheet disposed over the absorbent material such that the absorbent material is disposed between the liquid permeable top sheet and the liquid impermeable back sheet, and one or more sensors attached to the liquid impermeable back sheet. The system also includes an internet of things (IoT) device in wireless communication with the one or more sensors.

Implementations may include one or more of the following features. The system where the one or more sensors are one or more radio frequency identification (RFID) sensors. The system where the IoT device includes a RFID reader and a controller. The system where a first sensor of the one or more sensors is attached to the liquid impermeable back sheet on an anterior side of the liquid impermeable back sheet over an interface between the underlying absorbent material and the nonabsorbent material. The system where a second sensor of the one or more sensors is attached to the liquid impermeable back sheet over an outer margin of the nonabsorbent material. The system where a third sensor of the one or more sensors is attached to the liquid impermeable back sheet on an anterior side of the liquid impermeable back sheet over the underlying absorbent material. The system where a fourth sensor of the one or more sensors is attached to the liquid impermeable back sheet on a posterior side of the liquid impermeable back sheet over an interface between the underlying absorbent material and the nonabsorbent material. The system further including an angled bracket including a first end attached to the IoT device and a second end attached to an external antenna connected to the IoT device.

One general aspect includes a measurement system including: a container. The measurement system also includes a linear array of sensors attached to the container, where each sensor of the array of sensors is positioned on the container relative to a respective liquid volume indictor. The measurement system also includes a computing device including a processor and a memory storage device, where a data table is stored in the memory storage device and the table includes a unique identifier for each sensor of the array of sensors and a respective liquid volume indexed with the unique identifier.

One general aspect includes a method including: (i) obtaining, by a data processing system, input data. The method also includes (ii) parsing, by the data processing system, the input data to identify all sensor data collected by an internet of things (IoT) device from a plurality of sensors disposed on a collection device, where the parsing includes grouping the sensor data into subsets of sensor data received from each sensor of the plurality of sensors over the window of time based on a unique identifier associated with each of the sensors, and where at least one subset of sensor data received from a sensor of the plurality of sensors includes a first energy level obtained at a first time and a second energy level obtained at a second time that is after or later than the first time. The method also includes (iii) comparing, by the data processing system, a first energy level and a second energy level from the sensor data to one or more energy levels associated with a dry or normalized condition for an environment in which the plurality of sensors are deployed. The method also includes (iv) determining, by the data processing system, the first energy level is associated with the dry or normalized condition based on the comparison. The method also includes (v) determining, by the data processing system, the second energy level is associated with a moisture event based on the comparison. The method also includes (vi) in response to determining the second energy level is associated with a moisture event, identifying, by the data processing system, a liquid volume associated with the sensor that is associated with the at least one subset of sensor data. The method also includes repeating, by the data processing system, steps (iii)-(vi) for all other subsets of sensor data associated with other sensors of the plurality of sensors to identify additional liquid volumes associated with the other sensors. The method also includes analyzing, by the data processing system, the liquid volume associated with the sensor and the additional liquid volumes associated with the other sensors to determine a total liquid volume of the collection device. The method also includes providing, by the data processing system, a user interface displaying the total liquid volume of the collection device. Other embodiments of this aspect include corresponding computer systems, apparatus, and computer programs recorded on one or more computer storage devices, each configured to perform the actions of the methods.

One general aspect includes a method including: obtaining, by a data processing system, sensor data from a plurality of radio frequency identification (RFID) sensors associated with a subject. The method also includes determining, by the data processing system using the sensor data, a plurality of incontinent events over a period of time. The method also includes determining, by the data processing system using the determined plurality of incontinent events, a mean intervoiding interval for the subject. The method also includes determining, by the data processing system, a statistical aberration in the determined plurality of incontinent events based on the mean intervoiding interval. The method also includes predicting, by a prediction model, a risk of a subject having or developing a urinary tract infection based on the sensor data and the statistical aberration. The method also includes providing, by the data processing system, a user interface displaying information concerning the predicted risk of the subject having or developing the urinary tract infection. Other embodiments of this aspect include corresponding computer systems, apparatus, and computer programs recorded on one or more computer storage devices, each configured to perform the actions of the methods.

Implementations may include one or more of the following features. The method further including: in response to determining the statistical aberration, triggering, by the data processing system, a request for a urinalysis and urine culture to be performed for the subject. The method further including obtaining, by the data processing system, results of the urinalysis and urine culture, where the predicting the risk of the subject having or developing the urinary tract infection is based on the sensor data, the statistical aberration, and the results of the urinalysis and urine culture. The method further including obtaining, by the data processing system, additional data including time interval of meals, iv rates, g tube feed rates, or a combination thereof, where the predicting the risk of the subject having or developing the urinary tract infection is based on the sensor data, the statistical aberration, the results of the urinalysis and urine culture, and the additional data. Implementations of the described techniques may include hardware, a method or process, or computer software on a computer-accessible medium.

One general aspect includes a method including: obtaining, by a data processing system, sensor data from a plurality of radio frequency identification (RFID) sensors associated with a subject. The method also includes determining, by the data processing system using the sensor data, a plurality of motion events over a period of time. The method also includes determining, by a first prediction model, using the determined plurality of motion events, a pattern of motion activity. The method also includes predicting, by a second prediction model, a risk of a subject having or developing a decubitus based on the sensor data and the pattern of motion activity. The method also includes providing, by the data processing system, a user interface displaying information concerning the predicted risk of the subject having or developing the decubitus. Other embodiments of this aspect include corresponding computer systems, apparatus, and computer programs recorded on one or more computer storage devices, each configured to perform the actions of the methods.

Implementations may include one or more of the following features. The method further including obtaining, by the data processing system, additional data including frequency of staff engagement with the subject, where the predicting the risk of the subject having or developing the decubitus is based on the sensor data, the pattern of motion activity, and the additional data. Implementations of the described techniques may include hardware, a method or process, or computer software on a computer-accessible medium.

In some embodiments, a system is provided that includes one or more data processors and a non-transitory computer readable storage medium containing instructions which, when executed on the one or more data processors, cause the one or more data processors to perform part or all of one or more methods disclosed herein.

In some embodiments, a computer-program product is provided that is tangibly embodied in a non-transitory machine-readable storage medium and that includes instructions configured to cause one or more data processors to perform part or all of one or more methods disclosed herein.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

DETAILED DESCRIPTION

I. Introduction

Figure 1:
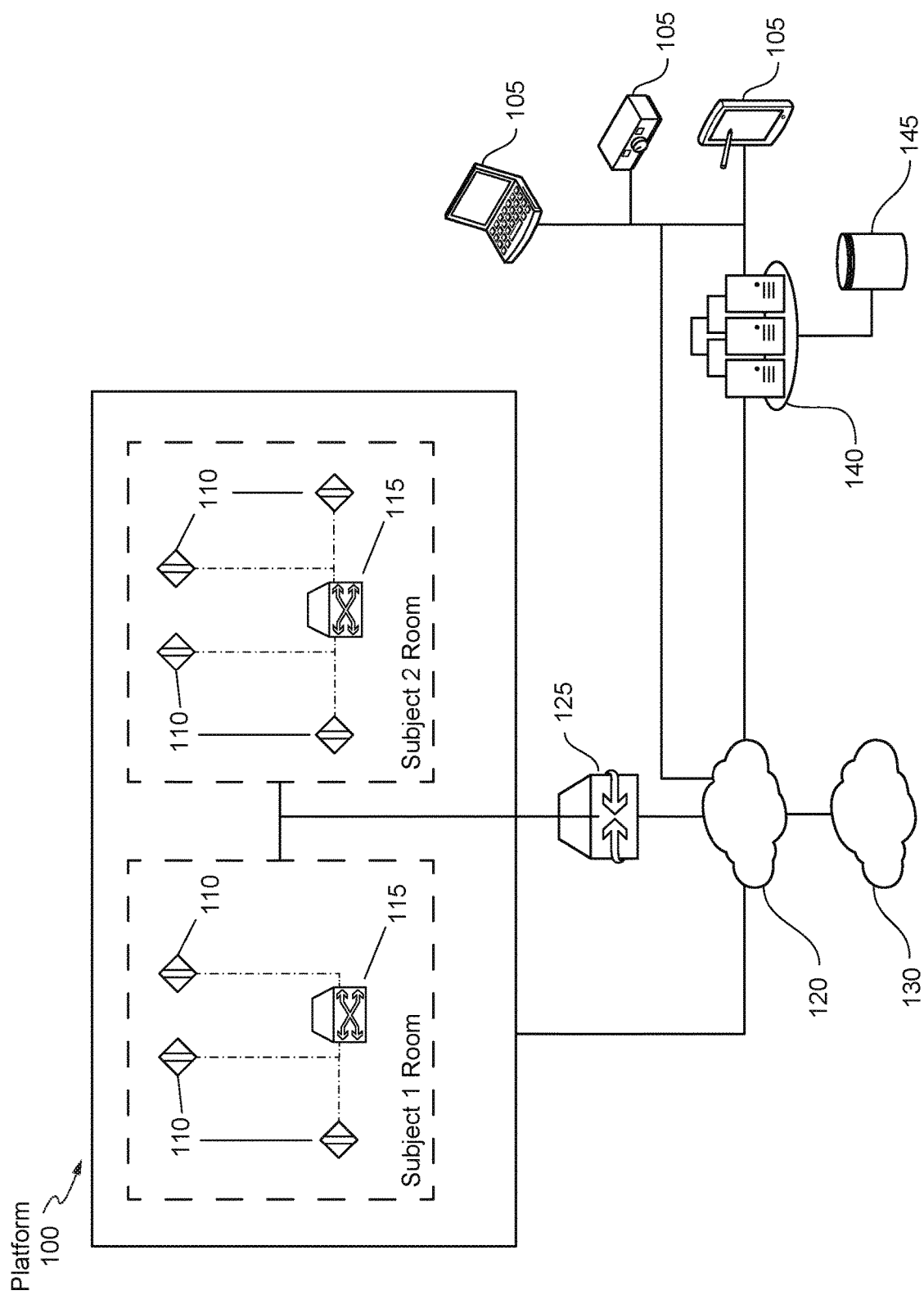
FIG. 1 shows a management platform in accordance with various embodiments.

The present disclosure relates to an IoT monitoring system, and in particular to techniques (e.g., systems, methods, computer program products storing code or instructions executable by one or more processors) for the implementation of an IoT solution to manage urinary incontinence. More specifically, some embodiments of the present disclosure provide a centralized computation and storage system that receives data from various electronic devices (e.g., humidity sensors, temperature sensors, etc.) for analysis of urinary incontinence, voiding patterns, movement of subjects (e.g., movement of subjects in bed to mitigate decubitus or movement of a subject from bed for potential fall analysis), logistic purposes for personnel (e.g., health care providers) management and inventory management, and medical device management (e.g., Foley bag care).

Conventional incontinence monitoring systems typically have a sensor that can detect liquid and stool events, transfer the sensed data for the liquid and stool events to a computing device (e.g., a server), and the computing device processes the transferred data into actionable information (e.g., informs health care providers when a resident needs to be changed), storing the transferred data in a secure server environment. The sensor is typically incorporated into a undergarment or absorbent pad used by a subject (e.g. a patient or nursing home resident), and the receiver is typically located remotely from the subjects' environment in a location occupied by a health care provider. From there, the sensor captures moisture data and, in some cases, geolocation data, and transfers representative data to the receiver, at which point the data is analyzed for actionable information. In this way, the health care provider can use the system to monitor the moisture and location of a subject. In some instances, the incontinence monitoring systems may process the data to provide a notification to the healthcare provider that the subject has wet their undergarment or absorbent pad. Although generally effective in monitoring the wetness of an undergarment or absorbent pad from a remote location, most conventional incontinence monitoring systems currently in use suffer from numerous drawbacks. These drawbacks include: (i) only capturing data input from a single electronic device (e.g., a moisture sensor), (ii) the need for a health care provider to directly observe and manually analyze any observations such as frequency of urination, (iii) moisture sensors rely on complex fabrication techniques and electrical conductivity or resistance for moisture detection, (iv) utilize a readout device electrically connected with the sensor, (v) require a power source, processor, and/or docking station integrated with the undergarment or absorbent pad, and/or (vi) the analysis for changing the undergarment or absorbent pad is typically based on a binary determination of wet or not wet.

To address these problems, various embodiments are directed to techniques for the implementation of an IoT solution to manage urinary incontinence. For example, one illustrative embodiment of the present disclosure comprises obtaining input data; parsing the input data to identify sensor data; comparing a first energy level and a second energy level from the sensor data to one or more energy levels; determining the first energy level is associated with a dry or normalized condition based on the comparison; determining the second energy level is associated with a moisture event based on the comparison; in response to determining the second energy level is associated with the moisture event, determining the sensor data does not include third energy level within a predefined period of time after receipt of the second energy level; and in response to determining the sensor data does not include third energy level, predicting, by a prediction model, a subject associated with the sensor data has had an incontinence event and a undergarment or absorbent pad associated with the subject has become saturated.

Another illustrative embodiment of the present disclosure comprises obtaining input data; parsing the input data to identify sensor data; comparing a first energy level and a second energy level from the sensor data to one or more energy levels; determining the first energy level is associated with an absence of motion based on the comparison; determining the second energy level is associated with a motion event based on the comparison; in response to determining the second energy level is associated with the motion event, determining the sensor data does not include third energy level within a predefined period of time after receipt of the second energy level; and in response to determining the sensor data does not include third energy level, predicting, by a prediction model, a subject associated with the sensor data has rolled over in bed.

Another illustrative embodiment of the present disclosure comprises obtaining input data; parsing the input data to identify sensor data; comparing a first energy level and a second energy level from the sensor data to one or more energy levels; determining the first energy level is associated with a dry or normalized condition based on the comparison; determining the second energy level is associated with a moisture event based on the comparison; in response to determining the second energy level is associated with the moisture event, determining the sensor data does include a third energy level within a predefined period of time after receipt of the second energy level; and in response to determining the sensor data does include the third energy level, predicting, by a prediction model, a subject associated with the sensor data has had an incontinence event and a undergarment or absorbent pad associated with the subject is not saturated.

II. Management System

FIG. 1 shows a management platform 100 that allows for end users such as health care providers, caretakers, or medical personnel to manage and monitor one or more subjects through one or more client devices 105 using a network of sensors 110 and IoT devices 115. While a number of client devices 105, sensors 110, and IoT devices 115 are shown in FIG. 1, one of ordinary skill in the art will appreciate that any number of client devices 105, sensors 110, and IoT devices 115 may be present within the management platform 100. The client devices 105 include any human-to-machine interface with network connection capability that allows access to a communication network 120 for communication with the network of sensors 110 and IoT devices 115. For example, the client devices 105 may include a stand-alone interface (e.g., a cellular telephone, a smartphone, a home computer, a laptop computer, a tablet, a personal digital assistant (PDA), a computing device, a wearable device such as a smart watch, a wall panel, a keypad, or the like), an interface that is built into an appliance or other device (e.g., a television, a refrigerator, a security system, a game console, a browser, or the like), a speech or gesture interface (e.g., a Kinect™ sensor, a Wiimote™, or the like), an IoT device interface (e.g., an Internet enabled appliance such as a medical device, a control interface, or other suitable interface), or the like. In some instances, a user may interact with the IoT devices 115 using an application (e.g., a management application), a web browser, a proprietary program, or any other program executed and operated by the client devices 105.

In some embodiments, the client devices 105 include a cellular or other broadband network transceiver radio or interface, and are configured to communicate with a cellular or other broadband communication network 120 using the cellular or broadband network transceiver radio. In some embodiments, the client devices 105 include a WiFi or other wireless network transceiver radio or interface, and are configured to communicate with a local area network (LAN) or other wireless communication network 120 using the WiFi or wireless network transceiver radio. In some embodiments, the client devices 105 include a cellular or other broadband communication transceiver radio or interface and a WiFi or other wireless network transceiver radio or interface, and are configured to communicate with a cellular or other broadband communication network 120 using the cellular or broadband network transceiver radio and with a LAN or other wireless communication network 120 using the WiFi or wireless network transceiver radio. For example, the client devices 105 may communicate with the network of sensors 110 and IoT devices 115 using Zigbee™ signals, Bluetooth™ signals, WiFi signals, infrared (IR) signals, Ultra-Wideband (UWB) signals, WiFi-Direct signals, Bluetooth™ Low Energy (BLE) signals, sound frequency signals, cellular data signals, or the like.

As used herein, a sensor 110 is a device, module, machine, or subsystem whose purpose is to detect events (e.g., physical properties) or changes in its environment and send the information to other electronic devices (e.g., an IoT device). The sensors 110 may include any number and type of sensors for sensing any number and type of event or change in the environment, and are configured to communicate data regarding the event or change in the environment to an IoT device 115. In some instances, the sensors include one or more moisture sensors. The one or more moisture sensors may be attached to an undergarment or absorbent pad and configured to communicate moisture data to an IoT device 115. In other instances, the sensors include one or more moisture sensors and an optional pressure sensor. The one or more moisture sensors and an optional pressure sensor may be attached to an undergarment, absorbent pad, or combination thereof and configured to communicate moisture data and optional pressure data to an IoT device 115. The IoT device 115 will receive the moisture data and optional pressure data and transmit this data to a gateway 125, cloud network 130, and/or client device 105 via communication network 120.

As used herein, an IoT device 115 is a device that includes sensing, control and/or analytical functionality as well as a WiFi™ transceiver radio or interface, a Bluetooth™ transceiver radio or interface, a Zigbee™ transceiver radio or interface, an UWB transceiver radio or interface, a WiFi-Direct transceiver radio or interface, a BLE transceiver radio or interface, radio frequency identification (RFID) or interface, cellular radio or interface and/or any other wireless network transceiver radio or interface that allows the IoT device 115 to communicate with a LAN, wide area network (WAN), cellular network, or the like and/or with one or more other devices (e.g., sensors or other IoT devices). In some embodiments, an IoT device 115 includes a cellular transceiver radio, and is configured to communicate with a cellular network using the cellular network transceiver radio. In some embodiments, an IoT device 115 includes a wireless transceiver radio, and is configured to communicate with a wireless network using the wireless network transceiver radio. The IoT device 115 includes a RFID reader, and is configured to communicate with a RFID sensor using RFID signal broadcast or interface. In some embodiments, an IoT device 115 includes a cellular transceiver radio, wireless transceiver radio, and a RFID reader. The IoT device 115 further includes one or more processors configured for analysis such as edge computing which brings computation and data storage closer to the location where it is needed (at or near the source of the data, e.g., the sensors), to improve response times and save bandwidth.

In some instances, the IoT device 115 may include automation network devices that allow a user to access, communicate, control, and/or configure various medical devices, sensors 110, or tools located within an environment or venue (e.g., a sensor, humidifier, respirator, hospital bed, bathroom lift, mobility scooter, a printer, a computer, and/or the like), or outside of the environment or venue (e.g., motion sensors, transport systems, or the like). For example, the IoT device 115 may be a hub device in communication with one or more sensors 110 (e.g., RFID moisture sensors) that "connects" a subject to a communication network 120, a gateway 125 and/or cloud network 130. In some embodiments, the IoT devices 115 may be used in various environments or venues, such as a hospital, a nursing home, an establishment, a personal care home, a subject's house, or any place that can support the management platform 100 to enable communication with IoT devices 115. For example, IoT devices 115 can allow a user to access, communicate, control, and/or configure devices, such as medical devices (e.g., a pelvic floor stimulator, a Foley bag, infusion pump, incontinence control device, moisture sensor, or the like), computing devices (e.g., a personal computer, a laptop computer, a tablet, a personal digital assistant (PDA), a computing device, a wearable device, or the like), lighting devices (e.g., a lamp, recessed lighting, or the like), devices associated with a security system, devices associated with an alarm system, and/or the like. In some instances, the IoT devices 115 include hardware, software, or a combination thereof that allow for an audible alarm to be emitted in response to predetermined events determined from received sensor data (e.g., moisture data and optional pressure data), and for the audible alarm, the predetermined event, or response of the subject or healthcare provider to the predetermined event to be acknowledged by a contact sensor, mechanical interface button, graphical user interface button, or the like.

The communication network 120 may be a wireless network, a wired network, or a combination of a wired and wireless network. A wireless network may include any wireless interface or combination of wireless interfaces (e.g., Zigbee™, Bluetooth™, WiFi™, IR, UWB, WiFi-Direct, BLE, cellular, Long-Term Evolution (LTE), WiMax™, or the like). A wired network may include any wired interface (e.g., fiber, ethernet, powerline ethernet, ethernet over coaxial cable, digital signal line (DSL), or the like). The communication network 120 may be implemented using various routers, access points, bridges, gateways, or the like, to connect devices in the management platform 100. For example, the communication network 120 may connect the client devices 105, the sensors 110, the IoT devices 115, the gateways 125, and the cloud network 130.

In some instances, the one or more gateways 125 are integrated with the IoT devices 115 as singular devices. In other instances, the one or more gateways 125 are separate from the IoT devices 115. In either instance, the one or optional gateways 125 can provide communication capabilities to the IoT devices 115 and/or the client devices 105 via radio signals in order to provide communication, location, and/or other services to the IoT devices 115. The network access provided by gateways 125 may be of any type of network familiar to those skilled in the art that can support data communications using any of a variety of commercially-available protocols. For example, gateways 125 may provide wireless communication capabilities for the communication network 120 using particular communications protocols, such as WiFi™ Zigbee™, Bluetooth™, infrared (IR), RFID, cellular, Long-Term Evolution (LTE), WiMax™, or other wireless communication technologies, or any combination thereof. In some instances, the gateways 125 may provide the client devices 105 and the IoT devices 115 with access to one or more external networks, such as the cloud network 130, the Internet, and/or other wide area networks. While a single gateway 125 is shown in FIG. 1, one of ordinary skill in the art will appreciate that any number of gateways may be present within the management platform 100.

The cloud network 130 may include a cloud infrastructure system that provides cloud services. In certain embodiments, services provided by the cloud network 130 include a host of services that are made available to users of the cloud infrastructure system on demand, such as registration, access control of the IoT devices 115, and analytics. Services provided by the cloud infrastructure system can dynamically scale to meet the needs of its users. The cloud network 130 may comprise one or more computers, servers, and/or systems. In some embodiments, the computers, servers, and/or systems that make up the cloud network 130 are different from the user's own on-premises computers, servers, and/or systems. For example, the cloud network 130 may host an application, and a user may, via communication network 120 such as the Internet, on demand, order and use the application.

In some embodiments, the cloud network 130 may implement a technique for establishing and maintaining Internet protocol connections across gateways or devices (e.g., a Network Address Translation (NAT) Traversal application) in order to establish a secure connection between the cloud network 130 and one or more of the IoT devices 115. For example, a separate secure Transmission Control Protocol (TCP) connection may be established by each of the IoT devices 115 for communicating between each of the IoT devices 115 and the cloud network 130. In some embodiments, each secure connection may be kept open for an indefinite period of time so that the cloud network 130 can initiate communications with each respective IoT device 115 at any time. In some cases, other types of communications between the cloud network 130 and the IoT devices 115 and/or the client devices 105 may be supported using other types of communication protocols, such as a Hypertext Transfer Protocol (HTTP) protocol, a Hypertext Transfer Protocol Secure (HTTPS) protocol, or the like. In some embodiments, communications initiated by the cloud network 130 may be conducted over the TCP connection, and communications initiated by a network device may be conducted over a HTTP or HTTPS connection. In certain embodiments, the cloud network 130 may include a suite of applications, middleware, and database service offerings that are delivered to a customer in a self-service, subscription-based, elastically scalable, reliable, highly available, and secure manner.

As described in detail herein, the management and monitoring one or more subjects through the client devices 105 using the network of sensors 110 and IoT devices 115 may include analyzing and viewing various forms of data, including (i) streaming or batch sensor data such as an RFID signals (e.g., impedance value), and (ii) locally or remotely stored sensor data or medical data such as historical RFID signals and medical history data. The sensors 110 and IoT devices 115 are typically located in a nursing home resident room, hospital room, bedroom, or other environment occupied by the one or more subjects. In some instances, one or more of the sensors 110 and/or IoT devices 115 may be located in a room of one or more subjects and one or more of the client devices 105 may be remote from the room such as, for example, at a nurses station or a health care provider's facility. In any event, it should be understood that the sensors 110 and/or IoT devices 115 might be placed anywhere that the one or more subjects are present in order to continuously, semi-continuously, or periodically monitor the health and wellbeing of the one or more subjects (including a medical condition of the subjects (e.g., urinary incontinence).

The client devices 105 may comprise a graphical user interface (GUI) or a browser application provided on a display (e.g., monitor screen, LCD or LED display, projector, etc.). An end user operating the client devices 105 may be presented one or more of these interfaces that accept input to enable the end user to interact with the management platform 100 via the communications network 120. The one or more interfaces executing on the client devices 105 may be accessible using a management application. The one or more interfaces and management application may be implemented to communicate content data such as, for example, textual content, multimedia content (e.g., images), or the like between the client devices 105, the network of sensors 110 and IoT devices 115, and the remote server(s) 145. In some instances, the management application is independently operable on the client devices 105 for collecting data from the network of sensors 110 and IoT devices 115, displaying the data, and analyzing and tracking data (without having to connect to the remote server(s) 140 for a majority of its functionality). In other instances, the management application is dependently operable on the client devices 105 for collecting data from the network of sensors 110 and IoT devices 115, displaying the data, and analyzing and tracking data (required to connect to the remote server(s) 140 for at least some of its functionality).

The one or more interfaces and management application may be implemented by an end user to access the network of sensors 110 and IoT devices 115, such as to access a live data feed and monitor one or more subjects. Additionally or alternatively, an end user may use the one or more interfaces and management application to access the remote servers 140, such as to review data obtained and saved in the data store 145 by the client devices 105 or IoT devices 115. For example, during monitoring, the IoT devices 115 capture data (e.g., sensor data from one or more subjects) and transmit the data to one or more client devices 105 and/or the remote servers 140. The one or more client devices 105 process and output the data to one or more displays, such as a display at the client device 105 or another location, such as client device 105. The remote servers 140 process and save the data in the data store 145 such that a client devices 105 can access the remote servers 140 to review the data obtained and saved in the data store 145.

At the one or more client devices 105 and/or the remote servers 140, an analytical system may process the incoming content data using one or more trained machine learning (ML) techniques to identify, analyze, and track health care data such as metrics of subject's wellbeing including urinary incontinence. In some examples, the incoming data is processed in real-time or near-real-time. Alternatively, processing may not be done in real-time (or near-real-time), but may instead be processed after a request for analysis or after a period of time of a monitoring session to collect a greater scope of data and possibly improve the analysis. In some instances, the one or more interfaces and management application may be implemented by an end user to perform a variety of additional tasks (beyond the monitoring of one or more subjects), such as: (i) searching and browsing the content data, (ii) analyzing and reviewing health care data, (iii) inventory control, and (iv) personnel management.

Figure 2:
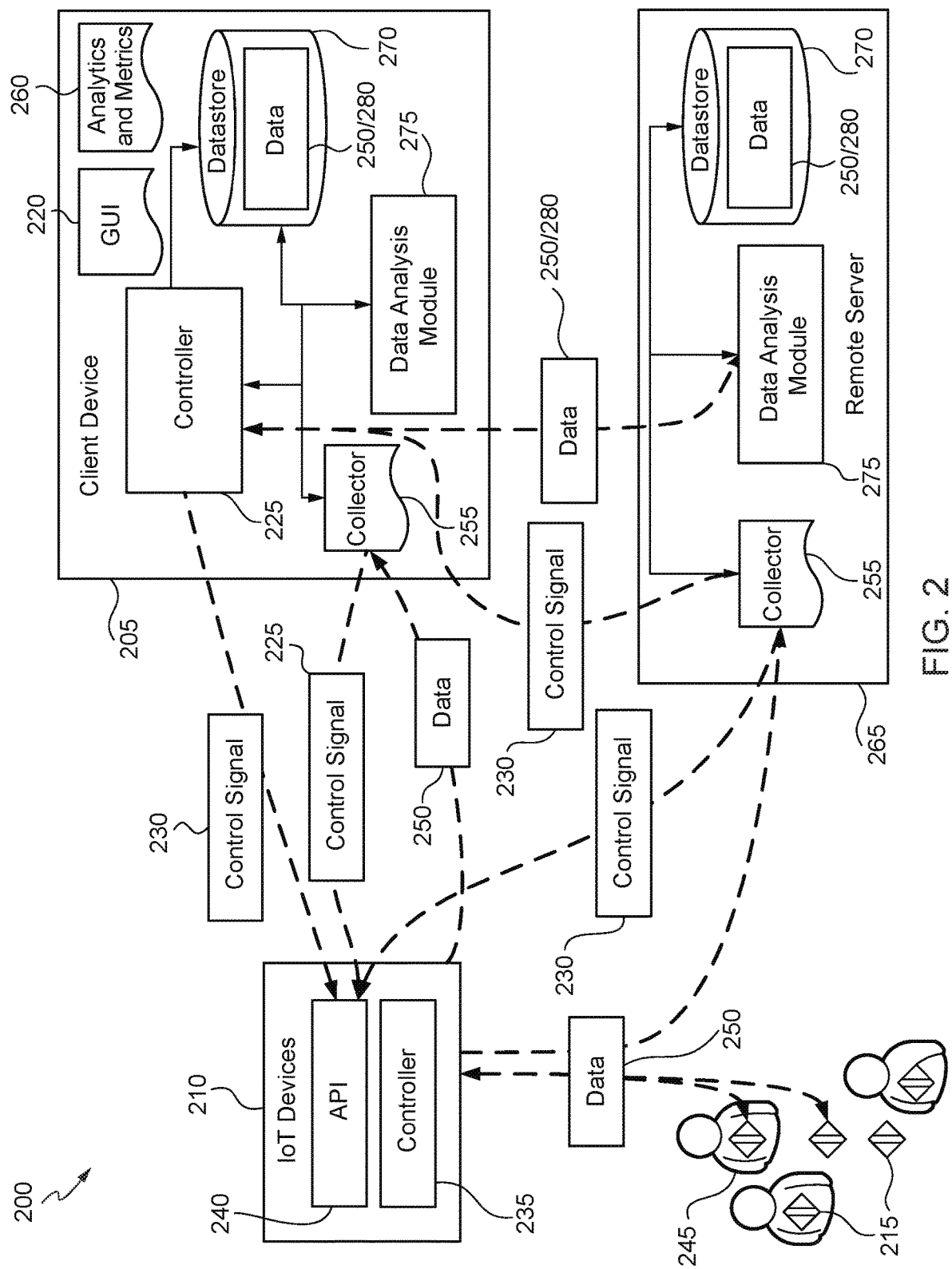
FIG. 2 shows a simplified block diagram illustrating a management system in accordance with various embodiments.

FIG. 2 shows a management system 200 (e.g., a computing system implemented within management platform 100 described with respect to FIG. 1) for implementation of an IoT solution to manage healthcare including urinary incontinence of one or more subjects. In some instances, the management system 200 includes one or more client devices 205 in communication with a network of IoT devices 210 and sensors 215. The client devices 205 may be operated by an end user via an interface 220 (e.g., a GUI) and controller 225 to access the IoT devices 210. In some instances, an end user uses the interface 220 to access controller 225 to control the IoT devices 210 by sending corresponding control signals 230 to the IoT device controller 235 via an application program interface 240 (API). The IoT devices 210 may be controlled with controller 225 to monitor the health and wellbeing of one or more subjects 245. For example, an end user may turn on, configure, or operate or instruct the IoT devices 210 to begin obtaining data 250 from sensors 215. In other instances, an end user uses the interface 220 to access controller 225 to configure a collector 255 of the client devices 205 and/or the remote servers 260. The collector 255 may be configured by the end user to automatically turn on, configure, or operate the IoT devices 210 (e.g., on a schedule or like manner instruct the IoT devices 210 to begin obtaining data 250 (e.g., sensor data). The collector 255 may control the IoT devices 210 by sending corresponding control signals 230 to the IoT device controller 235 via the API 240. The controller 225 and collector 255 may be part of a management application implemented by an end user to access the IoT devices 210, such as to access a live data feed, monitor the one or more subjects 245, and obtain analytics or metrics 260.

The collector 255 of the client devices 205 and/or remote servers 265 may collect and process the data 250 in real time via a live streaming protocol to stream sensor data to client devices 205 (as an application or through a web browser connection to web interface). In some instances, the remote servers 265 are implemented within a distributed environment such as a cloud network (e.g., cloud network 130 as described with respect to FIG. 1). The live streaming provides formatting capabilities to produce live streaming data for download by end users from the data 250 received at the collector 255. Live streaming data received by an end user at client devices 205 may comprise a real-time sensor stream including readings from the sensors 215. The real-time sensor stream may be observed, recorded, paused, and viewed as a real time or time-lapsed stream of events via the one or more interfaces 220. Alternatively, the collector 255 of the client devices 205 or remote servers 265 system may collect and process the data 245 over a period of time via batch data processing to provide sensor data to client devices 205 (as an application or through a web browser connection to web interface). In some instances, the batch data may be saved in the one or more memory devices or data stores 270. The batch data processing provides formatting capabilities to produce batched data for download by end users from the data 250 received at the collector 255. Batched data obtained by end users at client devices 205 may comprise recorded sensor readings. The recorded sensor readings may be observed, recorded, paused, and viewed online or offline via the one or more interfaces 220.

The collector 255 may send the data 250 to the analytical system 275 of the client devices 205 and/or remote servers 265 to process the data 250 and provide analytics and metrics 260 of health care or wellbeing. The data 250 may be sent from the IoT devices 210 to the collector 255, where all or a portion of the sensor readings are processed, stored as training data sets or input data sets in the data stores 270, and analyzed using analytical system 275 as standalone data or as a supplement to other data such as the health care data from healthcare providers or medical devices and/or media data such as images or videos. Other data 250 such as medical device measurements may also be transmitted from the IoT devices 210 to the collector 255, where all or a portion of the measurements are processed, stored in the data stores 270, and analyzed using analytical system 275 as standalone data or as a supplement to other data such as the health care data from healthcare providers or medical devices and/or media data such as images or videos. In some instances, the controller 235 of the IoT devices 210 includes logic, memory, and processing components to pre-process, partially process, or completely process the data 250 and optionally provide analytics and metrics 260 of health care or wellbeing for one or more subjects. For example, the controller 235 of the IoT devices 210 may be configured to parse the sensor readings, place the sensor readings into bins depending on pattern recognition, and optionally identify incontinence events such as diaper saturation based on the pattern recognition.

The analytical system 275 includes logic, memory, and processing components such as one or more machine learning models and service modules. The analytical system 275 may be configured to receive the data 250 as well as any other relevant information (e.g., subject profile, product inventory, personnel data, or medical data from user input, account, or third party sources), process the data 250 using logic and/or one or more machine learning models, analyze the processed data 250, and generate output data. In some instances, the output data may be used to provide services provided by the service modules. In some instances, the output data may be used in one or more operations for detecting the patterns of incontinence of the one or more subjects 245, detecting patterns of use of undergarments and absorbent pads, obtain or determine location or position information concerning the one or more subjects 245, predicting the wellbeing of the one or more subjects 245, and determining and predicting personnel status and potential staffing issues. The results of the one or more operations may be used individually or combined with output from other models or sources to provide services provided by the service modules.

For example, results of analysis (online (real-time) or offline) by the logic and machine learning models may be used to provide services requested by end users such as alerts, notifications, summaries of activities, and subject profile information. Exemplary services that can be provided by the service modules may include a summary of urinary incontinence for a subject over time, a summary of undergarment and absorbent pad use over time for one or more subjects, a summary of movement or location of one or more subjects overtime, a notification upon request when certain urinary incontinence events occur (e.g., undergarment and absorbent pad wetting or saturation), a notification upon request when certain activity is detected (e.g., a subject getting out of bed or leaving a room), a notification upon request when certain level of product inventory occurs (e.g., a number of undergarments, absorbent pads, or disposable sensors reaches a predetermined threshold), and a summary of the health state of the subject over a past time period. Other services may include allowing users to view and share data and/or summaries with other users, healthcare providers, caretakers, family, or medical personnel. Another service may allow users to write comments on shared data and/or summaries.

The service modules may provide machine-to-machine interaction and are operable to communicate data 250 and services data 280 between client devices 205 and remote servers 255. Users may log into the service modules by using an interface 220 and identifying a profile or account. In some instances, authentication and/or authorization of the user may be requested in order to log into the profile or account and use the service modules. The client devices 205 may request services data 280 from the service modules. The service modules may process the request and provide services data 280 to the requesting client devices 205. The services data 280 may include messages, alerts, statistics, charts, and remote functions. In some instances, the services data 280 may be either transmitted along with or independently of data 250 from IoT device 210. For example, client devices 205 may receive data 250 from the IoT devices 210 via a router on a LAN connection and receive services data 280 from the management application executing on the client devices 205 or over a WAN from the remote servers 265. Alternatively, the client devices 205 may receive both data 250 and services data 280 as a single data stream over a WAN from the remote servers 265. Data transmission configurations according to various embodiments are not limited to the described examples and may include other configurations that allow for data 250 and services data 280 to be received by client devices 205.

The data stores 270 (e.g., databases) may include analytical data including the profile or medical data (e.g., the age, temperature, weight, etc. of a subject), data 250, the services data 280, metrics of health care or wellbeing for one or more subjects over any given period of time. For example, a incontinence chart for each subject along with other health or medical related data (e.g., temperature of infusion parameters) at the time of measurement. The analytical data may also include statistics comparing service data 270 or metrics of one subject versus another subject or a comparison of one or more subjects against a population of subjects (e.g., a population within a same age range and/or gender). For example, these statistics may include a comparison of incontinence events during a certain work shift, incontinence events and length of time before changing of a undergarment and absorbent pad, or patterns of incontinence events. The analytical data may be used to display the correlation between profile or medical data.

It should be appreciated that although FIG. 2 illustrates a technique to monitor healthcare including urinary incontinence of one or more subjects in the context of a management system 200, it can be implemented in other types of systems and settings. For example, this technique can be implemented in a computing device separate from a management system 200 and/or be performed offline after the monitoring is completed or during a period of inactivity by the subject. It should also be appreciated that although FIG. 2 illustrates a technique to monitor healthcare including urinary incontinence of one or more subjects using sensor recordings, it can be implemented using additional or alternative data, for example, electrocardiogram (EKG) or infusion pump parameters, from one or more medical devices.

III. Absorbent Articles, Sensors, and IoT Devices

Figure 3A:
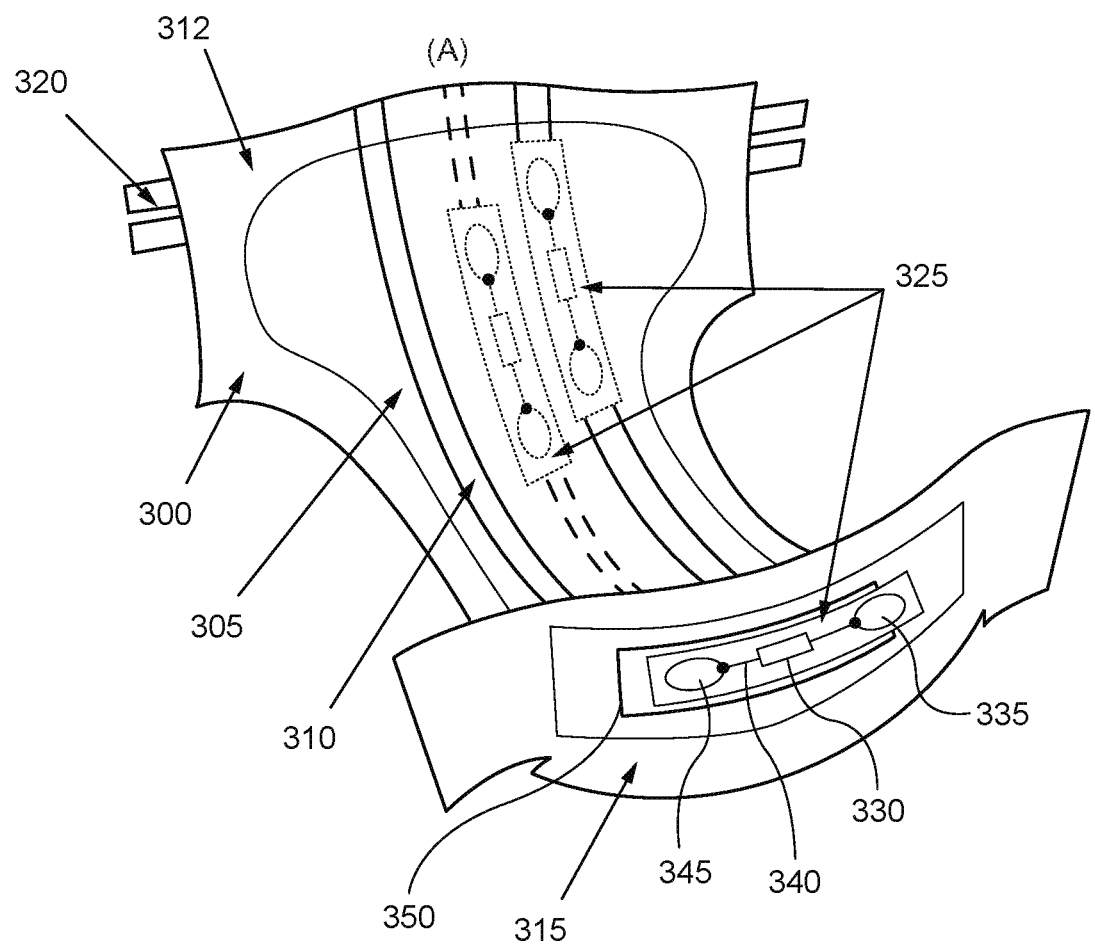
FIGS. 3A-3E show a medical device and various sensor arrangements in accordance with various embodiments.

FIG. 3A depicts an absorbent article 300 (e.g., an undergarment or absorbent pad) (although an undergarment such as a diaper is shown it should be understood that similar features could be used in an absorbent pad or other absorbent article) in accordance with at least one embodiment of the present disclosure. As used herein, the term "undergarment" refers to a garment generally worn by incontinent persons, which is disposed between the legs and capable of absorbing and retaining liquids. In some embodiments, the absorbent article 300 comprises a liquid permeable top sheet 305 (e.g., hydrophilic polypropylene nonwovens), an absorbent material 310, a nonabsorbent material 312, a liquid impermeable back sheet 315, and fasteners 320. The top sheet 305, absorbent material 310, nonabsorbent material 312, liquid impermeable back sheet 315, and fasteners 320 may be assembled in a variety of well-known configurations. For example, as shown, the absorbent material 310 may be disposed under the liquid permeable top sheet 315 and the nonabsorbent material 312 disposed adjacent to at least a portion of the liquid permeable top sheet 315 or the absorbent material 310. The liquid impermeable back sheet 315 is disposed over the absorbent material 310 such that the absorbent material 310 is disposed between the liquid permeable top sheet 305 and the liquid impermeable back sheet 315.

The absorbent material 310 may be any material which is generally compressible, conformable, non-irritating to the wearer's skin, and which is capable of absorbing and retaining liquids. The absorbent material 310 may be manufactured in a wide variety of sizes and shapes (e.g., rectangular, hourglass, etc.) and from a wide variety of liquid absorbent materials commonly used in disposable diapers, such as comminuted wood pulp which is generally referred to as airfelt. Other liquid absorbing materials may also be used in the manufacture of the absorbent material 310 such as a multiplicity of plies of creped cellulose wadding, polymeric gelling agents, absorbent foams or sponges, or any equivalent material or combination of materials. The total absorbent capacity of the absorbent material 310 should, however, be compatible with the design liquid loading in the intended use of the absorbent article 300. Further, the size and absorbent capacity of the absorbent material 310 may be varied to accommodate wearers ranging from infants through adults.

In various embodiments, one or more sensors 325 (e.g., passive or active RFID sensors, or the like) are disposed on the absorbent article 300. In some embodiments, the one or more sensors 325 are formed as reusable and/or disposable tags that can be attached (e.g., with an adhesive, connector such as a magnet, or an attachment structure such as a sleeve) to the absorbent article 300. In other embodiments, the one or more sensors 325 are directly printed (e.g., 3D printed with conductive polymers or metals) on the absorbent article 300. The one or more sensors 325 may be attached or printed in any arrangement or pattern designed to achieve one or more functions. For example, in order to determine an incontinence event, the one or more sensors 325 may be attached or directly printed to the back side of the absorbent article 300 on the liquid impermeable back sheet 315 in an area aligned in a vertical plane (A) (form a cross-sectional perspective) with the absorbent material 310 or the nonabsorbent material 312 (i.e., over or under the absorbent material 310 or the nonabsorbent material 312 form a cross-sectional perspective). This arrangement keeps to sensors 325 from coming in contact with the subjects skin while maintaining functionality to detect moisture indicative of an incontinence event. In other instances, in order to detect moisture and movement of the subject, a first subset of sensors 325 may be attached or directly printed to the back side of the absorbent article 300 in an area aligned in a vertical plane (A) (form a cross-sectional perspective) with the absorbent material 310 and a second subset of sensors may be attached or directly printed to the back side of the absorbent article 300 in an area that is not aligned in a vertical plane (A) (form a cross-sectional perspective) with the absorbent material 310 (e.g., a back of the diaper up on the waist line aligned in a vertical plane (A) with the nonabsorbent material 312, as shown in FIG. 3A). This arrangement keeps the sensors 325 from coming in contact with the subjects skin while maintaining functionality to detect moisture indicative of an incontinence event and detect motion of the subject (even if the moisture in the absorbent material causes the first subset of sensors 325 to become inactive or unable to report reliable data consistent with movement).

The one or more sensors 325 may comprise a integrated circuit 330 having a transceiver or wireless communication module used to transmit and/or receive signals between two devices (e.g., the sensor and a IoT device). The integrated circuit 330 may further have a detection circuit configured to detect an electrical state (e.g., impedance) sensed at a detector 335 and/or a change in that electrical state and quantize the electrical state or change in electrical state, and a memory storage device for storing sensor recordings such as the quantitated value for the electrical state or change in electrical state (e.g., impedance values). The one or more sensors 325 may further comprise transmission lines 340 for conveying information including the parameter, signal, sensor recordings or quantitated values to the integrated circuit and/or an antenna 345. In some embodiments, the antenna is a dipole design and the detector 335 uses the transmission lines 340 to communicate the electrical state to the antenna 345, thus directly affecting the electrical state of the antenna 345. The detection circuit detects the electrical state or any resulting change in the electrical state at the antenna 345 and will quantize that electrical state or change in electrical state.

In some embodiments, one or more attachment structures 350 such as sleeves or straps are formed on or integrated with a portion of the absorbent article 300 to attach the one or more sensors 325 to the absorbent article 300. The absorbent article 300 may be manufactured with the one or more attachment structures 350 such that the absorbent article 300 is designed to hold the one or more sensors 325 in a preconfigured arrangement. Prior to use, the one or more sensors 325 can be attached to the absorbent article 300 using the one or more attachment structures 350 such that the one or more sensors 325 are implemented in the preconfigured arrangement. In some instances, the one or more attachment structures 350 may be used at the manufacturing level to place the one or more sensors 325 in the preconfigured arrangement. The one or more attachment structures 350 could be sized to accept only a sensor 325 of specific size corresponding to a sensor 325 signifying a specific absorbent article 300 type and size information. For example, the sensor 325 could be manufactured in different sizes with underlying Electronic Product Code ((EPC) information that matches with absorbent article 300 information. The location of the one or more attachment structures 350 would ensure that the ideal sensor location will be achieved. This location could be at the junction of the peripheral moisture margin and the zone of dry for maximal antenna response. For an absorbent article 300 detecting single voiding events with maximal sensitivity, the location may be over the mid anterior absorbent material 310. For fecal incontinence measurement, the location may be over the mid posterior absorbent material 310. For an absorbent article 300 tracking maximum capacity measurement as well as having geofencing or movement detection capability, an additional sleeve could be placed over the nonabsorbent material 312 to prevent signal degradation.

An absorbent article 300 can also be manufactured and sold as "RFID tag ready" with the ideal site or preconfigured arrangement for the one or more sensors 325 already predetermined or marked with one or more printed outlines or locators as compared to attachment of the one or more attachment structures 350. Thereafter, the one or more sensors 325 can be attached directly on the one or more printed outlines or locators via an adhesive or the like for ideal placement or in the preconfigured arrangement. Alternatively, the absorbent article 300 may be manufactured without the one or more attachment structures 350. Prior to use, the one or more attachment structure 350 could be attached to the absorbent article (e.g., with an adhesive or the like such as a tape) in a desired arrangement. In some instances, the one or more sensors 325 could be attached with a connector such as a magnet or Velcro system (e.g., a ferrous absorbent article element and an RFID associated magnetic element could be used). In other instances, the one or more sensors 325 could be placed inside a permanent plastic or polymer structure attachable to absorbent article 300 via one or more of the aforementioned solutions, thus permitting reuse and cleaning of the one or more sensors 325.

Figure 3B:
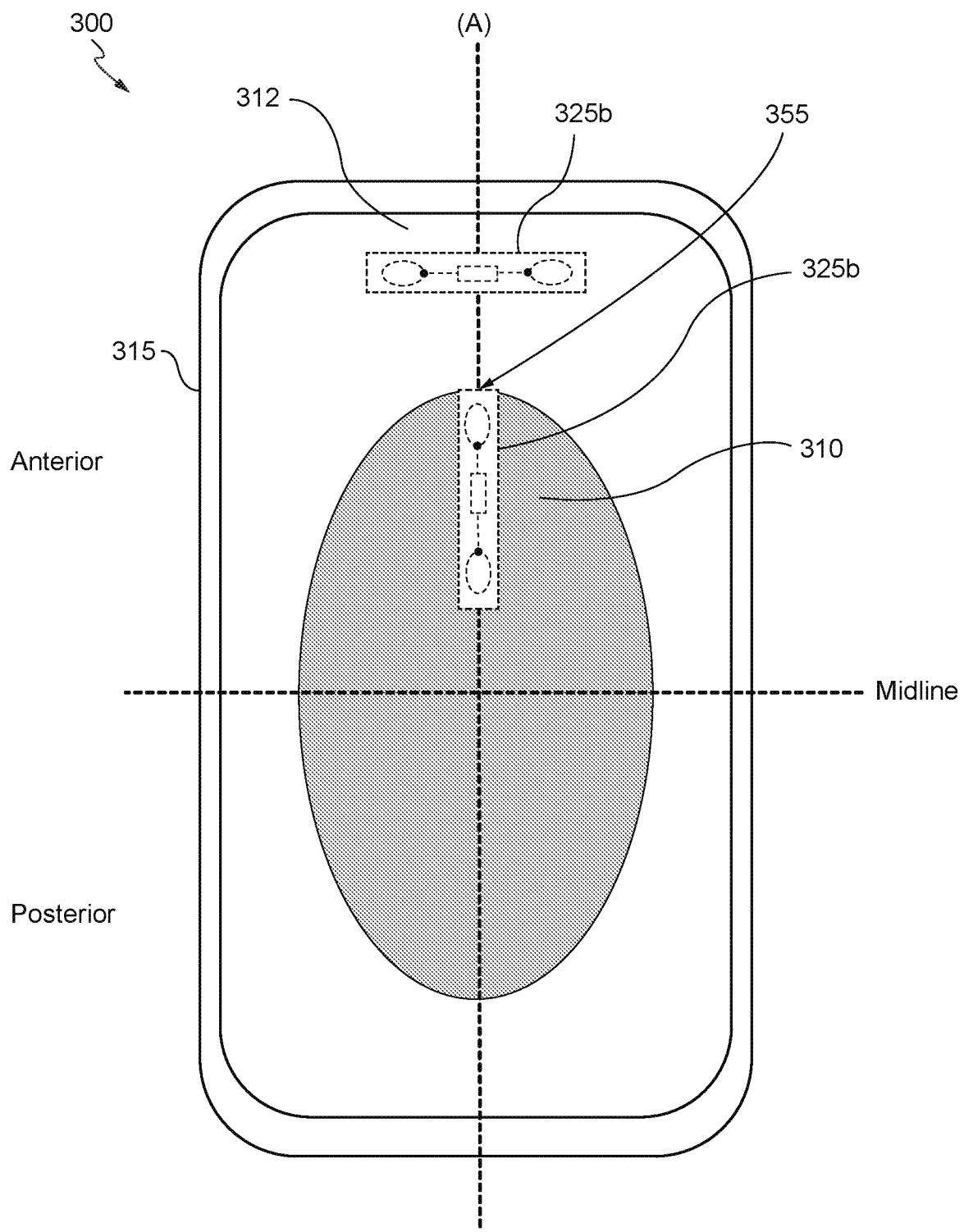

FIG. 3B depicts a planar view of an absorbent article 300 in accordance with at least one embodiment of the present disclosure. Sensor 325a is disposed on the anterior (front facing) side of the liquid impermeable back sheet 315 over, near or adjacent the interface 355 between the underlying absorbent material 310 and the nonabsorbent material 312 (an area of the article 300 that is aligned in a vertical plane (A) with the interface 355), and sensor 325b is disposed on the liquid impermeable back sheet over the outer margin of the nonabsorbent material 312 (an area of the article 300 that is aligned in a vertical plane (A) with the nonabsorbent material 312). In this context, near or adjacent to the interface means within 1 to 5 cm of the edge of the underlying absorbent material 310. The measurement by sensor 325b at the outer margin will be a leading indicator of maximal capacity and, with saturation, will reach a steady state; whereas measurement by sensor 325a at the absorbent material interface will be a leading indicator of the start of a wetting event, a drying event, and/or an unsaturated absorbent material. The change in energy state over time represents the rate of wetting and drying using a capillary model. As this energy state reaches an equilibrium number, this will correlate with device saturation. Once full capacity is reached, saturation occurs, and the absorbent article 300 is at risk for leaking. This is manifested by a static energy state measured by sensor 325b at the periphery of the undergarment or absorbent pad or complete loss of RFID signal from the sensor 325a as the liquid front obstructs the RFID antenna consistent with full peripheral diaper capacity.

Figure 3C:
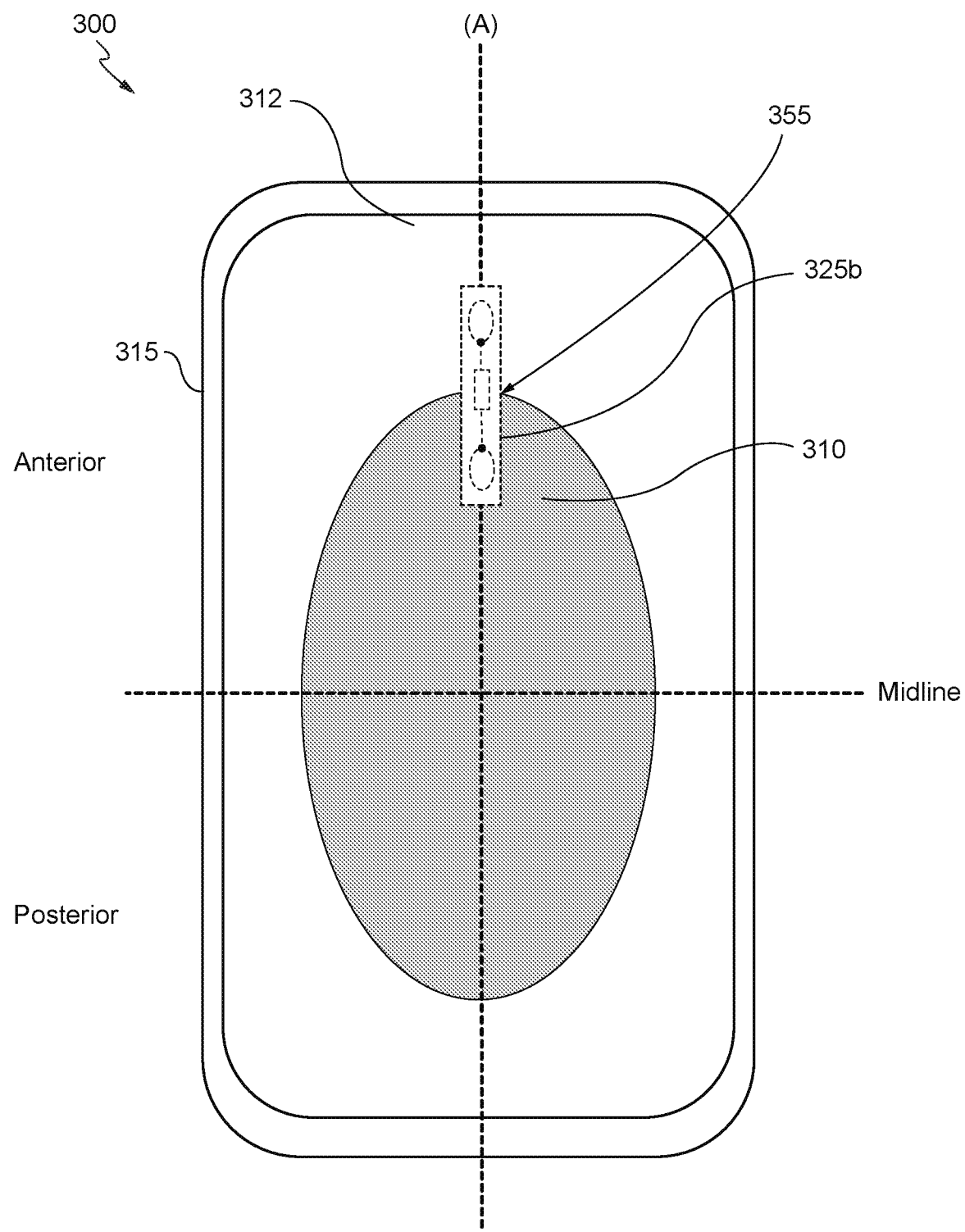

FIG. 3C depicts an planar view of an absorbent article 300 in accordance with an alternative embodiment of the present disclosure. Sensor 325a is disposed on the anterior (front facing) side of the liquid impermeable back sheet 315 hurdling the interface 355 between the underlying absorbent material 310 and the nonabsorbent material 312. This provides the ability to accomplish moisture sensing over the absorbent material 310 while permitting a portion of the sensor antenna to be placed over the nonabsorbent material 312 to maximize radio communication with the RFID reader. The measurement by sensor 325a at the interface 355 will be a leading indicator of maximal capacity and, with saturation, will reach a steady state. The change in energy state over time represents the rate of wetting and drying using a capillary model. As this energy state reaches an equilibrium number, this will correlate with device saturation. Once full capacity is reached, saturation occurs, and the absorbent article 300 is at risk for leaking. This is manifested by a static energy state measured by sensor 325b at the periphery of the undergarment or absorbent pad.

Figure 3D:
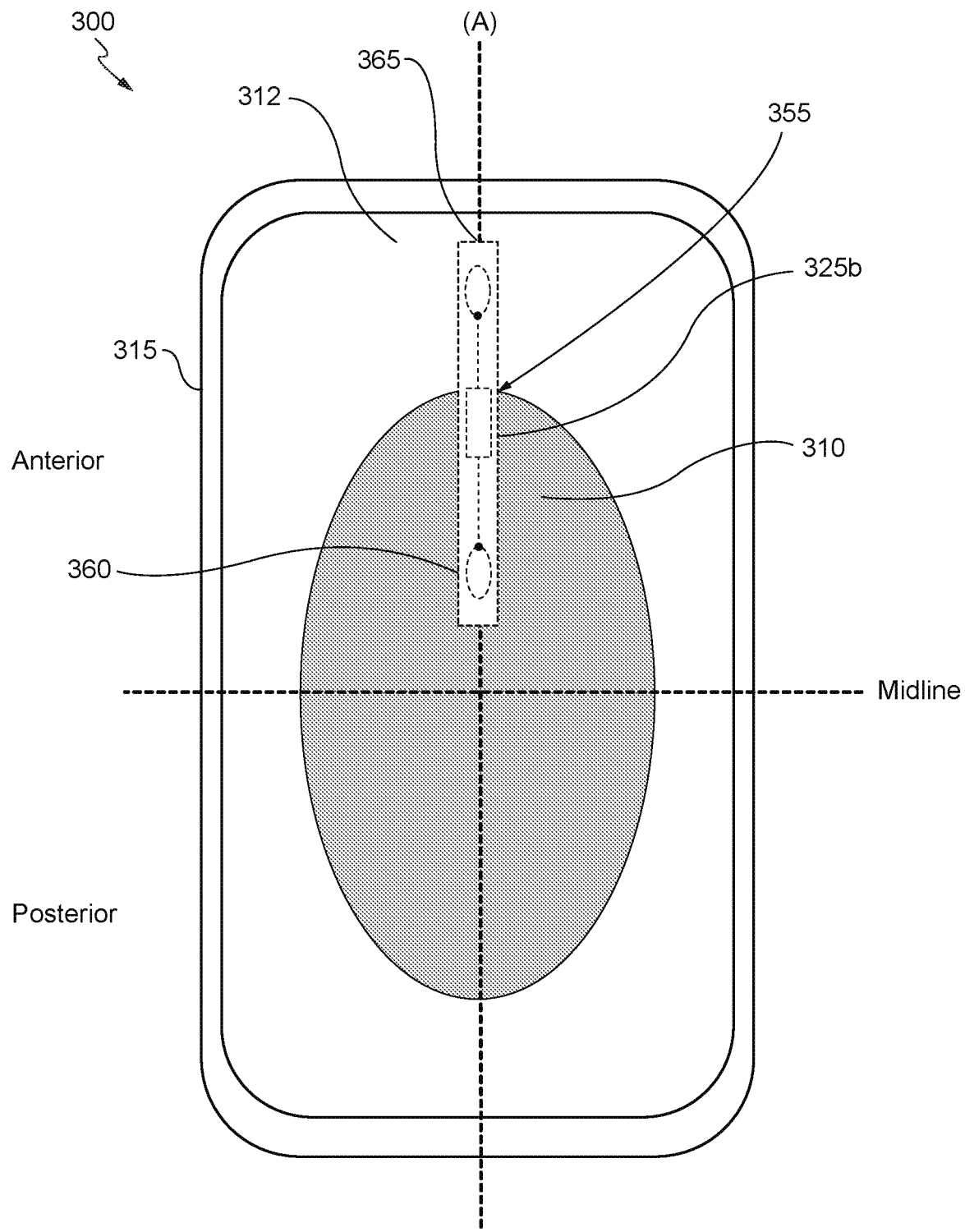

FIG. 3D depicts an planar view of an absorbent article 300 in accordance with an alternative embodiment of the present disclosure. Sensor 325a is disposed on the liquid impermeable back sheet 315 hurdling the interface 355 between the underlying absorbent material 310 and the nonabsorbent material 312. In this instance, sensor 325a has been modified with a moisture detection component 360 placed at any point of the moisture front (an area of the article 300 that is aligned in a vertical plane (A) with the underlying absorbent material 310) with an associated extended antenna 365, which would be located in an area outside the area of moisture absorbency, e.g., aligned in a vertical plane (A) with the nonabsorbent material 312. This provides the ability to accomplish moisture sensing over the absorbent material 310 while permitting a portion of the sensor antenna to be placed over the nonabsorbent material 312 to maximize radio communication with the RFID reader. The measurement by sensor 325a at the interface 355 will be a leading indicator of maximal capacity and, with saturation, will reach a steady state. The change in energy state over time represents the rate of wetting and drying using a capillary model. As this energy state reaches an equilibrium number, this will correlate with device saturation. Once full capacity is reached, saturation occurs, and the absorbent article 300 is at risk for leaking. This is manifested by a static energy state measured by sensor 325*ba* at the periphery of the undergarment or absorbent pad.

Figure 3E:
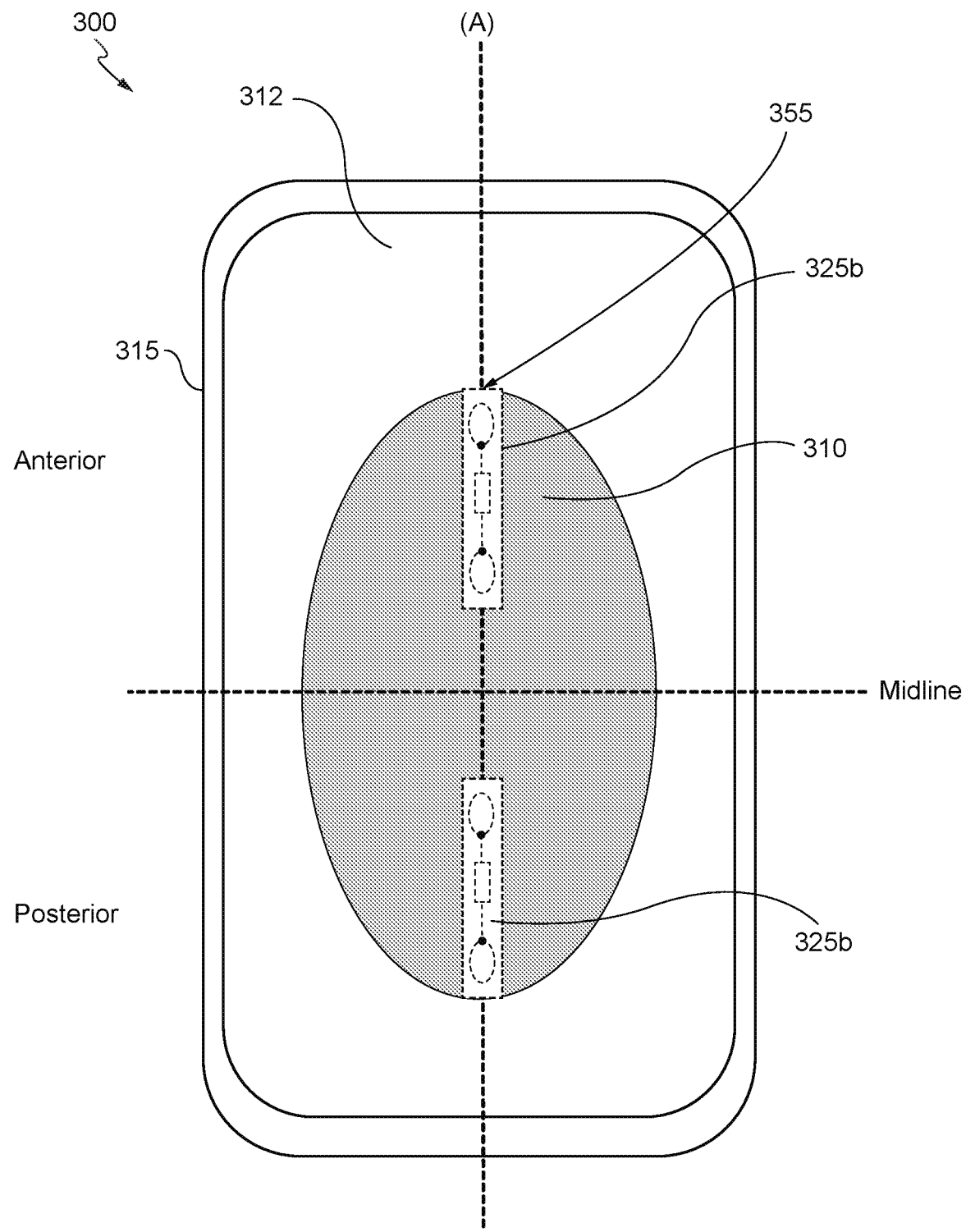

FIG. 3E depicts an planar view of an absorbent article 300 in accordance with an alternative embodiment of the present disclosure designed to distinguish between urinary and fecal incontinence. The detection of urinary incontinence depends on the placement of the sensor 325*a* on the anterior (front facing) side of the liquid impermeable back sheet 315; whereas fecal incontinence detection depends on the placement of the sensor 325*b* on the posterior (rear facing) side of the liquid impermeable back sheet 315. Sensors 325*a* and 325*b* can be disposed at the outer margin over the nonabsorbent material 312 (an area of the article 300 that is aligned in a vertical plane (A) with the nonabsorbent material 312) or hurdling the interface 355 between the underlying absorbent material 310 and the nonabsorbent material 312. The measurement by sensor 325*a* will be a leading indicator of maximal capacity and, with urinary saturation, will reach a steady state or complete loss of RFID signal from the sensor 325*a* as the liquid front obstructs the RFID antenna. The change in energy state over time represents the rate of wetting and drying using a capillary model.

The measurement by sensor 325*b* will be a leading indicator of a fecal incontinent event, and will reach a steady state or complete loss of RFID signal from the sensor 325*a* as the fecal matter obstructs the RFID antenna. The change in energy state over time represents a fecal incontinent event. Fecal events (incontinent or continent) typically follow a regular diurnal pattern. Data logging followed by data analytics based on the edge/cloud platform could be used to create a predictive model of future fecal events. The predictive model may then be used to inform the health care provide or care giver regarding potential for intervention prior to a fecal incontinent event. The management of fecal events may be greatly simplified by assisting the subject to use the toilet facilities rather than defecating in the absorbent article 300. Additional, data including feeding interval and volume or amount could be provided as input into predictive model to optimize prediction of future fecal events and time for toileting.

Figure 4A:
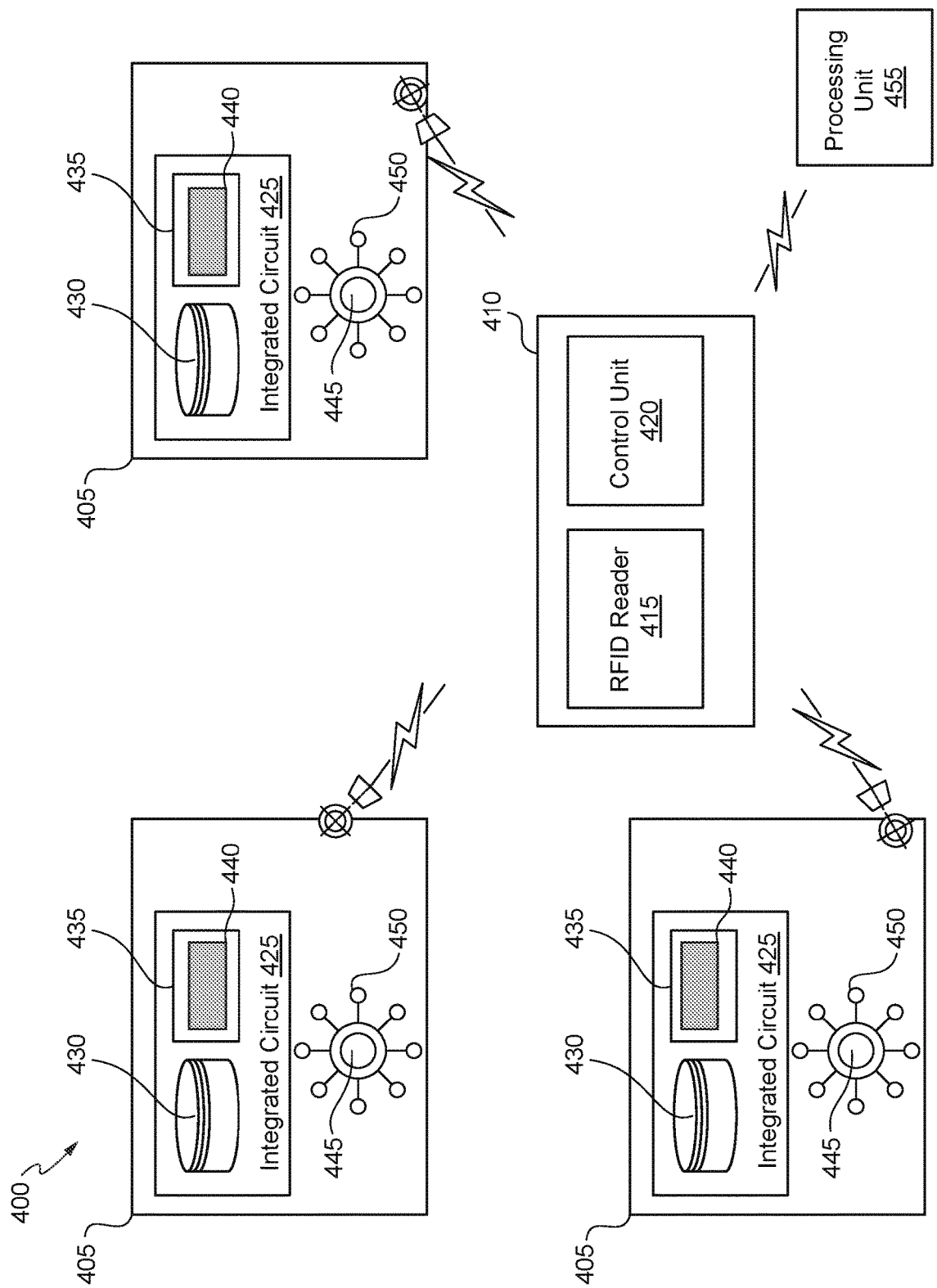
FIG. 4A shows a simplified block diagram illustrating a wireless solution in accordance with various embodiments.

FIG. 4A depicts a block diagram of a wireless solution 400 in accordance with at least one embodiment of the present disclosure. In conventional moisture sensor systems for urinary incontinence, a sensor is configured to measure moisture or humidity via capacitive measurement or resistance measurement of hygroscopic (moisture-absorbing) material that attracts moisture and when the moisture makes contact with metal plates or conductive paths the moisture creates a voltage change or resistance change. These conventional systems are typically bulky and require a readout device attached to a docking element which connects to the metal plates or conductive paths of the sensor to obtain capacitive measurements or resistance measurements. The readout device can then be undocked from the sensor and subsequently plugged into an analysis system or wirelessly transmit the sensor data to the analysis system. In contrast, the wireless solution 400 of the present disclosure comprises one or more RFID sensors 405 (e.g., the sensors 325 described with respect to FIGS. 3A and 3B) and a separate IoT device 410 comprising a RFID reader 415 and control unit 420 that can communicate wirelessly with the one or more RFID sensors 405. Although only one IoT device 410 is shown. it should be understood that a second or multiple IoT devices 410 may be used communicate wirelessly with the one or more RFID sensors 405. The one or more RFID sensors 405 and the IoT device 410 use a form of wireless communication that uses radio waves to identify, determine, and track devices. The one or more RFID sensors 405 and the IoT device 410 may use radio waves with a low frequency (LF), high frequency (HF), ultra-high frequency (UHF), or a combination thereof. The IoT device 410 is capable of communicating wirelessly with more than one RFID sensor 405 simultaneously. The RFID reader 415 and control unit 420 of the IoT device 410 are capable of retrieving the sensor data from the one or more RFID sensors 405, processing the sensor data, and/or communicating the sensor data wireless to an analysis system. Accordingly, the IoT device 410 does not need to be docked directly with the one or more RFID sensors and instead the IoT device 410 can actively or passive retrieve sensor data from the one or more RFID sensors 405.

The control unit 420 of the IoT device 410 is capable of transmitting a signal (radio waves) via the RFID reader 415, which is directed to the one or more RFID sensors 405 using a polarized antenna. In some instances, the control unit 420 and/or the RFID reader 415 incorporates dynamic power variation in order to limit RFID exposure. An RFID system with maximal legal power output has the benefit of simplicity but has the disadvantage of excessive subject exposure to RFID as well as potential reading range impairment from excess backscatter. The IoT device 410 may employ a power strategy which includes discrete reading intervals followed by periods of non-reading. During these discrete reading intervals, power is varied from the lowest level until a read is achieved. The reader power is then increased until a read occurs or a time-out event occurs. The power level never surpasses the FCC legal limit. If a separate wrist band is worn, connectivity power levels are driven by the last non read sensor (diaper) which can often require higher power levels Each of the one or more RFID sensors 405 comprises an integrated circuit 425 having a memory storage device 430 and a controller 435 with wireless communication module 440, and a detector 445 which includes an antenna 450. The one or more RFID sensors 405 will harvest energy from the signal transmitted by the RFID reader 415, which will energize each of the one or more RFID sensors 405. Once energized, the integrated circuit 425 is capable of sensing a change in the environmental perimeters (e.g., moisture changes) proximate to detector 445 via energy state changes (e.g., impedance changes) associated with antenna 450. In some embodiments, the one or more RFID sensors 405 is further capable of sensing a proximity of the RFID sensor 405 to the RFID reader 415 via energy state changes (e.g., impedance changes) associated with antenna 450. For example, when a given RFID sensor 405 is in close proximity to moisture or the RFID reader 415, the RFID sensor 405 will achieve a different energy state compared to when no moisture is in close proximity or the RFID sensor 405 is moving away from the RFID sensor 405. The memory storage device 430 is coupled with the controller 435, wireless communication module 440, and detector 445. The memory storage device 430 is capable of storing information and sensor data gathered by the detector and communicate the sensor data via wireless communication module 440 with the RFID reader 415. For example, the energy state of the RFID sensor 405 may be reported back to the RFID reader 415 with changes in reflected energy received by the RFID reader 415. Each RFID sensor 405 has a unique identifier such that a relationship of the RFID sensor 405 and their associated state will be identified and maintained by the IoT device 410. Further, wireless communication module 440 and detector 445 are fully programmable via wireless methods with the IoT device 410.

In some embodiments, the integrated circuit 425 contains sensor data such as a digital representation of an energy state (e.g., a quantitative impedance value stored in memory storage device 430) detected by the detector 445, and the sensor data may be used either internally by the RFID sensors 405, or read and used by the RFID reader 415, to discern relative environmental information to which the RFID tag is exposed (e.g., dry or moist conditions). For example, the RFID reader 415 may issue a command to the RFID sensors 405 to activate integrated circuit 425 and/or detector 445 and, subsequent to the respective operations of integrated circuit 425 and/or detector 445, receive the digital representations of an energy state (e.g., a quantitative impedance value). The digital representations of the energy state may be used either internally by the RFID sensors 405, or read and used by the control unit 420, to discern relative environmental information to which the RFID sensors 405 are exposed. In some instances, the RFID sensors 405 may contain a calibrated look-up-table within the memory storage device 430 of integrated circuit 425, which may be accessed to determine the relevant environmental information. Additionally or alternatively, the RFID reader 415 may issue commands to retrieve the digital representations of the energy state contained in integrated circuit 425 (e.g., a quantitative impedance value stored in memory storage device 430), and the control unit 420 may use the retrieved digital representations to evaluate the environment to which the RFID sensors 405 are exposed. The evaluation could be as simple as referencing fixed data in memory that has already been stored and calibrated, or as complex as a software application running on the reader or its connected systems for performing interpretive evaluations. Thus, the combining of the technologies enables a user to sense the environment to which the RFID sensors 405 are exposed as well as sense changes to that same environment.

In some instances, the RFID sensors 405 of FIG. 4A may be deployed as an array of smart sensors or agents to collect data that may be sent back to a IoT device 410. For example, a series of RFID sensors 405 may be deployed where each sensor 405 has a unique identification number stored within the memory storage device 430 that can be communicated via the internal wireless communications module 440 to the control unit 420 of the IoT device 410. The RFID reader 415 may issue a command to the RFID sensors 405 to activate integrated circuit 425 and/or detector 445 and, subsequent to the respective operations of integrated circuit 425 and/or detector 445, receive the unique identification number and the digital representations of the energy state (e.g., a quantitative impedance value). The control unit 420 of the IoT device 410 may then communicate the unique identification number, digital representations of the energy state, and any evaluation results to a remote data processing unit 455 (e.g., a cloud network 140 or client device 105 as described with respect to FIG. 1) for further processing or analysis. Thus, the sensor array may allow information to be sensed and communicated to the RFID reader 415, and this information may be pre-processed at the RFID sensor 415, and/or remotely processed at the control unit 420 of the IoT device 410 and/or the remote data processing unit 450 depending on the system needs.

As should be understood, the IoT device 410 should be placed within a predetermined distance of the RFID sensors 405 in order to facilitate and maintain wireless communication. The maximum distance achievable between the IoT device 410 and the RFID sensors 405 is influenced by a number of factors including operating frequency, settings or parameters of the IoT device 410, the antennas of the IoT device 410 and the RFID sensors 405, characteristics of the RFID sensors 405, material used to attach the RFID sensor, environment the RFID solution is being used in, and the like. In general, Low Frequency (LF) Passive RFID tags have a maximum read distance of 30 cm (1 foot) or less, High Frequency (HF) Passive RFID tags have a maximum read distance of 1.5 meters (4 foot 11 inches), and Ultra High Frequency (UHF) Passive RFID tags have a maximum read distance of over 16 meters or 52 feet.

Figure 4B:
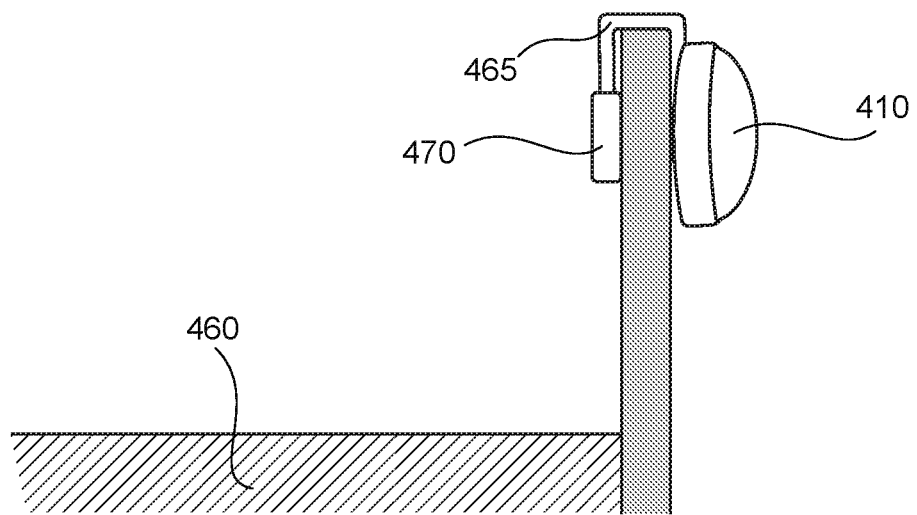
FIGS. 4B and 4C show an IoT device and exemplary placement of the IoT device on the bed of a subject in accordance with various embodiments.
Figure 4C:
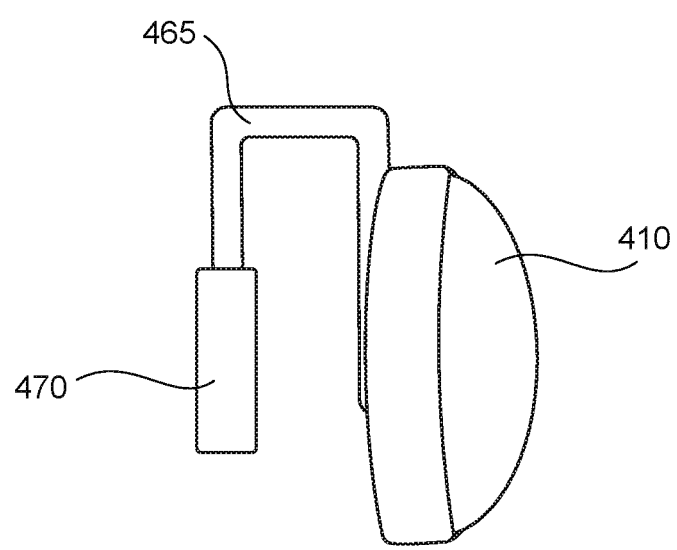

In various instances, the IoT device 410 is placed in the same room in which the RFID sensors 405 are to be primarily used (e.g., a bedroom or hospital bed room) such that the IoT device 410 is within a predetermined distance of the RFID sensors 405. The IoT device 410 could be placed in multiple positions within the room including the bedspring or frame beneath the patient, on the floor beneath the bed, on the night stand, on a dresser, or on the ceiling. FIGS. 4B and 4C show an IoT device 410 and exemplary placement of the IoT device 410 on the bed 460 of a subject in accordance with various embodiments. For example, the IoT device 410 could be attached to a first end of an angled bracket 465 which overlies the foot board of the bed 460. This would allow for an external antenna 470 connected with the IoT device 410 to be attached to a second end of the angled bracket 465, which can then be optimally directed toward the RFID sensors 405. The angled bracket 460 have an adjustable goose neck or multi-angled structure to facilitate customization of the external antenna 470 and the RFID sensors 405 interface angle.

In other instances, the RFID sensors 405 and the IoT device 410 are constructed to create a wearable such that the IoT device 410 is maintained within a predetermined distance of the RFID sensors 405 as a subject moves through the environment. This arrangement may comprise a stacked or single data board (i.e., printed circuit board) containing the RFID reader 415 and the control unit 420. The control unit 420 could be used to provide the processing for the RFID reader 415 as compared to an alternate solution in which the RFID reader 415 and the control unit 420 use separate chips (e.g., in the room or bed embodiment in which there is greater footprint available within the IoT device 410 for multiple processing chips). The power supply for the wearable could be based on a rechargeable lithium battery but other power sources could include solar, body movement (triboelectric charging, and piezoelectric charging). Other alternatives may include charging from a wheel chair movement with rotation of the wheels powering a dynamo or a magneto with or without a rectifier to charge an onboard battery or capacitor storage device.

In some embodiments, the wireless solution 400 uses energy state changes in the RFID sensor data over time rather than the absolute energy state of the RFID sensor data to determine one or more types of activity, events, or parameters such as undergarment or absorbent pad capacity. Undergarment and absorbent pad technology relies on the presence of an absorbent material comprising a nonwoven absorbent core and a superabsorbent polymer (SAP)), which responds to moisture by initially undergoing a wetting phase followed by a wicking phase. This wicking phase is manifested by the capillary action of the nonwoven material and the liquid being absorbed by the SAP. The initial response to wetting of a standard volume is absorbency at a near linear rate of weight per time followed by a decrease in slope as equilibrium and maximal capacity is reached. This indication of capacity occurs at the shoulder of the slope. If a wetting event occurs which is not at undergarment or absorbent pad capacity, absorbency of liquid occurs and follows a linear rate and depending on the location of wetting in the diaper, drying occurs as the capillary movement distributes moisture throughout the undergarment or absorbent pad. That is, there is a transit and redistribution of moisture throughout the undergarment or absorbent pad. The wireless solution 400 can exploit this dynamic alteration in the absorbance over time to determine capacity of the undergarment or absorbent pad. Specifically, the varying energy state that the RFID sensor detects correlates with dynamic movement and redistribution of liquid within the undergarment or absorbent pad which occurs up until full capacity is reached. Once full capacity is reached, saturation occurs, and the undergarment or absorbent pad is at risk for leaking. This is manifested by a static energy state measured at the periphery of the undergarment or absorbent pad or complete loss of RFID signal as the liquid front obstructs the RFID antenna consistent with full peripheral diaper capacity. The wireless solution 400 can measure the varying energy state that the RFID sensor detects and the decreased signal variation or loss of signal and records it as an event indication for undergarment or absorbent pad capacity (e.g., unsaturated or saturated).

FIGS. 5A-5F illustrate a wireless system 500 for detecting various energy states where one or more sensors 505a-n (e.g., the UHF sensors, passive or active RFID sensors, or the like discussed with respect to FIGS. 3 and 4) are disposed on a device 510 (e.g., an undergarment or absorbent pad) individually or as an array in various arrangements/patterns to obtain relevant environmental information. In some embodiments, the wireless system 500 comprises at least one sensor 505a disposed on the liquid impermeable back sheet at the interface between the underlying absorbent material 512 and the non-absorbent material 514, and at least one sensor 505b disposed on the liquid impermeable back sheet at the outer margin of the non-absorbent material 514 (an area of the device 510 that is not over the absorbent material 512). The measurement by sensor 505b at the outer margin will be a leading indicator of maximal capacity and, with saturation, will reach a steady state; whereas measurement by sensor 505a at the absorbent material interface will be a leading indicator of the start of a wetting event, a drying event, and/or an unsaturated absorbent material. The change in energy state over time represents the rate of wetting and drying using a capillary model. As this energy state reaches an equilibrium number, this will correlate with device saturation. The wireless system 500 can be adjusted to detect either a single episode of incontinence or multiple episodes of incontinence. Moreover, the wireless system 500 is capable of detecting single wetting episodes as well as the device saturation state following one or more episodes of wetting. In certain instances, active control of another medical device such as a IV pump or g tube pump could be activated in response to analytics obtains from evaluating a subject's hydration state via system 500.

Figure 5A:
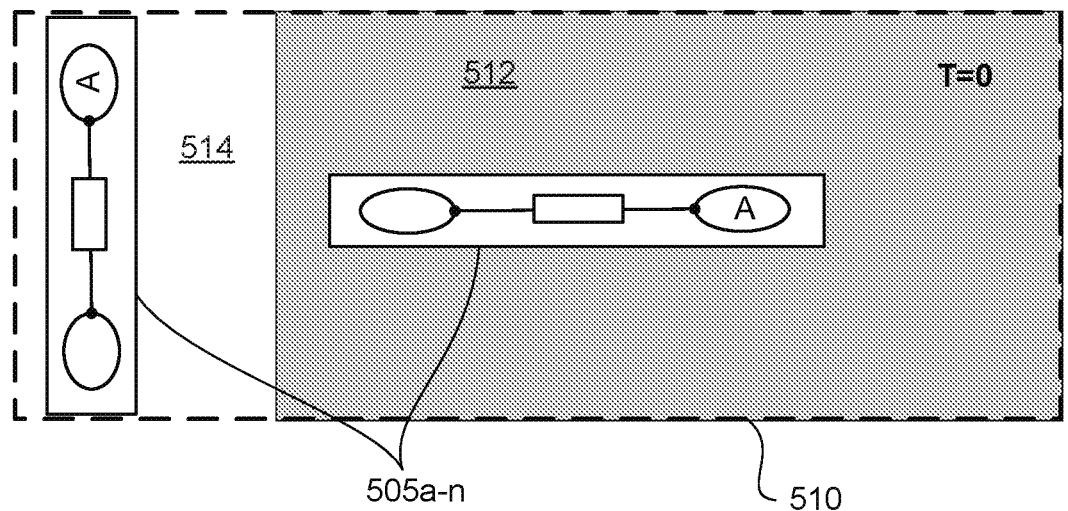
FIGS. 5A-5F show a wireless solution and sensor arrangement for a medical device in accordance with various embodiments.
Figure 5B:
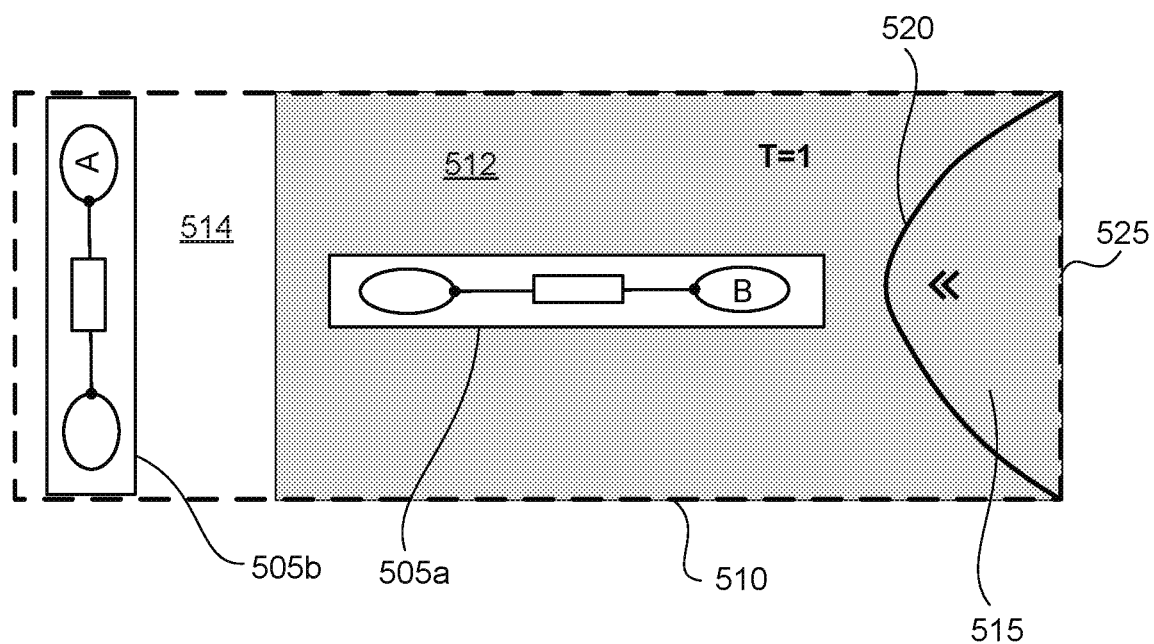

As discussed herein, the one or more sensors 505a-n are capable of taking various energy states dependent on the amount of moisture present in the environment. As shown in FIG. 5A, at dry conditions or normalized conditions for the environment (Time (T)=0) the sensors 505a-n may detect a first energy state at equilibrium (digital representation value=A). As shown in FIG. 5B, upon a first moisture event 515 (T=1), as a moisture front 520 moves from an initial contact 525 point on device 510 towards the sensors 505a-b, the sensor 505a may detected a second energy state (digital representation=B, where B is different from A) indicative of an initial moisture change in the environment. The change from energy state A to energy state B may be communicated to the IoT device (not shown) and used by the sensor 505a or the IoT device to obtain relevant environmental information. For example, if the change from energy state A to B is greater than a predetermined threshold, then the change may be determined to be indicative of a start time for an incontinent event. Alternatively, if the energy state B is greater than a predetermined threshold, then the energy state B may be determined to be indicative of a start time for an incontinent event.

Figure 5C:
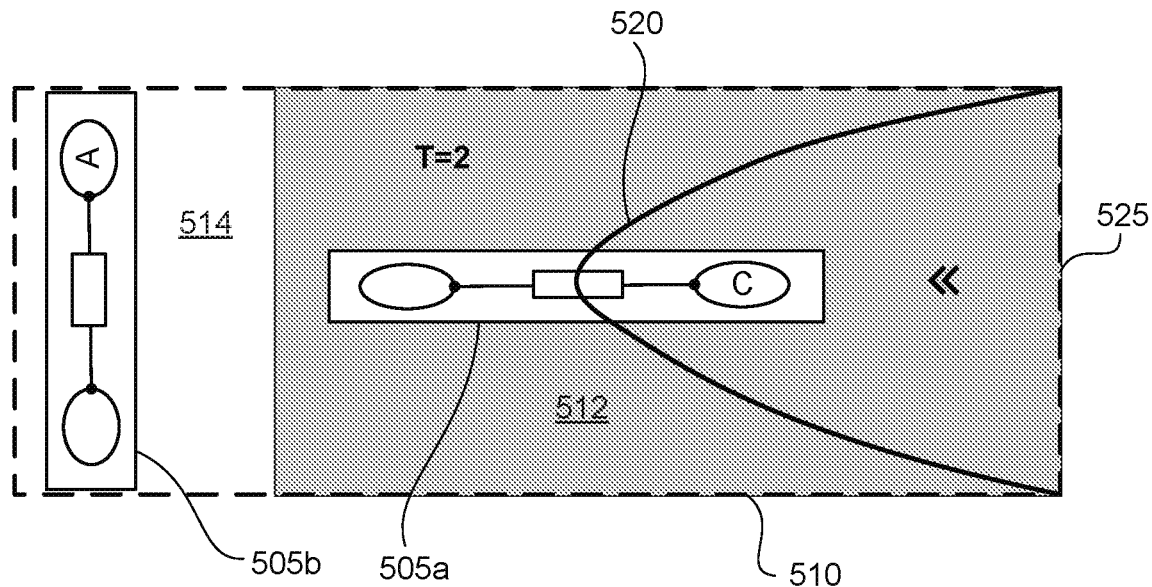

As shown in FIG. 5C, as the moisture front 520 moves from the initial contact 525 point across the sensor 505a, the sensor 505a may detected a third energy state (digital representation=C, where C is different from A and B) indicative of a progressive moisture change in the environment. The change from energy state B to energy state C may be communicated to the IoT device (not shown) and used by the sensor 505a or the IoT device to obtain further relevant environmental information. For example, if the change from energy state B to C is greater than a predetermined threshold, then the change may be determined to be indicative of continuation of the incontinent event. Alternatively, if the energy state C is greater than a predetermined threshold, then the energy state C may be determined to be indicative of a continuation of the incontinent event. In some instances, the energy states A, B, and C at T=0-2, respectively, can be used to approximate a volume of liquid (e.g., urine) excreted from a subject.

Figure 5D:
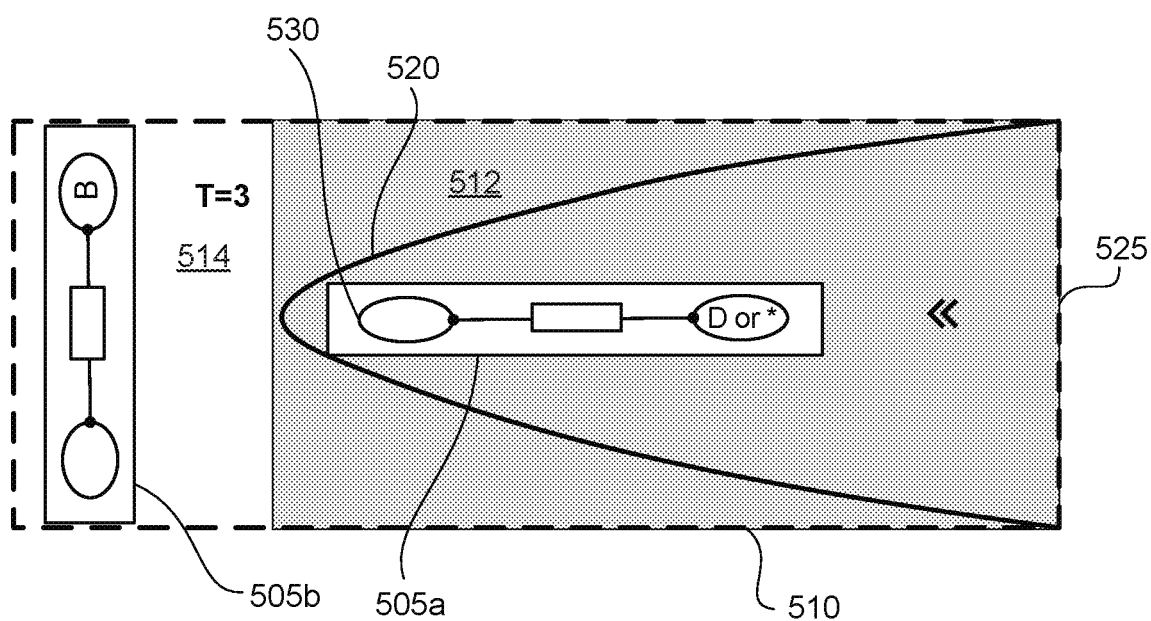

As shown in FIG. 5D, as the moisture front 520 moves from the initial contact 525 point across the sensor 505a towards the sensor 505b, the sensor 505a may detected a fourth energy state (digital representation=D, where D is different from A, B and C) indicative of a progressive moisture change in the environment. The change from energy state C to energy state D may be communicated to the IoT device (not shown) and used by the sensor 505a or the IoT device to obtain further relevant environmental information. For example, if the change from energy state C to D is greater than a predetermined threshold, then the change may be determined to be indicative of continuation of the incontinent event. Alternatively, if the energy state D is greater than a predetermined threshold, then the energy state D may be determined to be indicative of a continuation of the incontinent event. In some instances, the energy states A, B, C and D at T=0-3, respectively, can be used to approximate a volume of liquid (e.g., urine) excreted from a subject. Additionally, as the moisture front 520 moves towards the sensor 505b, the sensor 505b may detected the second energy state (digital representation=B, where B is different from A) indicative of an initial moisture change in the environment. The change from energy state A to energy state B may be communicated to the IoT device (not shown) and used by the sensor 505b or the IoT device to obtain relevant environmental information. For example, if the change from energy state A to B is greater than a predetermined threshold, then the change may be determined to be indicative of a progressive moisture change in the environment (given the identity and location of the sensor 505b relative to the sensor 505a and initial contact 525 point). Alternatively, if the energy state B is greater than a predetermined threshold, then the energy state B may be determined to be indicative of a progressive moisture change in the environment (given the identity and location of the sensor 505b relative to the sensor 505a and initial contact 525 point). In some instances, the energy states A and B from the sensor 505b and the energy states C and D from the sensor 505b at T=2 and T=3, respectively, can be used to approximate a volume of liquid (e.g., urine) excreted from a subject.

Alternatively, as the moisture front 520 moves from the initial contact 525 point across the sensor 505a towards the sensor 505b, the sensor 505a may stop reporting energy states (loss of single or energy state *). In some instances, the sensors 505a-n may stop reporting energy states when the moisture front 520 passes over the antenna 530 (essentially complete loss of RFID signal as the liquid front obstructs the RFID antenna and prevents communication of the sensor data). The loss of communicable sensor data may be recognized by the IoT device (not shown) and used by the IoT device to obtain further relevant environmental information. For example, loss of communicable sensor data may be determined to be indicative of continuation of the incontinent event. In some instances, the energy states A, B, and C at T=0-2, respectively, and loss of communicable sensor data at T=3 can be used to approximate a volume of liquid (e.g., urine) excreted from a subject. Additionally, as the moisture front 520 moves towards the sensor 505b, the sensor 505b may detect the second energy state (digital representation=B, where B is different from A) indicative of an initial moisture change in the environment. The change from energy state A to energy state B may be communicated to the IoT device (not shown) and used by the sensor 505b or the IoT device to obtain relevant environmental information. For example, if the change from energy state A to B is greater than a predetermined threshold, then the change may be determined to be indicative of a progressive moisture change in the environment (given the loss of sensor data from the sensor 505a and the identity and location of the sensor 505b relative to the sensor 505a and initial contact 525 point). Alternatively, if the energy state B is greater than a predetermined threshold, then the energy state B may be determined to be indicative of a progressive moisture change in the environment (given the loss of sensor data from the sensor 505a and the identity and location of the sensor 505b relative to the sensor 505a and initial contact 525 point). In some instances, the energy states A and B from the sensor 505b and energy states A, B, and C and loss of communicable sensor data from the sensor 505a at T=0-3, respectively, can be used to approximate a volume of liquid (e.g., urine) excreted from a subject.

Figure 5E:
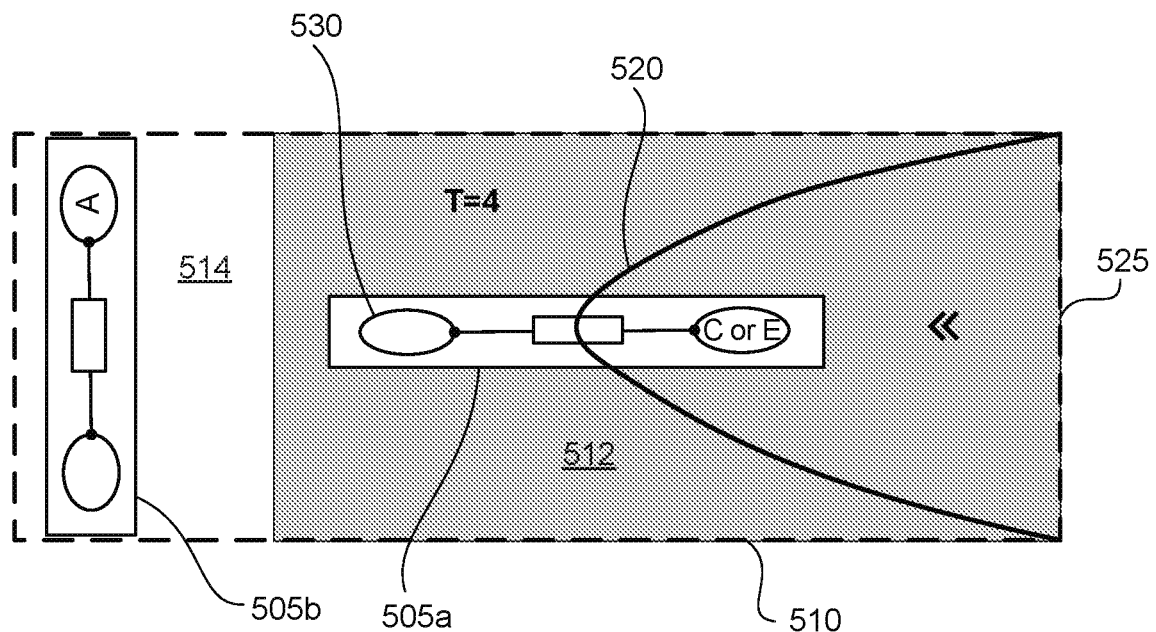

As shown in FIG. 5E, in certain instances after a certain amount of time (T=4), the moisture front 520 may recede back across the sensor 505a towards the initial point of contact, where the sensor 505a may detected a return to the third energy state (digital representation=C) or a fifth energy state (digital representation=E, where E is different from A, B and D, and different from C) indicative of a drying or adsorption event in the environment. The change from energy state D to energy state C or E may be communicated to the IoT device (not shown) and used by the sensor 505a or the IoT device to obtain further relevant environmental information. For example, if the change from energy state D to C or E is less than a predetermined threshold, then the change may be determined to be indicative of the end of an incontinent event and subsequent drying or absorption of the moisture. Alternatively, if the energy state C or E is less than a predetermined threshold, then the energy state C or E may be determined to be indicative of the end of an incontinent event and subsequent drying or absorption of the moisture. In some instances, a temporal component can be used in conjunction with the energy state or change in energy state to determine subsequent drying or absorption of the moisture. For example, if the change from energy state D to C or E is less than a predetermined threshold and occurs with a period of time that does not exceed a predetermined temporal threshold, then the change may be determined to be indicative of the end of an incontinent event and subsequent drying or absorption of the moisture. Alternatively, if the energy state C or E is less than a predetermined threshold and occurs with a period of time that does not exceed a predetermined temporal threshold, then the energy state C or E may be determined to be indicative of the end of an incontinent event and subsequent drying or absorption of the moisture. In some instances, the variation in energy states D and (C or E) at T=3 and T=4, respectively, can be used to determine that the absorbent material has not become saturated (i.e., capable of holding more moisture).

Additionally, as the moisture front 520 moves away from the sensor 505b, the sensor 505b may detect a return to the first energy state (digital representation=A) indicative of dry conditions or normalized conditions for the environment. The change from energy state B to energy state A may be communicated to the IoT device (not shown) and used by the sensor 505b or the IoT device to obtain relevant environmental information. For example, if the change from energy state B to A is less than a predetermined threshold, then the change may be determined to be indicative of the end of an incontinent event and subsequent drying or absorption of the moisture. Alternatively, if the energy state A is less than a predetermined threshold, then the energy state A may be determined to be indicative of the end of an incontinent event and subsequent drying or absorption of the moisture. In some instances, the variation in energy states A and B from the sensor 505b and the energy states D and (C or E) from the sensor 505b at T=3 and T=4 (optionally in accordance with a temporal component), respectively can be used to determine that the absorbent material has not become saturated (i.e., capable of holding more moisture).

Alternatively, as the moisture front 520 recedes back across the sensor 505a towards the initial point of contact, the sensor 505a may re-start reporting energy states when the moisture front 520 recedes from being in contact with the antenna 530 (essentially allowing antenna communication of the sensor data). The re-start of communicable sensor data (e.g., a return to the third energy state (digital representation=C) or a fifth energy state (digital representation=E, where E is different from A, B and D, and different from C) may be recognized by the IoT device (not shown) and used by the IoT device to obtain further relevant environmental information. For example, re-start of communicable sensor data may be determined to be indicative of a drying or adsorption event in the environment. In some instances, a temporal component can be used in conjunction with the re-start of communicable sensor data to determine subsequent drying or absorption of the moisture. For example, if the re-start of communicable sensor data occurs within a period of time that does not exceed a predetermined temporal threshold, then the change may be determined to be indicative of the end of an incontinent event and subsequent drying or absorption of the moisture. In some instances, the energy state D and (C or E) and re-start of communicable sensor data at T=3 and T=4, respectively, can be used to determine that the absorbent material has not become saturated (i.e., capable of holding more moisture).

Additionally, as the moisture front 520 moves away from the sensor 505b, the sensor 505b may detect a return to the first energy state (digital representation=A) indicative of dry conditions or normalized conditions for the environment. The change from energy state B to energy state A may be communicated to the IoT device (not shown) and used by the sensor 505b or the IoT device to obtain relevant environmental information. For example, if the change from energy state B to A is less than a predetermined threshold, then the change may be determined to be indicative of the end of an incontinent event and subsequent drying or absorption of the moisture. Alternatively, if the energy state A is less than a predetermined threshold, then the energy state A may be determined to be indicative of the end of an incontinent event and subsequent drying or absorption of the moisture. In some instances, the energy states A and B from the sensor 505*b* and the energy states D and (C or E) and re-start of communicable sensor data from the sensor 505*b* at T=3 and T=4 (optionally in accordance with a temporal component), respectively, can be used to determine that the absorbent material has not become saturated (i.e., capable of holding more moisture).

Figure 5F:
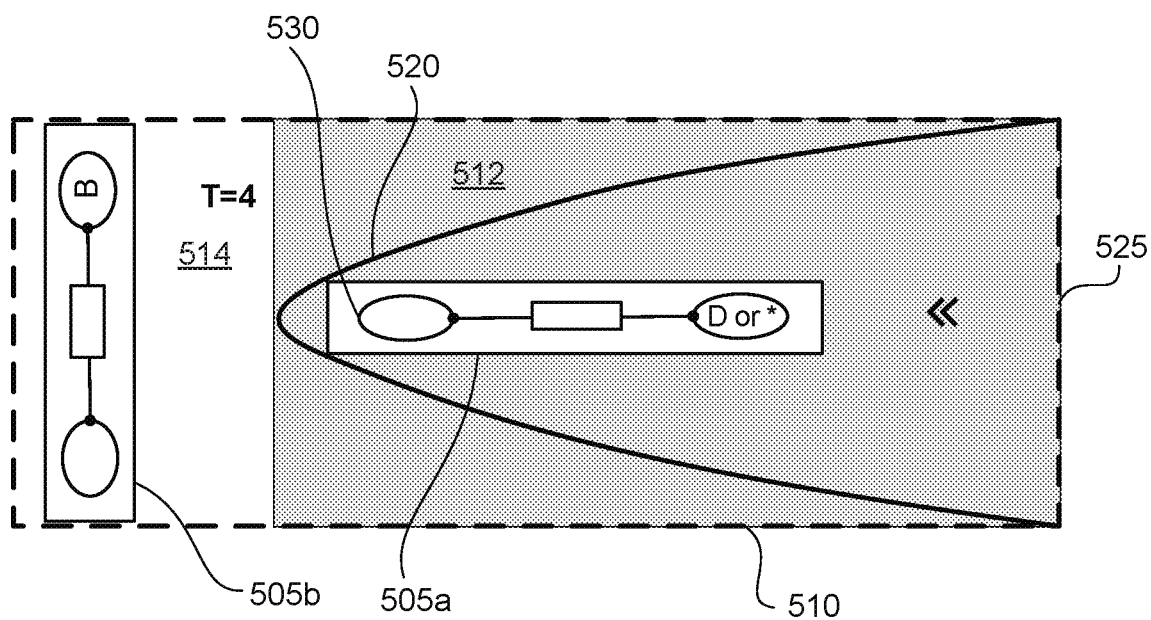

As shown in FIG. 5F, in certain instances after a certain amount of time (T=4), the moisture front 520 may remain the same (e.g., reach equilibrium), where the sensor 505*a* continues to detect the fourth energy state (digital representation=D) indicative of a steady state of moisture in the environment. The steady energy state D may be communicated to the IoT device (not shown) and used by the sensor 505*a* or the IoT device to obtain further relevant environmental information. For example, if the energy state D has not change for a period of time (T=4) that is greater than a predetermined threshold, then the absence of a change in energy state may be determined to be indicative of a steady state of moisture in the environment. In some instances, the energy states C and D at T=2, T=3, and T=4 (optionally in accordance with a temporal component), respectively, can be used to determine that the absorbent material has become saturated (i.e., not capable of holding any more moisture). Additionally, when the moisture front 520 remains the same, the sensor 505*b* may continue to detect the second energy state (digital representation=B) indicative of a steady state of moisture in the environment. The steady energy state B may be communicated to the IoT device (not shown) and used by the sensor 505*b* or the IoT device to obtain further relevant environmental information. For example, if the energy states B and D have not changed for a period of time (T=4) that is greater than a predetermined threshold, then absence of a change in energy state may be determined to be indicative of a steady state of moisture in the environment. In some instances, the energy states B, C and D at T=2, T=3, and T=4 (optionally in accordance with a temporal component), respectively, can be used to determine that the absorbent material has become saturated (i.e., not capable of holding any more moisture).

Alternatively, in certain instances after a certain amount of time (T=4), the moisture front 520 may remain the same (e.g., reach equilibrium), where the sensor 505*a* continues to not repot energy states (energy state *). The loss of communicable sensor data for a period time may be recognized by the IoT device (not shown) and used by the IoT device to obtain further relevant environmental information. For example, if the loss of communicable sensor data has continued for a period of time (T=4) that is greater than a predetermined threshold, then loss of communicable sensor data may be determined to be indicative of a steady state of moisture in the environment. In some instances, the energy states C and * at T=2, T=3, and T=4 (optionally in accordance with a temporal component), respectively, can be used to determine that the absorbent material has become saturated (i.e., not capable of holding any more moisture). Additionally, when the moisture front 520 remains the same, the sensor 505*b* may continue to detect the second energy state (digital representation=B) indicative of a steady state of moisture in the environment. The steady energy state B may be communicated to the IoT device (not shown) and used by the sensor 505*b* or the IoT device to obtain further relevant environmental information. For example, if the energy states B and * have not changed for a period of time (T=4) that is greater than a predetermined threshold, then absence of a change in energy state may be determined to be indicative of a steady state of moisture in the environment. In some instances, the energy states B, C and * at T=2, T=3, and T=4 (optionally in accordance with a temporal component), respectively, can be used to determine that the absorbent material has become saturated (i.e., not capable of holding any more moisture).

It should be appreciated that although FIGS. 5A-5F illustrate a technique to monitor urinary incontinence of one or more subjects using an arrangement of two sensors, the technique can be implemented using any number and arrangement of sensors. For example, this technique can be implemented where multiple sensors are disposed on the liquid impermeable back sheet over the underlying absorbent pad in an array. This arrangement may be useful in an instance in which a finer grain of detail is necessary in the detection of various energy states (e.g., detection of patterns from numerous incontinent events absorbed by a single device). Additionally or alternatively, multiple sensors are disposed on the liquid impermeable back sheet at the outer margin of the non-absorbent material such that it is unlikely the sensor ever becomes wet and potentially stops reporting energy states (energy state *). This arrangement may be useful in an instance in which the movement of a subject is to be continuously monitored.

FIGS. 6A-6E illustrate another wireless system 600 for detecting various energy states where one or more sensors 605*a-n* (e.g., passive or active RFID sensors, or the like discussed with respect to FIGS. 3 and 4) are disposed on a device 610 (e.g., a Foley bag) as a linear array to obtain relevant fluid volume information. In some instances, the fluid output (e.g., urine output) can be recorded via the device 610 such as a fluid collection device or wall suction unit attached to the subject either through a condom catheter (male), wicking device (female) or catheter. This device 610 could be used to record fluid volume over time via a sequence of aligned RFID sensors. The RFID sensors could be either specific moisture sensing tags relying on an alteration in the energy state of the tag when closely associated with liquid, or a standard tag which loses signal as liquid is in close relationship or blocking the antenna. This alteration in signal or loss of signal can then be used to determine volume over time information. In certain instances, active control of another medical device such as a IV pump or g tube pump connected with an IoT device could be activated in response to analytics obtains from evaluating a subject's hydration state via system 600.

Figure 6A:
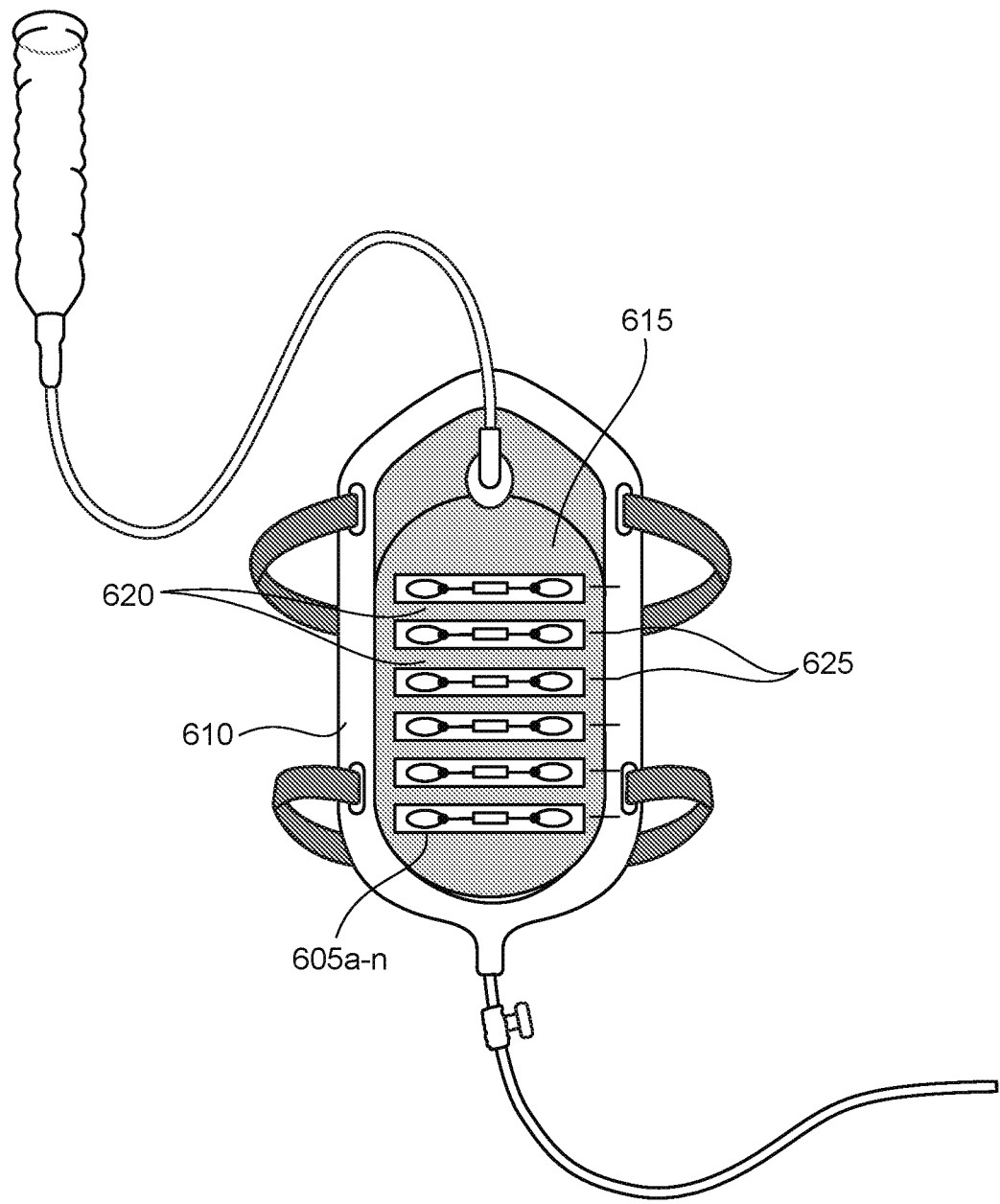
FIGS. 6A-6E show another wireless solution and sensor arrangement for a medical device in accordance with various embodiments.
Figure 6B:
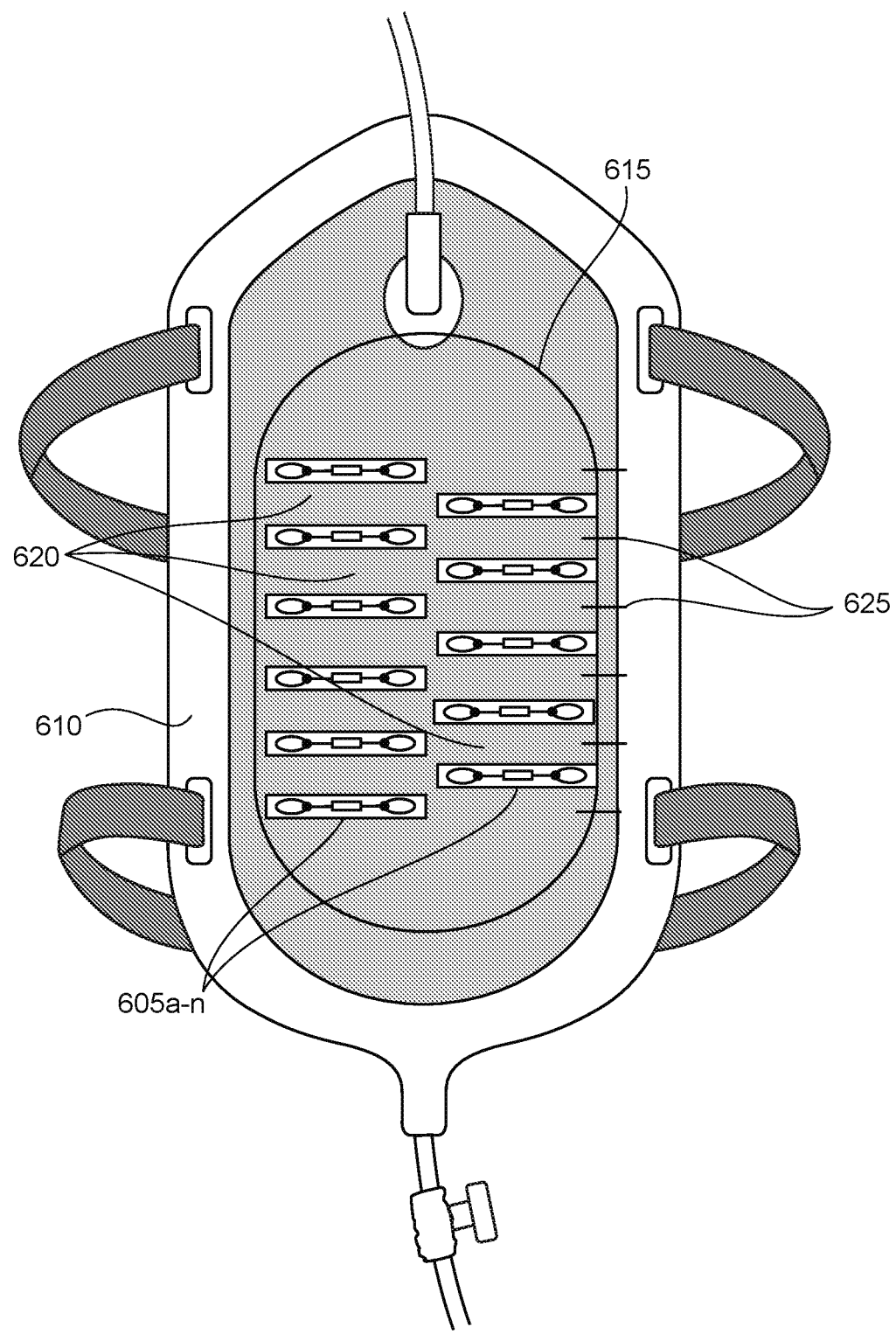

As shown in FIG. 6A, the one or more sensors 605*a-n* are disposed on a substrate 615 (e.g., a polymer or paper product) with an adhesive or other attachment medium or structure for attachment to the device 610. As discussed herein, the one or more sensors 605*a-n* are capable of taking various energy states dependent on the amount of moisture present in the environment. The external application of the one or more sensors 605*a-n* would allow the retrofitting of an existing device 610. In other embodiments, the one or more sensors 605*a-n* are incorporated directly into the manufacture of the device 610 such that an adhesive external substrate would not be required. In either instance, the sensors 605*a-n* are disposed on the device 610 at regular intervals 620 to match respective device volume intervals 625. Additionally, multiple linear arrays of the one or more sensors 605a-n can be attached to the device 610. For example, two or more linear arrays of the one or more sensors 605a-n can be attached to the device 610 in an offset parallel pattern (see, e.g., FIG. 6B). This would achieve increased precision of volume measurement when needed without requiring a separate higher density linear array of sensors 605a-n. Exemplary medical volume measurements that would be suitable for this solution would include urine volume, nasogastric output volume, chest tube volume, intravenous fluid outputs, and gastric tube feed outputs.

Figure 6C:
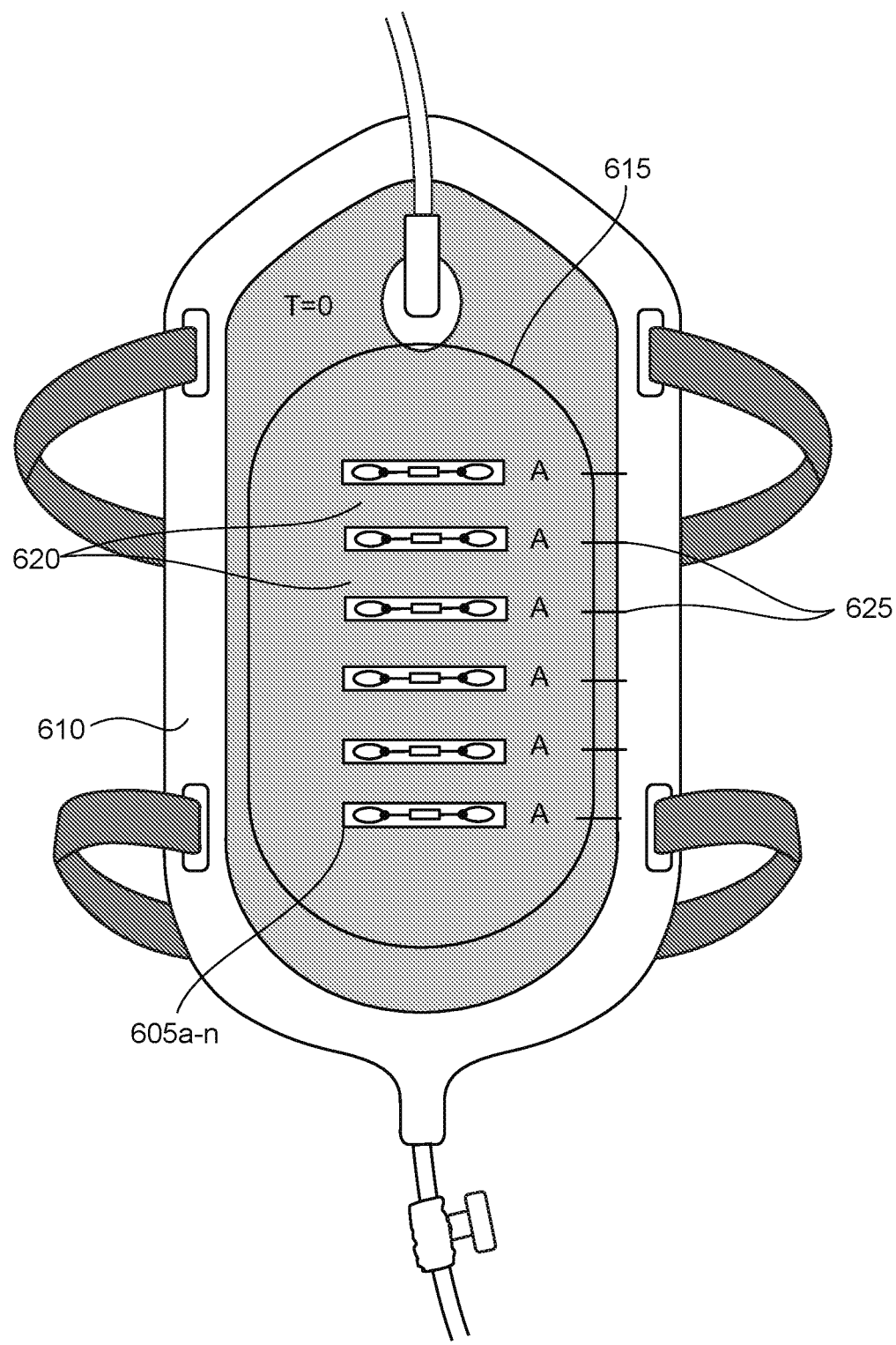
Figure 6D:
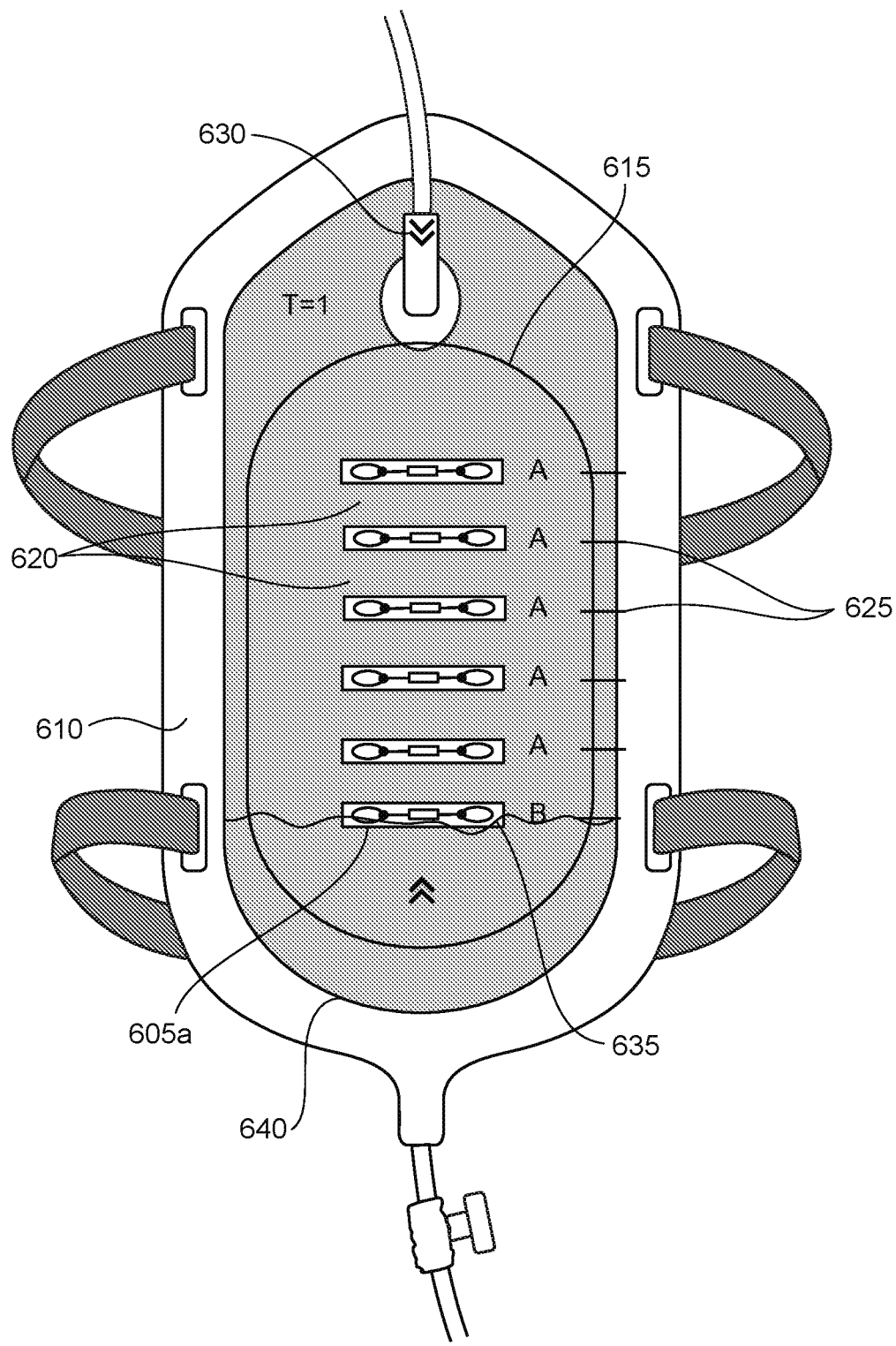

As shown in FIG. 6C, at dry conditions or normalized conditions for the environment (Time (T)=0) the sensors 605a-n may detect a first energy state (digital representation value=A). As shown in FIG. 6D, upon a first moisture event 630 (T=1), as a moisture front 635 moves from an initial holding 640 point within device 610 towards the sensors 605a-b, the sensor 605a may detected a second energy state (digital representation=B, where B is different from A) indicative of an initial moisture change in the environment. The change from energy state A to energy state B may be communicated to the IoT device (not shown) and used by the sensor 605a or the IoT device to obtain relevant environmental information. For example, if the change from energy state A to B is greater than a predetermined threshold, then the change may be determined to be indicative of a start time for an incontinent event. Additionally or alternatively, volume measurements could be calculated based on the unique identifier of the sensor 605a, its corresponding change in energy state from A to B, and knowledge of device volume intervals 625 corresponding to each of the sensors 605a-n (e.g., the device volume intervals may be stored in a table of a memory storage device), as well as volume over time measurements and volume per kg measurements. In some instances, data analytics regarding the patients' hydration state (for urine volume data) could be automated via logic or one or more prediction models in order to generate patient alerts in the patients' medical records.

Figure 6E:
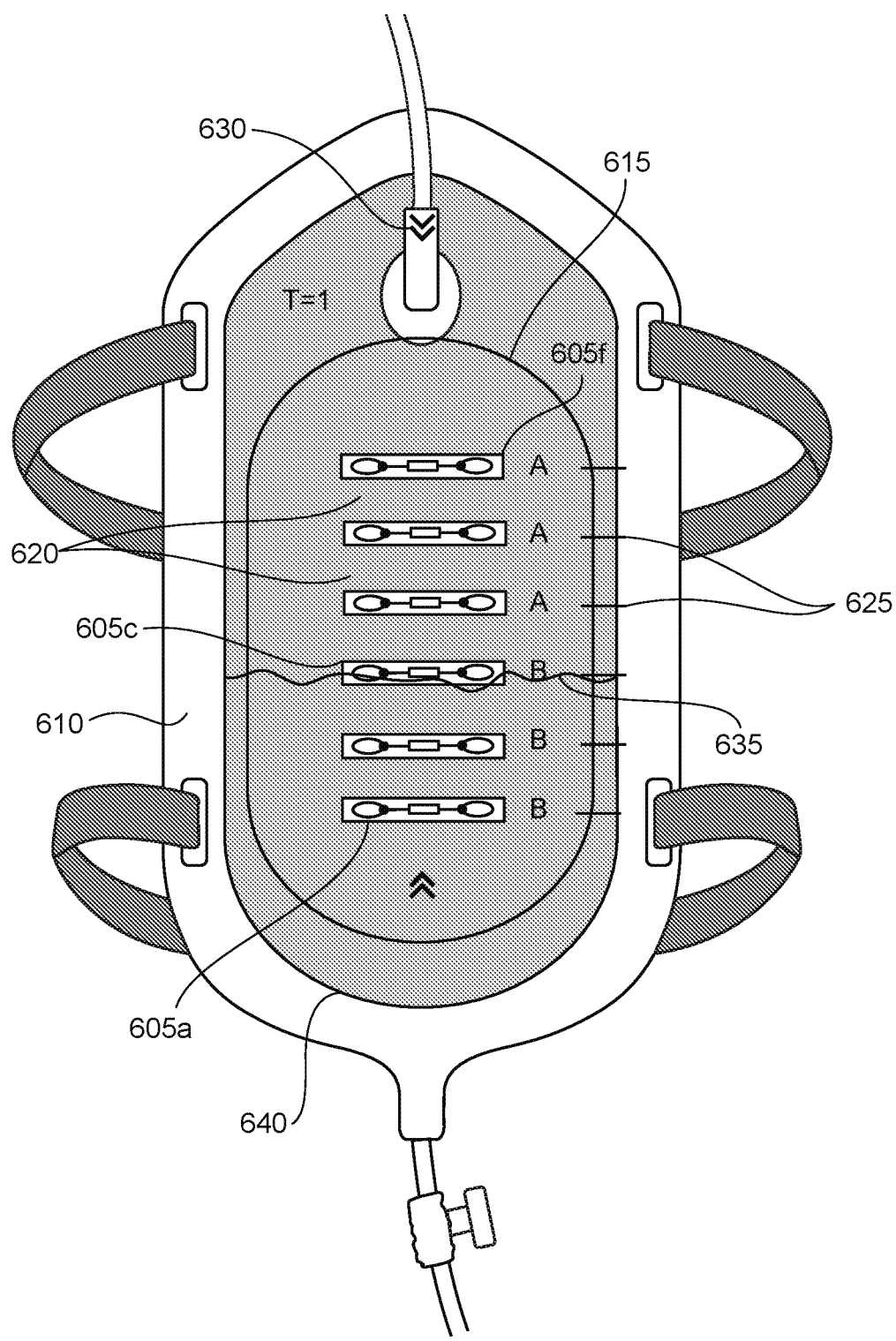

As shown in FIG. 6E, upon continuation of the first moisture event 615 or subsequent moisture events (T=2, 3, 4, etc.), as the moisture front 630 moves from the initial holding 635 point within device 610 towards the sensors 605b-n, the sensors 605b-n (e.g., sensor 605c and 605f) may detect the first energy state (digital representation=B, where B is different from A) indicative of an initial moisture change in the environment. The change from energy state A to energy state B may be communicated to the IoT device (not shown) and used by the sensors 605b-n or the IoT device to obtain relevant environmental information. For example, if the change from energy state A to B for sensor 605f is greater than a predetermined threshold, then the change may be determined to be indicative of a need to drain or change the device 610. Additionally or alternatively, further volume measurements could be calculated based on the unique identifier of the sensors 605b-n, their corresponding change in energy state from A to B, and knowledge of device volume intervals 625 corresponding to each of the sensors 605b-n (e.g., the device volume intervals may be stored in a table of a memory storage device), as well as volume over time measurements and volume per kg measurements. In some instances, further data analytics regarding the patients' hydration state (for urine volume data) could be automated via logic or one or more prediction models in order to generate patient alerts in the patients' medical records.

It should be appreciated that although FIGS. 6A-6E illustrate techniques to monitor urinary excretion and volume of one or more subjects using a linear arrangement of multiple sensors, the techniques can be implemented using any number and arrangement of sensors and/or IoT devices for any other type of healthcare solution including Nasogastric tube and chest tube drainage output. For example, a single RFID sensor could be used to more simply determine when a device such as a Foley bag is full or needs to be drained or changed. Alternative to direct RFID measurements, a moisture sensing strip could be used with conductance capability manufactured within the device to determine volume. An external power source would then be used with resultant information directed to an attached IoT device or via a wireless connection to a IoT device. Another embodiment may employ a strain gauge attached directly to an IoT device or via wireless connectivity, which would then be used to upload these measurements to the cloud network. Either via edge computing or in the cloud network, the weight of the bag would be subtracted from these weights yielding liquid volume measurements This information could also be used to generate volume vs time measurements, which could be uploaded to the patient's electronic medical record.

It should also be appreciated that although FIGS. 6A-6E illustrate techniques directed to healthcare solutions, the techniques could be implemented in other industries. For example, an arrangement of multiple sensors (e.g., linear) can be implemented using any number and arrangement of sensors and/or IoT devices solutions for industrial measurements of a liquid within a tank or other containment unit (e.g., fuel level). The techniques could be employed when the tank is opaque or when it is not being monitored by direct physical inspection. Other applications for the techniques described herein may include the monitoring of a liquid leak within a containment system such as a containment pipe (e.g., an HVAC condensation or drip pipe) or directly into surrounding soil or directly penetrating through a transport system or pipe with drainage into the surrounding environment.

IV. Logic and Machine Learning Based Techniques for Measuring and Tracking Metrics of Subject's Health or Wellbeing In various embodiments, techniques are provided to measure and track metrics of a subjects health or wellbeing based on data obtained from sensors and IoT devices. The data may be collected and analyzed using a management platform and system, as described with respect to FIGS. 1 and 2. Thus, data may be captured more frequently from multiple sensors and IoT devices and more accurately as compared to observations that rely on human eyes. Further, many different types of sensors and IoT devices can be used to provide the data, including moisture sensors, pressure sensors, weight or temperature sensors, medical devices in communication with IoT devices, security cameras, web cameras, and/or medical device sensors such as laboratory instruments used in a healthcare facility. Because techniques disclosed herein utilize data from a variety of sources, the techniques provided herein allow for identification of a given subject and/or device from the data, such that analysis may be provided specific for the given subject and/or device and in some instances compared to other subjects and/or devices also identified within the data. These techniques are capable of providing, as a service, a consumable product such as a dashboard or interface capable of displaying and allowing for interaction with the health or wellbeing information such as a chart showing voiding intervals for one or more subjects along with the current incontinence status of one or more subjects.

Figure 7:
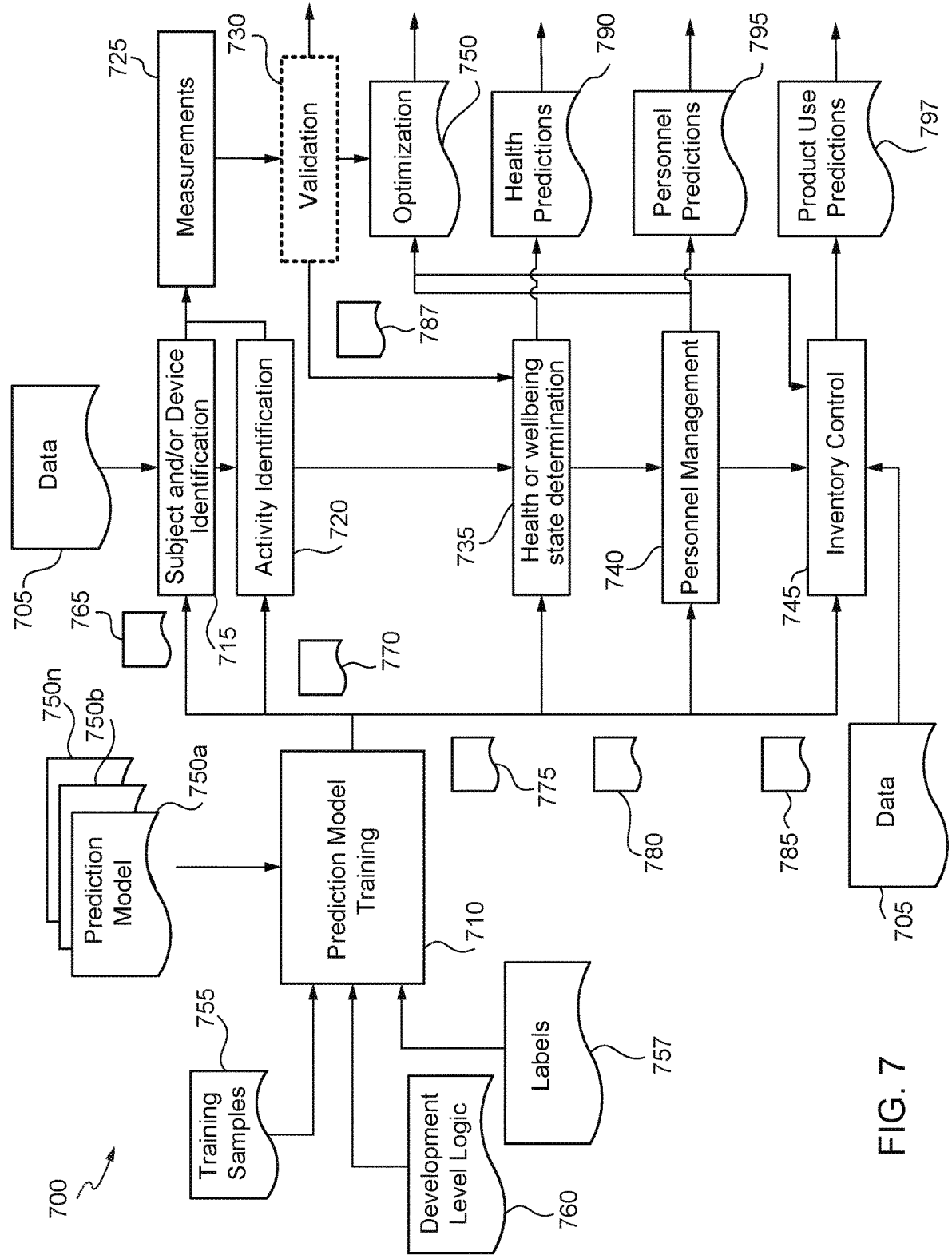
FIG. 7 shows an analysis system for training and running a machine learning network to analyze and track metrics of health and wellbeing in accordance with various embodiments.

FIG. 7 shows a block diagram illustrating aspects of a data analysis system 700 (e.g., the data analysis module 275 described with respect to FIG. 2) configured to measure and track metrics of a subject's health or wellbeing based on data 705 (e.g., sensor and/or IoT device data). As shown in FIG. 7, the health or wellbeing detection and analysis performed by the data analysis system 700 in this example include several stages: a prediction model training stage 710, a subject and/or device identification stage 715, an activity identification stage 720, a measurement determination stage 725, an optional validation stage 730, a health or wellbeing state determination stage 735, a personnel management evaluation stage 740, an inventory control stage 745, and a optimization prediction stage 750. The prediction model training stage 710 builds and trains one or more prediction models 750a-750n ('n' represents any natural number) to be used by the other stages (which may be referred to herein individually as a prediction model 750 or collectively as the prediction models 750). For example, the prediction models 750 can include a model for recognizing or identifying a specific subject or device from other subjects or devices, such as a subject or device of interest for measuring and tracking metrics. The prediction models 750 can also include a model for recognizing or identifying actions of one or more subjects, such as a excreting urine, getting out of bed, accessing a bathroom, entering a geofence area, or flipping over in bed. The prediction models 750 can also include a model for predicting a health or wellbeing of a subject. Still other types of prediction models may be implemented in other examples according to this disclosure.

A prediction model 750 can be a machine-learning ("ML") model, such as a convolutional neural network ("CNN"), e.g. an inception neural network, a residual neural network ("Resnet") or NASNET provided by GOOGLE LLC from MOUNTAIN VIEW, CALIFORNIA, a recurrent neural network, e.g., long short-term memory ("LSTM") models, gated recurrent units ("GRUs") models, or the like. A prediction model 750 can also be any other suitable ML model trained to predict subject presence, identity of a subject or device, or activities from sensor or IoT device data, such as a Naive Bayes model, a Logistic Regression model, a Random Forest model, a three-dimensional CNN ("3DCNN"), a dynamic time warping ("DTW") technique, a hidden Markov model ("HMM"), etc., or combinations of one or more of such techniques—e.g., CNN-HMM or MCNN (Multi-Scale Convolutional Neural Network). The data analysis system 700 may employ the same type of prediction model or different types of prediction models for identity, activity, and optimization predictions.

To train the various prediction models 750 in this example, training samples 755 for each prediction model 750 are generated. The training samples 755 for a specific prediction model 750 can include input sensor or IoT device data (or input features of sensor or IoT device data) and labels 757 corresponding to the input sensor or IoT device data (or input features). For example, for a prediction model 750 to be utilized to predict a subject at risk for early urinary tract infections, the input can include data from moisture sensors or IoT devices, determined measurements such as volume of urine excreted over time, or features determined from sensor or IoT device data such as detection on an incontinent event, and the labels 757 can include a frequency of urination and/or volume of urine extracted from data indicating the presence of urinary tract infection or a vector indicating probabilities the data indicate a urinary tract infection. Similarly, for a prediction model 750 to be utilized to identify activity such as a subject flipping or rolling over in bed based on sensor or IoT device data, the input can be the sensor or IoT device data itself or features extracted from the sensor or IoT device data and the labels 757 can include energy states showing whether the activity has occurred or not in the sensor or IoT device data.

In some instances, the training process includes iterative operations to find a set of parameters for the prediction model 750 that minimizes a loss function for the prediction models 750. Each iteration can involve finding a set of parameters for the prediction model 750 so that the value of the loss function using the set of parameters is smaller than the value of the loss function using another set of parameters in a previous iteration. The loss function can be constructed to measure the difference between the outputs predicted using the prediction models 750 and the labels 757 contained in the training samples 755. Once the set of parameters are identified, the prediction model 750 has been trained and can be utilized for prediction as designed.

In addition to the training samples 755, other information can also be employed to refine the training process of the prediction models 745. For example, sensor or IoT device information (e.g., a location of the sensor or IoT device), profile information (e.g., features of a subject or operating parameters of a medical device), or medical records (e.g., measured weight) can provide clues for predictions such as the health or wellbeing of a subject. For instance, a known IoT device may be placed in a subject's room. Sensor data received by the IoT device showing human activity in the area may indicate that the activity is likely from a subject previously identified to be associated with the room. In another example, medical records that include a subject's physical measurement taken by a health care provider can be used to confirm predicted health and wellbeing of the subject. In yet another example, the presence of certain healthcare works (e.g., a healthcare work with an RFID tag bracelet) can also be an indicator of certain activities. For example, a healthcare worker detected from the IoT device data can indicate that the healthcare worker has entered the room of a subject and in combination with moisture sensor data could be used as a predictor of a undergarment or absorbent pad about to be changed or checked.

Representative sensor or IoT device data can be marked with additional labels indicating their representativeness. During the training of identity, activity, and optimization prediction models 750, a higher weight can be assigned to a term of the loss function that corresponds to this representative data. As a result, the trained prediction models 750 can give more weights to input data that are similar to the representative data when predicting the identity, activity, and optimization. In addition, developmental logic 760 can be incorporated into the prediction model training stage 710 to ensure that the activities or optimization predicted by a prediction model 750 does not violate the activity or optimization logic 760. A subject's health or wellbeing generally has inherent logic. For example, the need to change a undergarment or absorbent pad typically only happens after a subject has had one or more incontinent events. The inherent logical relationship between these events can be exploited to facilitate the activity or optimization prediction.

According to some aspects of the disclosure presented herein, the logical relationships can be formulated as one or more constraints to the optimization problem discussed above for training the prediction models 750. A training loss function that penalizes the violation of the constraints can be built so that the training can take into account the relationship logic constraints. Alternatively, or additionally, structures, such as a directed graph, that describe the current features and the temporal dependencies of the prediction output can be used to adjust or refine the features and predictions of the prediction models 750. In an example implementation, features are extracted from current moisture sensor data and combined with features from previous moisture sensor data and later moisture sensor as indicated in the directed graph. Features generated in this way can inherently incorporate the temporal, and thus the logical, relationship between the sensor and IoT device data in the training samples 755. Accordingly, the prediction models 750 trained using these features can capture the logical relationships between the various metrics and health or being of a subject.

As should be understood, sensor and IoT device data such as moisture data are typically voluminous and can cover several hours or more. Obtaining the labels 757 in the training samples 755 may require manually reviewing this data, and may therefore be a time consuming task. As a result, may be impractical to label all the sensor and IoT device data and thus a large amount of data may remain unlabeled. This unlabeled data, which may be cheaper to acquire than the labelled data, can also be employed to train the prediction models 750. For example, for an unlabeled training sensor or IoT device data, the prediction model 750 can be applied to predict activity and/or optimizations. If the predicted activity or optimizations violates the inherent logic of health or wellbeing of the subject, this unlabeled data can be penalized by introducing a term in the loss function. That is, the unlabeled training data whose predicted activity and/or optimization violates the inherent logic of the health or wellbeing of a subject can be utilized to redefine the training loss function. As a result, in some instances, the training loss function can be a combination of labelled data, as discussed above, and developmental logic losses based on the unlabeled data.

If, on the other hand, the predicted activity and/or development level for an unlabeled data using the prediction model 750 does not violate the inherent logic of the health and wellbeing of a subject, the loss function can remain unchanged. As a result, the unlabeled data can have impact on the loss function only when the inherent logic of the health and wellbeing of a subject is violated. By contrast, labeled data can have impact on the loss function regardless of their violation of the inherent logic of the health and wellbeing of a subject. It should be understood that the above example is merely illustrative. The unlabeled data can be utilized in various other ways during the prediction model training stage 710. For instance, the unlabeled data can be utilized as training samples 755, for example, to include unsupervised losses such as smoothness of the prediction, as well as for enforcing the inherent logic of the health and wellbeing of a subject. In this way, an unlabeled data can have a corresponding term in the loss function even if its predicted phase does not violate the inherent logic of the health and wellbeing of a subject.

Similarly, auxiliary information can be utilized during the training of identity and activity predication models 750. Preparing training samples 755 can involve manually labelling the input data for the types of activities to be identified. It is challenging and laborious to label every single occurrence of a subject's presence, identity, or activity in the data. For example, a subject rolling over in bed can last anywhere from a few seconds to a few minutes at once, and may occur multiple times throughout a night or monitoring session. The training mechanism described herein allows a developer or end user to label a manageable number of occurrences of these types of actions and mark the rest as "unknown." During training of the prediction models 750, the "unknown" labels are not used and excluded as part of the training loss function for these specific labels. This can prevent the unlabeled data from being treated as negative examples, e.g. target activities being identified as absent from the input video frames, though these "unknown" labels may later be determined by providing the data to a trained model for analysis. Alternatively, or additionally, selected sets of positive examples and negative examples can be generated and the model can be fine-tuned using these positive and negative examples.

In addition, the training mechanisms described herein also allow hierarchical or multiple labeling. Multiple subjects and multiple activities can overlap, and one activity can contain multiple activities. As a result, multiple labels can be marked for the same data set. For example, multiple IoT devices may detect the presence of multiple RFID tags and multiple activities can appear in the same set of data. As such, multiple subjects or activities can happen concurrently in the same set of data, with possible accompanying events. By allowing multiple labels in a given set of data, potential knowledge contained in a training set of data can be fully exploited by the content data analysis system 700 to train the prediction models 750.

Although the training mechanisms described herein mainly focus on training a prediction model 750. These training mechanisms can also be utilized to fine tune existing prediction models 750 trained from other datasets. For example, in some cases, a prediction model 750 might have been pre-trained using non-subject monitoring data. In those cases, the prediction models 750 can be retrained using the training samples 755 containing subject monitoring data and other auxiliary information as discussed herein.

The prediction model training stage 710 outputs trained prediction models 750 including the trained subject and/or device identification model 765, the activity identification model 770, the health and wellbeing determination model 775, the personnel management model 780, the inventory control model 785, and the optimization model 787. The trained subject and/or device identification model 765 may be used in the subject and/or device identification prediction stage 715 to generate subject or device identification predictions for input data 705. The trained activity identification models 770 may be used in the activity identification stage 720 to identify activity of one or more identified subjects or devices from the input data 705 in combination with the subject or device identification predictions. Measurements can be determined for the identified subjects, devices, and/or activity using the measurement determination stage 725. The determined measurements may be validated in accordance with known or logical measurements for one or more identified subjects, device, or activities in the validation stage 730. The trained health and wellbeing determination model 775 may be used in the health and wellbeing determination stage 735 in combination with measurements from the measurement determination stage 725 (and optional validation stage 730) to predict or determine the health and wellbeing 790 for identified one or more subjects, device, and/or activities identified in the content data 705 in accordance with the subject and activity identification stages 715/720.

The trained personnel management model 780 may be used in the personnel management stage 740 in combination with input data 705 and the results of other stages, for example, the health and wellbeing stage 735 to predict personnel management requirements 795. For example, peak time requirements for nursing assistants may be determined to optimize staffing ratios to accommodate peak wet events. The inventory control model 785 may be used in the inventory control stage 780 in combination with input data 705 and the results of other stages, for example, the activity identification stage 720 to predict inventory requirements 797. For example, analytics from sensor and IoT device data relating to cumulative wetting events within a facility can be used for logistics purposes for management of undergarment or absorbent pad inventory, including direct ordering through commercial partners. The optimization model 787 may be used in the optimization stage 780 in combination with input data 705 and the results of other stages, for example, measurement stage 725 and the health and wellbeing determination stage 735 to predict optimal conditions. For example, analytics from sensor and IoT device data can be used to determine best practices for an acceptable period for changing undergarment or absorbent pad by the personnel. Clinical endpoints which could be used for optimization as targets to mitigate may include the rate of urinary tract infection, rate of decubiti, fall rate, and patient satisfaction.

Figure 8:
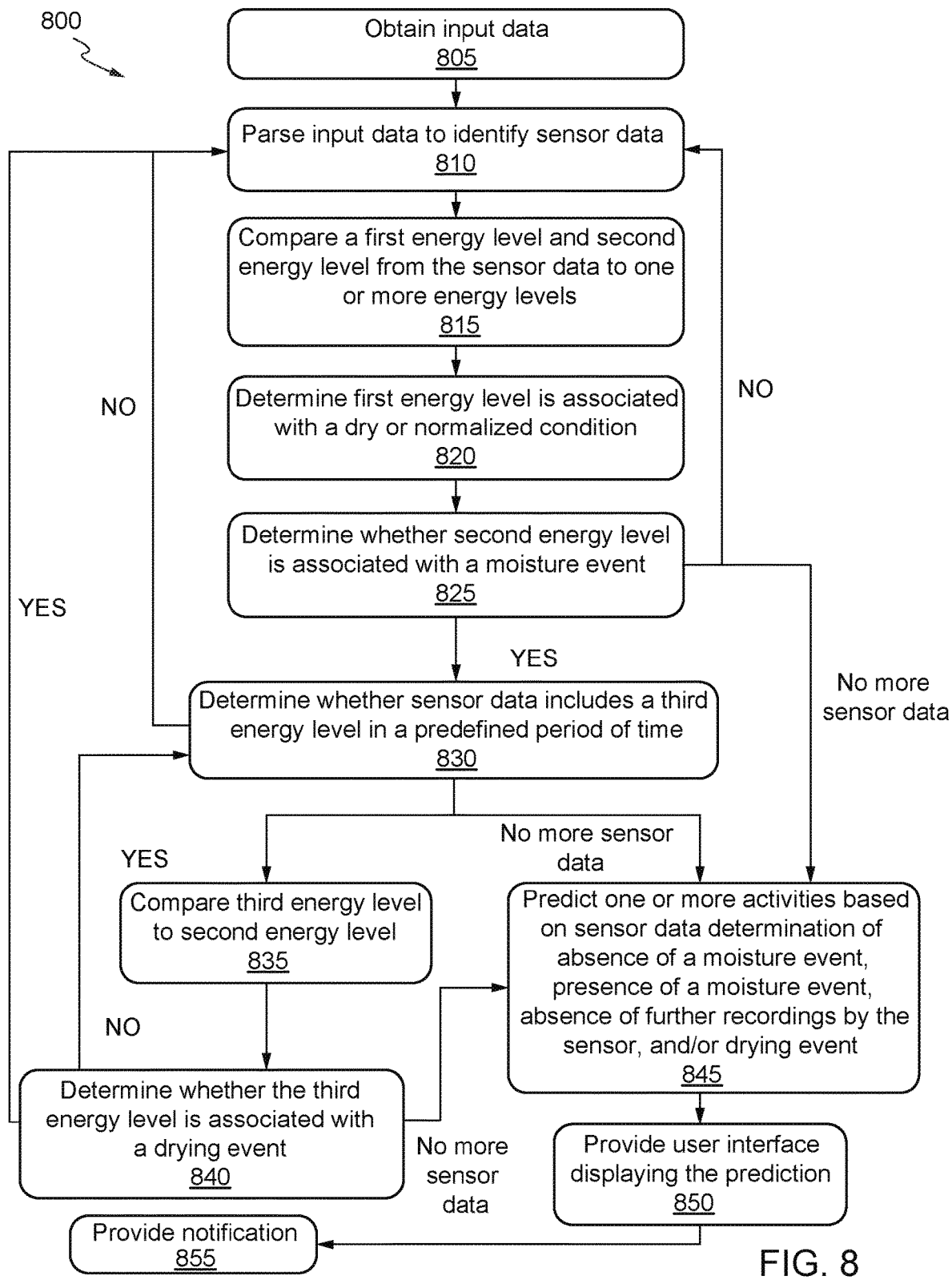
FIG. 8 shows a flowchart illustrating a process for determining a moisture sensing event and predicting activity of an identified subject in accordance with some embodiments.

FIG. 8A illustrates a method 800 for determining a moisture sensing event and predicting activity of an identified subject. At step 805, input data is obtained. For example, data is obtained from an IoT device, as discussed with respect to FIGS. 1, 2, 3A-3E, 4A-4C, 5A-5F, and 6A-6E. At step 810, the input data is parsed to identify all sensor data collected by the IoT device from a sensor associated with a subject over a window of time. The sensor data from the sensor includes a first energy level obtained at a first time and a second energy level obtained at a second time that is after or later than the first time. The parsing may including grouping all the sensor data from the sensor over the window of time based on a unique identifier associated with the sensor. The unique identifier may be provided as metadata associated with the sensor data by the sensor. At step 815, the first energy level and the second energy level are compared to a table of one or more energy levels associated with dry or normalized conditions for the environment in which the sensor is deployed. At step 820, a determination is made based on the comparison that the first energy level matches the one or more energy levels associated with dry or normalized conditions for the environment. As used herein, when an action is "based on" something, this means the action is based at least in part on at least a part of the something.

At step 825, a determination is made based on the comparison that the second energy level does not match the one or more energy levels associated with dry or normalized conditions for the environment. In response, to determining the second energy level does not match the one or more energy levels associated with dry or normalized conditions, determining whether a change between the first energy level and the second energy level exceeds a predetermined energy threshold associated with a moisture event or whether the second energy level exceeds a predetermined energy threshold associated with a moisture event. When the predetermined energy threshold is exceeded by the change between the first energy level and the second energy level or the predetermined energy threshold is exceeded by the second energy level, the moisture event is identified for the subject associated with the sensor and processing continues at step 830. When the predetermined energy threshold is not exceeded by the change between the first energy level and the second energy level or the predetermined energy threshold is not exceeded by the second energy level, it is determined that a moisture event has not occurred for the subject associated with the sensor and processing continues at step 810 for remaining sensor data; and alternatively continues at step 845 if there is no remaining sensor data.

At step 830, a determination is made as to whether the sensor data from the sensor includes a third energy level (same or different energy level from the first and second energy levels, but identified as a separate recording of an energy level as compared to the recording for the first and second energy levels) for processing that was collected by the IoT device within a predefined period of time after the second time. In some embodiments, the predefined period of time is 3 minutes, 5 minutes, 10 minutes, 15 minutes, or 30 minutes. When the sensor data from the sensor includes the third energy level for processing, processing continues at step 835. When the sensor data from the sensor does not include a third energy level for processing, processing continues at step 845.

At step 835 the third energy level is compared to the second energy level. At step 840, a determination is made based on the comparison that the third energy level does not match the second energy level. In response, to determining the third energy level does not match the second energy level, determining whether a change between the second energy level and the third energy level exceeds a predetermined drying threshold associated with a drying event or whether the third energy level exceeds a predetermined drying threshold associated with a drying event. When the predetermined drying threshold is not exceeded by the change between the second energy level and the third energy level or the predetermined drying threshold is not exceeded by the third energy level, a continuation of the moisture event is identified for the subject associated with the sensor and processing continues at step 830 for remaining sensor data looking for fourth, fifth, sixth, etc. energy levels within the predefined period; and alternatively continues at step 845 if there is no remaining sensor data within the predefined period. When the predetermined drying threshold is exceeded by the change between the second energy level and the third energy level or the predetermined drying threshold is exceeded by the third energy level, it is determined that a drying event has occurred for the subject associated with the sensor and processing continues at step 810 for remaining sensor data; and alternatively continues at step 845 if there is no remaining sensor data.

At step 845, one or more of: (1) a nonevent, (2) an incontinence event, (3) a saturated undergarment or absorption pad, and (4) an unsaturated undergarment or absorption pad is determined based on the logic results from steps 815-840. The logic of steps 815-840 being determination of absence of a moisture event, presence of a moisture event, absence of further recordings by the sensor, and/or presence of a drying event. In some instances (e.g., in instance where there are complex energy level patterns with more than two or three energy levels), the one or more of: (1) a nonevent, (2) an incontinence event, (3) a saturated undergarment or absorption pad, and (4) an unsaturated undergarment or absorption pad is determined by a prediction model (e.g., trained activity identification models 770 used in the activity identification stage 720 described with respect to FIG. 7) based on the sensor data and the pattern of logic results from steps 815-840. At step 850, a user interface is provided displaying information concerning one or more of the following activities: (1) a nonevent, (2) an incontinence event, (3) a saturated undergarment or absorption pad, and (4) an unsaturated undergarment or absorption pad as part of a service of a management program. At step 855, a notification may be provided to an end user as a result of the determined activity as an additional part of a service of the management program.

In some instances, a nonevent may be determined by logic or the prediction model when the first energy level is associated with the dry or normalized condition based on the comparison and the second energy level is not associated with a moisture event based on the comparison. In some instances, an incontinence event may be determined by logic or the prediction model when the first energy level is associated with the dry or normalized condition based on the comparison and the second energy level is associated with a moisture event based on the comparison. In some instances, a saturated undergarment or absorption pad may be determined by logic or the prediction model when the first energy level is associated with the dry or normalized condition based on the comparison, the second energy level is associated with a moisture event based on the comparison, and the sensor data does not include a third energy level within a predefined period of time after receipt of the second energy level at the second time. In some instances, a unsaturated undergarment or absorption pad may be determined by logic or the prediction model when the first energy level is associated with the dry or normalized condition based on the comparison, the second energy level is associated with a moisture event based on the comparison, the sensor data does include a third energy level within a predefined period of time after receipt of the second energy level at the second time, and it is determined that a drying event has occurred.

In an exemplary use case, one or more additional predicted models could also be employed to determine best practices for an acceptable period for changing undergarments or absorption pads by the clinical staff based on the predictions made in method 800 and clinical endpoints. Clinical endpoints which could be used for optimization as targets to mitigate may include the rate of urinary tract infection, rate of decubiti, fall rate, and patient satisfaction. Data analytics for use of an additional RFID sensor worn by the clinical staff, which would be read by the in-room IoT devices, could be used to document clinical staff assisting with a wetting event. This could be used to provide clinical staff tracking and confirmation for changing undergarments or absorption pads by the clinical staff.

Figure 9:
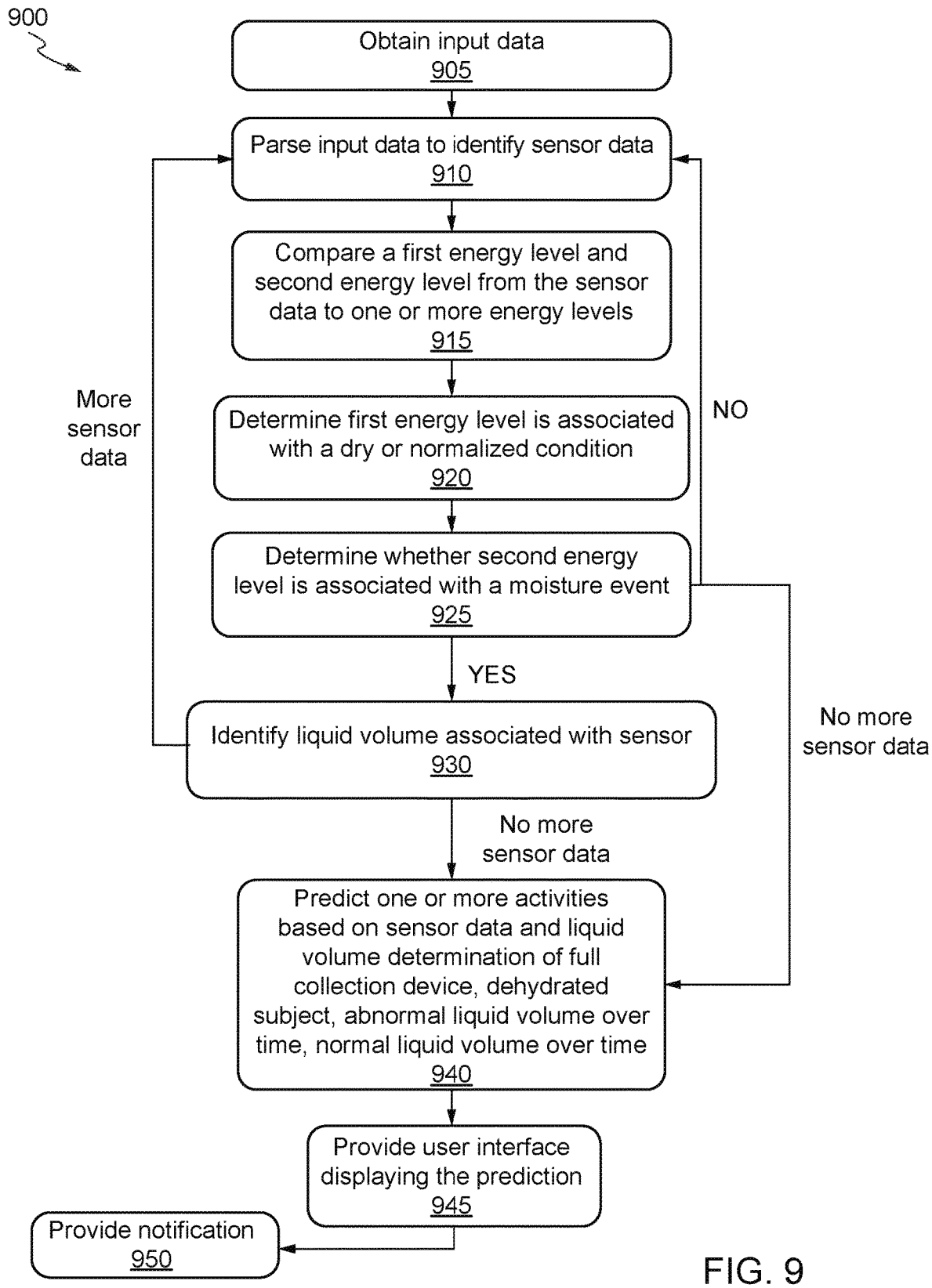
FIG. 9 shows a flowchart illustrating a process for determining a moisture sensing event and predicting activity in accordance with some embodiments.

FIG. 9 illustrates a method 900 for determining a moisture sensing event and predicting activity. At step 905, input data is obtained. For example, data is obtained from an IoT device, as discussed with respect to FIGS. 1, 2, 3A-3E, 4A-4C, 5A-5F, and 6A-6E. At step 910, the input data is parsed to identify all sensor data collected by the IoT device from a plurality of sensors disposed on a collection device (e.g., a Foley bag associated with a subject) over a window of time. The parsing may including grouping the sensor data into subsets of sensor data received from each sensor of the plurality of sensors over the window of time based on a unique identifier associated with each of the sensors. The unique identifier may be provided as metadata associated with the sensor data by the plurality of sensors. At least one subset of sensor data received from a sensor includes a first energy level obtained at a first time and a second energy level obtained at a second time that is after or later than the first time. At step 915, the first energy level and the second energy level are compared to a table of one or more energy levels associated with dry or normalized conditions for the environment in which the plurality of sensors are deployed. At step 920, a determination is made based on the comparison that the first energy level matches the one or more energy levels associated with dry or normalized conditions for the environment.

At step 925, a determination is made based on the comparison that the second energy level does not match the one or more energy levels associated with dry or normalized conditions for the environment. In response, to determining the second energy level does not match the one or more energy levels associated with dry or normalized conditions, determining whether a change between the first energy level and the second energy level exceeds a predetermined energy threshold associated with a moisture event or whether the second energy level exceeds a predetermined energy threshold associated with a moisture event. When the predetermined energy threshold is exceeded by the change between the first energy level and the second energy level or the predetermined energy threshold is exceeded by the second energy level, the moisture event is identified for the sensor associated with the subset of sensor data and processing continues at step 930. When the predetermined energy threshold is not exceeded by the change between the first energy level and the second energy level or the predetermined energy threshold is not exceeded by the second energy level, it is determined that a moisture event has not occurred for the sensor associated with the at least one subset of sensor data and processing continues at step 910 for remaining subsets of sensor data; and alternatively continues at step 935 if there is no remaining sensor data.

At step 930, a liquid volume associated with the sensor that is associated with the at least one subset of sensor data is identified. In some instances, the unique identifier of the sensor identified as recording the moisture event is looked up in a table that provides incremental liquid volumes indexed with the unique identifiers for each sensor of the plurality of sensors. The incremental liquid volumes are associated with each sensor of the plurality of sensors based on location of each sensor on the collection device. Processing continues at step 910 for remaining subsets of sensor data; and alternatively continues at step 935 if there is no remaining sensor data.

At step 935, the liquid volumes identified in step 930 are analyzed to determine a total liquid volume for the collection device. For example, the largest liquid volume identified in step 930 could be determined to be indicative of the total liquid volume for the collection device. Alternatively, a sum of all the liquid volumes identified in step 930 could be determined to be indicative of the total liquid volume for the collection device.

At step 940, one or more of: (1) a full collection device, (2) a dehydrated subject, (3) an abnormal liquid volume over time, and (4) a normal volume over time is determined based on the logic results from steps 915-935. The logic of steps 915-935 being determination of absence of a moisture event, presence of a moisture event, liquid volume associated with each sensor, and total liquid volume for the collection device. In some instances (e.g., in instance where there are complex energy level patterns with more than two or three energy levels), the one or more of: (1) a full collection device, (2) a dehydrated subject, (3) an abnormal liquid volume over time, and (4) a normal volume over time is determined by a prediction model (e.g., trained activity identification models 770 used in the activity identification stage 720 described with respect to FIG. 7) based on the sensor data and the pattern of logic results from steps 915-935. At step 945, a user interface is provided displaying information concerning one or more of the following activities: (1) moisture event, (2) total liquid volume for the collection device, (3) a full collection device, (4) a dehydrated subject, (5) an abnormal liquid volume over time, and (6) a normal volume over time as part of a service of a management program. At step 950, a notification may be provided to an end user as a result of the determined activity as an additional part of a service of the management program.

Figure 10:
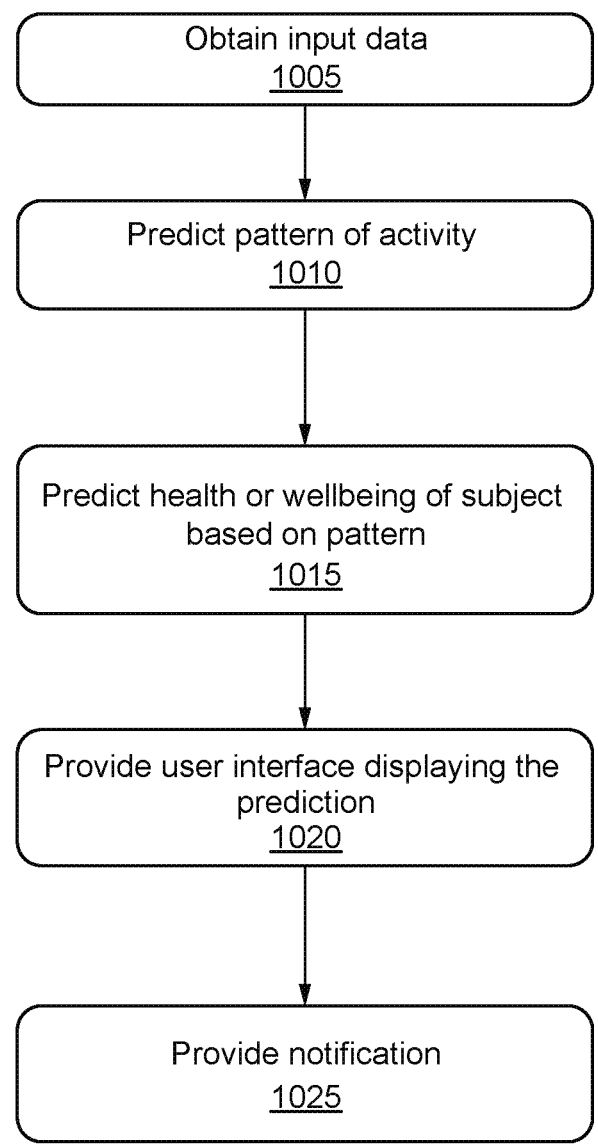
FIG. 10 shows a flowchart illustrating a process for predicting the health or wellbeing of subject in accordance with various embodiments.

FIG. 10 illustrates a method 1000 for predicting the health or wellbeing of subject. At step 1005, input data is obtained. For example, data is obtained from an IoT device, as discussed with respect to FIGS. 1, 2, 3A-3E, 4A-4C, 5A-5F, and 6A-6E. In some instances, the input data also includes prediction(s) made by predictions models. For example, predictions regarding one or more of: (1) a nonevent, (2) an incontinence event, (3) a saturated undergarment or absorption pad, and (4) an unsaturated undergarment or absorption pad as described with respect to FIG. 8 and obtained over a period time for a subject may be used as part of the input data. At step 1010, a pattern of activity (e.g., urination or incontinence events) is identified within the input data by a prediction model (e.g., trained activity identification models 770 used in the activity identification stage 720 described with respect to FIG. 7). At step 1015, features from the pattern of voiding are extracted and used to make a prediction regarding the health or wellbeing of the subject by a prediction model (e.g., trained health or wellbeing prediction models 775 used in the health or wellbeing determination stage 735 described with respect to FIG. 7). At step 1020, a user interface is provided displaying the prediction of the health or wellbeing of the subject as part of a service of a management program based on the predictions by the prediction models. At step 1025, a notification may be provided to an end user as a result of the prediction of the health or wellbeing of the subject as an additional part of a service of the management program.

In an exemplary use case, data analytics for moisture sensing events may employ an process which would identify individuals at risk for early urinary tract infections. For example, normal voiding pattern intervals would be determined for a given patient through historical data. If there is a new change in pattern with the onset of urinary frequency, then notification through an IoT device to the clinical staff of the facility would be provided to obtain a urine analysis and urine culture followed by antibiotic therapy when appropriate. Identification of a new pattern of frequency would be based initially on a set rules such as new onset of two or more voiding intervals in less than 90 minutes. Subsequently, a predictive model approach using training as described with respect to FIG. 7 would be employed. For example, clinically documented episodes of urinary tract infections would be correlated with preceding voiding frequency using RFID sourced data analytics. These patterns could then be used to improve future predictive ability and clinical staff notification.

Figure 11:
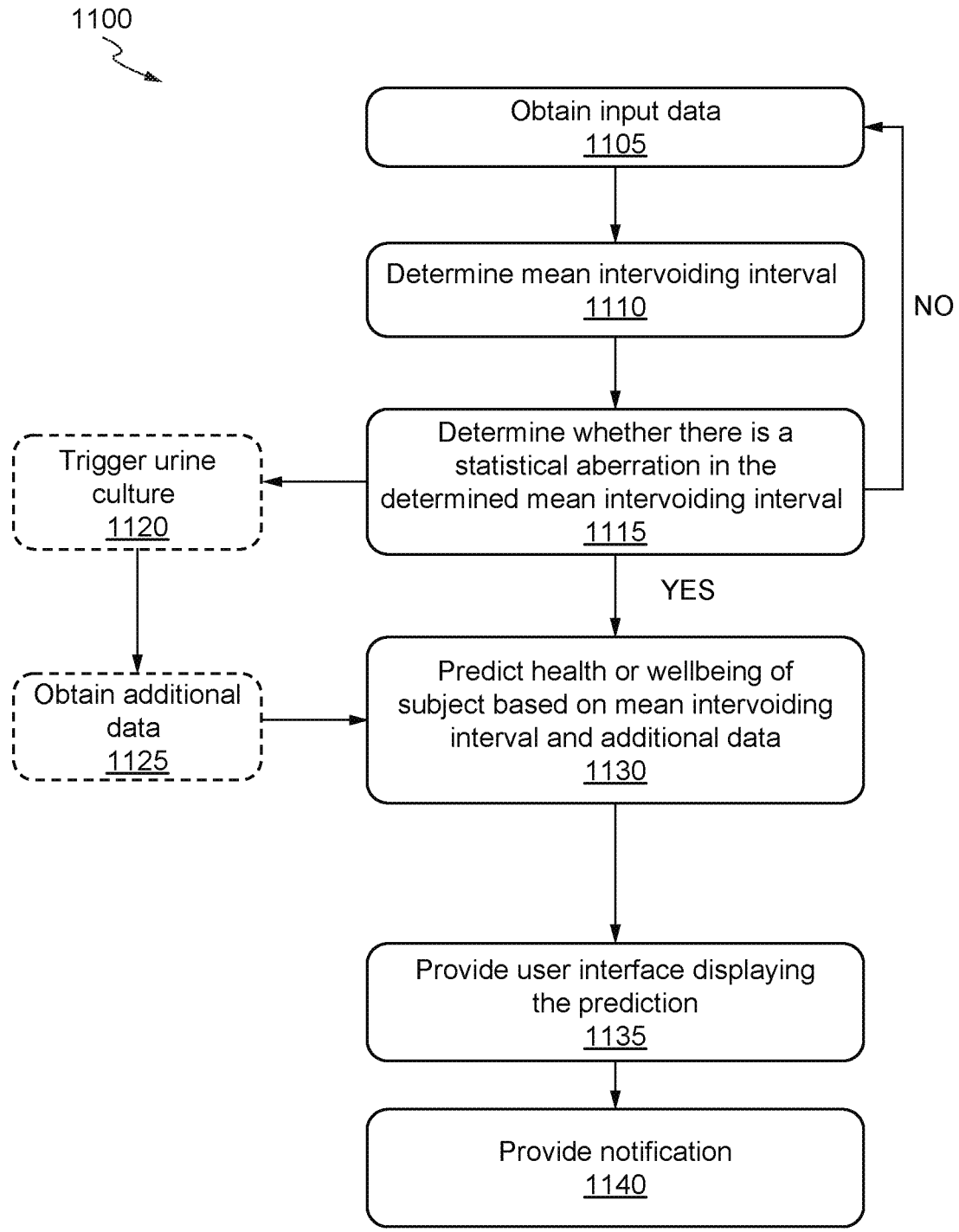
FIG. 11 shows a flowchart illustrating a process for predicting the risk of a subject having or developing a urinary tract infection in accordance with some embodiments.

FIG. 11 illustrates a method 1100 for predicting the risk of a subject having or developing a urinary tract infection. At step 1105, input data is obtained. For example, data is obtained from an IoT device, as discussed with respect to FIGS. 1, 2, 3A-3E, 4A-4C, 5A-5F, and 6A-6E. In some instances, the input data also includes prediction(s) made by predictions models. For example, predictions regarding one or more of: (1) a nonevent, (2) an incontinence event, (3) a saturated undergarment or absorption pad, (4) an unsaturated undergarment or absorption pad, (5) moisture event, (6) total liquid volume for the collection device, (7) a full collection device, (8) a dehydrated subject, (9) an abnormal liquid volume over time, and (10) a normal volume over time as described with respect to FIGS. 8 and 9 and obtained over a period time for a subject may be used as part of the input data. At step 1110, a mean intervoiding interval for the subject is determined over a window of time using the input data. The intervoiding interval is the time between each voiding instance, e.g., time between recognition of a first incontinent event and a second incontinent event by the FID sensors. For example, if a subject's intervoiding interval is between one and four hours over a 5 day interval then the mean intervoiding interval may be determined as 3 hrs (e.g., (2+2+3+3+4+4)/6). At step 1015, a determination is made as to whether there is a statistical aberration in the determined mean intervoiding interval. For example, if a patients mean intervoiding interval is between one and four hours over a 5 day interval, the analytics would look for a statistical aberration from this interval. As an example, a patient with three separate voids within a 1 hour period might trigger a statistical aberration. In some instances, the statistical aberration may be determined based on a standard deviation or clustering algorithm.

At optional step 1115, a notification may be triggered or generated recommending that a urinalysis and urine culture be performed by a laboratory. A user interface dashboard may permit a user to input data entry of the resultant clinical state from the urinalysis and urine culture (infected/not-infected). This data entry be performed either through manual entry or through direct integration of the electronic medical record. The data points may include urinalysis, urine culture or methodologies using direct detection of genetic signatures of infection (PCR analysis, etc.). At optional step 1120, the results of the urinalysis and urine culture and additional data may be obtained for input into one or more prediction models. Additional data inputs which could be used to create a determination of urinary tract infection risk include time interval of meals as well as IV rates and g tube feeds. For example, if a g tube feed occurred at a specific time, the system may anticipate that a voiding interval would ensue after a reduced period of time, avoiding an alarm event. Other parameters that could be evaluated include prolonged intervoiding intervals potentially consistent with dehydration.

At step 1125, features from the input data, the mean intervoiding interval for the subject, and optionally the results of the urinalysis and urine culture and additional data are extracted and used to make a prediction regarding the health or wellbeing of the subject by a prediction model (e.g., trained health or wellbeing prediction models 775 used in the health or wellbeing determination stage 735 described with respect to FIG. 7). In some instances, the prediction regarding the health or wellbeing includes a urinary tract infection risk score indicative of the subject having a urinary tract infection or developing a urinary tract infection. At step 1130, a user interface is provided displaying the prediction of the health or wellbeing of the subject as part of a service of a management program based on the predictions by the prediction models. At step 1135, a notification may be provided to an end user as a result of the prediction of the health or wellbeing of the subject as an additional part of a service of the management program.

Figure 12:
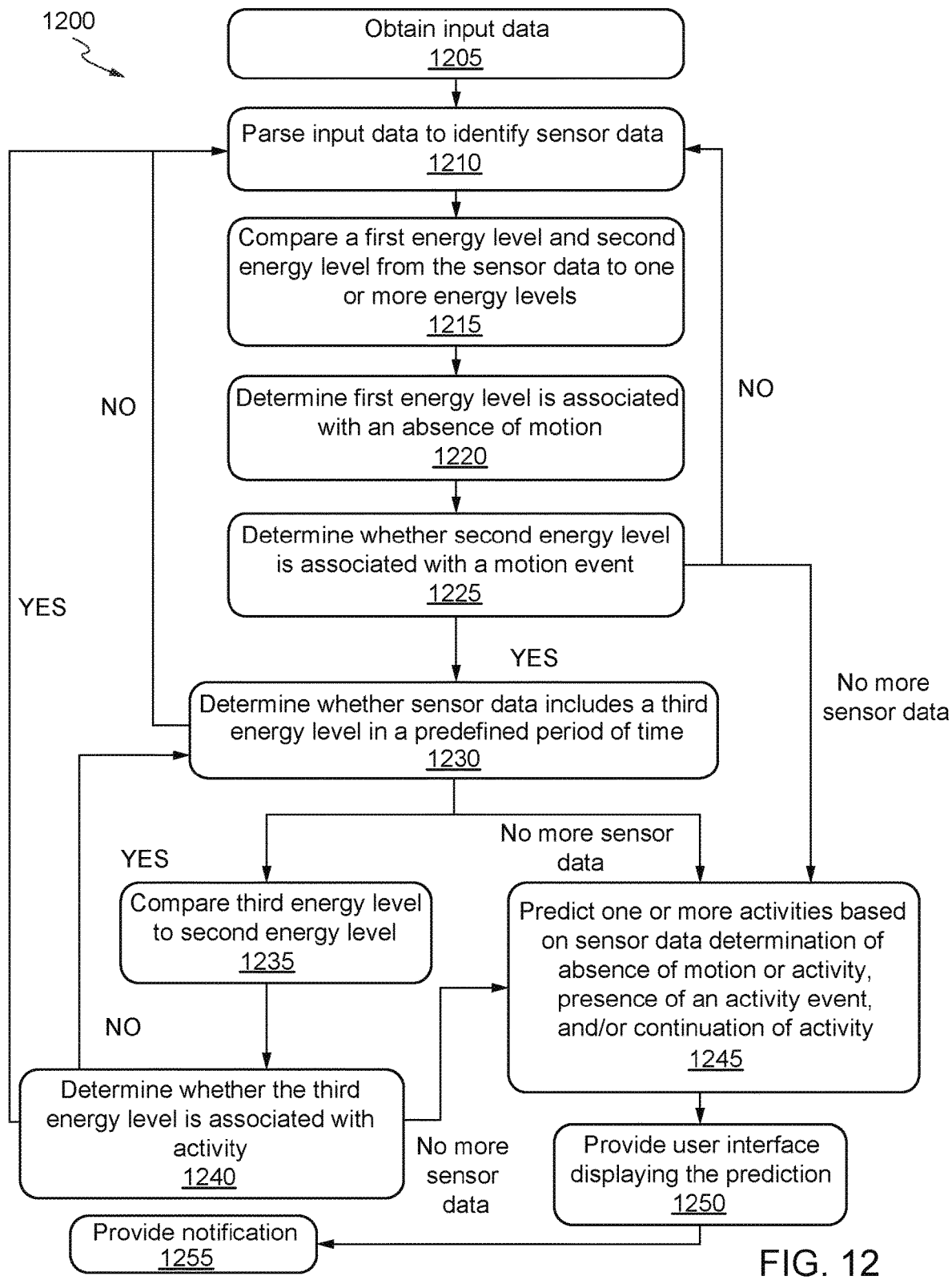
FIG. 12 shows a flowchart illustrating a process for determining a motion event and predicting activity of an identified subject in accordance with various embodiments.

FIG. 12 illustrates a method 1200 for determining a motion event and predicting activity of an identified subject. At step 1205, input data is obtained. For example, data is obtained from an IoT device, as discussed with respect to FIGS. FIGS. 1, 2, 3A-3E, 4A-4C, 5A-5F, and 6A-6E. At step 1210, the input data is parsed to identify all sensor data collected by the IoT device from a sensor associated with a subject over a window of time. The sensor data from the sensor includes a first energy level obtained at a first time and a second energy level determined at a second time that is after the first time. The parsing may including grouping all the sensor data from the sensor over the window of time based on a unique identifier associated with the sensor. The unique identifier may be provided as metadata associated with the sensor data by the sensor. At step 1215, the first energy level and the second energy level are compared to a table of one or more energy levels associated with a stationary position within the environment in which the sensor is deployed (i.e., as the sensor moves closer and further away from an IoT device there is a change in energy states; however, the energy levels will obtain equilibrium while stationary). At step 1220, a determination is made based on the comparison that the first energy level matches the one or more energy levels associated with a stationary position within the environment.

At step 1225, a determination is made based on the comparison that the second energy level does not match the one or more energy levels associated with a stationary position within the environment. In response, to determining the second energy level does not match the one or more energy levels associated with a stationary position within the environment, determining whether a change between the first energy level and the second energy level exceeds a predetermined energy threshold associated with a motion event or whether the second energy level exceeds a predetermined energy threshold associated with a motion event. When the predetermined energy threshold is exceeded by the change between the first energy level and the second energy level or the predetermined energy threshold is exceeded by the second energy level, the motion event is identified for the subject associated with the sensor and processing continues at step 1230. When the predetermined energy threshold is not exceeded by the change between the first energy level and the second energy level or the predetermined energy threshold is not exceeded by the second energy level, it is determined that a motion event has not occurred for the subject associated with the sensor and processing continues at step 1210 for remaining sensor data; and alternatively continues at step 1245 if there is no remaining sensor data.

At step 1230, a determination is made as to whether the sensor data from the first sensor includes a third energy level (same or different energy level from the first and second energy levels, but identified as a separate recording of an energy level as compared to the recording for the first and second energy levels) for processing that was collected by the IoT device within a predefined period of time after the second time. In some embodiments, the predefined period of time is 3 minutes, 5 minutes, 10 minutes, 15 minutes, or 30 minutes. When the sensor data from the first sensor includes the third energy level for processing, processing continues at step 1235. When the sensor data from the first sensor does not include a third energy level for processing, processing continues at step 1245.

At step 1235 the third energy level is compared to the second energy level. At step 1240, a determination is made based on the comparison that the third energy level does not match the second energy level. In response, to determining the third energy level does not match the second energy level, determining whether a change between the second energy level and the third energy level exceeds a predetermined activity threshold associated with an activity such as rolling over in bed or getting out of bed or whether the third energy level exceeds a predetermined activity threshold associated with an activity. When the predetermined activity threshold is not exceeded by the change between the second energy level and the third energy level or the predetermined activity threshold is not exceeded by the third energy level, an absence of an activity is identified for the subject associated with the sensor and processing continues at step 1230 for remaining sensor data looking for fourth, fifth, sixth, etc. energy levels within the predefined period; and alternatively continues at step 1245 if there is no remaining sensor data within the predefined period. When the predetermined activity threshold is exceeded by the change between the second energy level and the third energy level or the predetermined energy threshold is exceeded by the third energy level, it is determined that a activity event has occurred for the subject associated with the sensor and processing continues at step 1210 for remaining sensor data; and alternatively continues at step 1245 if there is no remaining sensor data.

At step 1245, one or more of: (1) absence of activity, (2) rolling over in bed activity, (3) getting out of bed activity, (4) fallen on the floor activity, and (5) entering the bathroom activity (e.g., trained activity identification models 770 used in the activity identification stage 720 described with respect to FIG. 7) based on the sensor data and the logic results of steps 1215-1240. The logic results of steps 1215-1240 being determination of absence of motion or activity event, presence of a activity event, and/or continued activity event. At step 1250, a user interface is provided displaying one or more of the following activities: (1) absence of activity, (2) rolling over in bed activity, (3) getting out of bed activity, (4) fallen on the floor activity, and (5) entering the bathroom activity. At step 1255, a notification may be provided to an end user as a result of the determined activity as an additional part of a service of the management program.

In an exemplary use case, data analytics for fall risk may employ RFID sensors and one or more IOT device. For example, RFID has an optimal signal range determined by several factors, including the radio frequency, power of the transceiver, and distance between the transceiver and the sensor tag. The range limitation of the transceiver can be utilized to provide a form of geo-fencing which will notify the nursing staff when a patient with an RFID tag present on a undergarment, or as part of a personal identification system, is no longer within the range of a specific transceiver (e.g., IoT device). This information can then be transmitted through the IoT device to the clinical staff to warn of development or movement away from a bed or room. This can also be used as a general principle and does not require the inclusion of wetting analysis. This information can be used to intervene and assist a patient at risk of a fall. This can also be combined with recent notification of a wetting event to increase the confidence of the staff that a patient had a wetting event, has left their bed and is at risk of falling while attempting to ambulate to the bathroom. This will then trigger a central notification for staff to assist.

In another exemplary use case, data analytics for tracking subject movement in bed (e.g., rollover) may employ RFID sensors and one or more IOT device. The use of transceiver RFID sensor phase shifting data or the use of more than one RFID sensors on a subject or a undergarment, including variation in the orientation of the sensors. Variations in signal between the sensors will occur as a subject shifts in bed. This would be used to track subject movement in bed. This data could be used to mitigate bed sore (decubitus) risk. In those subjects falling below a certain threshold of movement, clinical staff could intervene to facilitate rolling or repositioning to minimize pressure sores. Predicted models could be employed with historic movement data in those with and without decubiti to predict safe, normal ranges for subject movement in bed and predictive overall health or wellness of the subject (e.g., at risk for decubitus). Data analytics for use of an additional RFID sensor worn by the clinical staff, which would be read by the in-room IoT devices, could be used to document clinical staff assisting with a fall event or movement of a subject. This could be used to provide clinical staff tracking and confirmation for assist with a fall event or movement to avoid decubitus.

Figure 13:
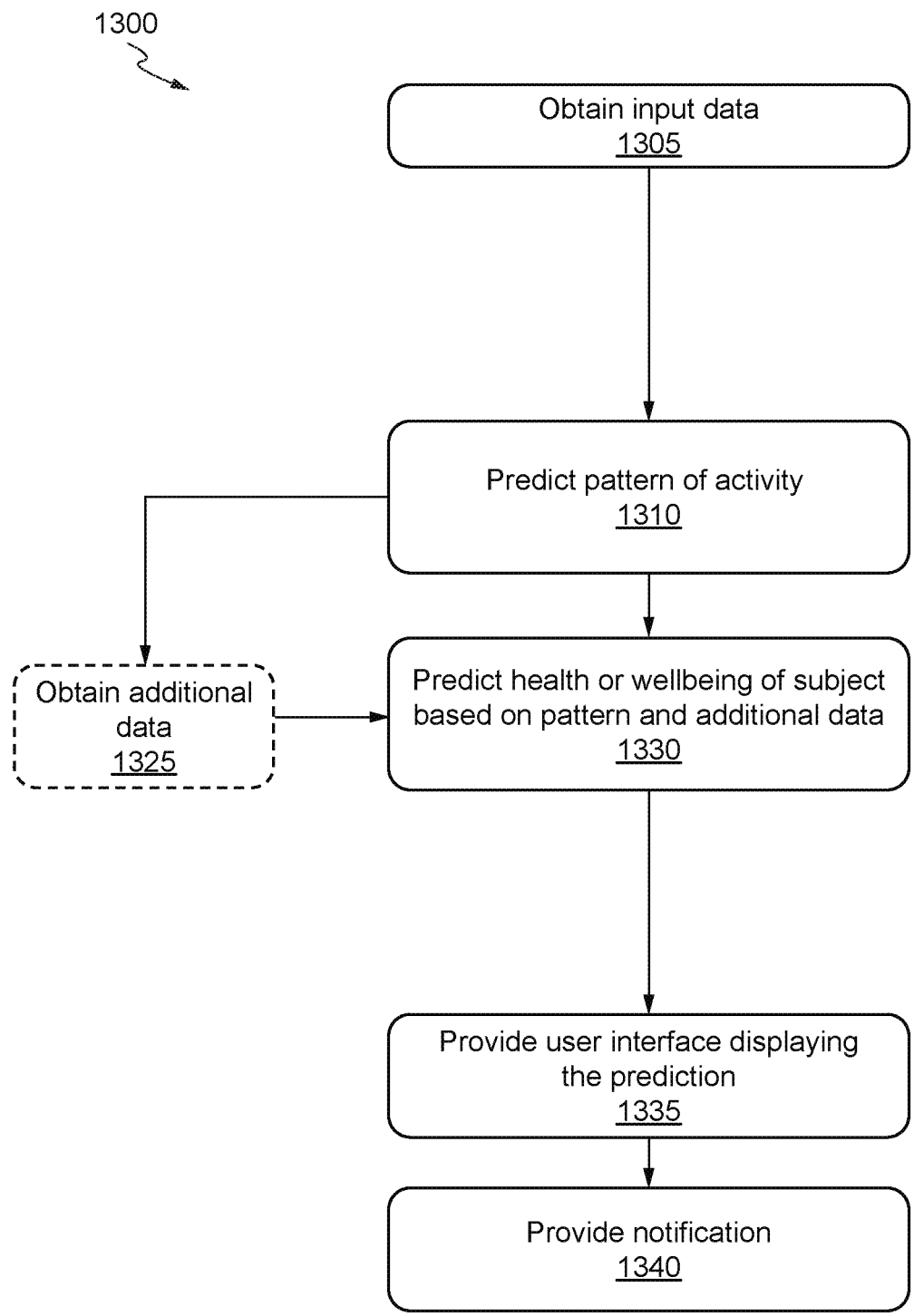
FIG. 13 shows a flowchart illustrating a process for predicting the risk of a subject having or developing decubitus in accordance with various embodiments.

FIG. 13 illustrates a method 1300 for predicting the risk of a subject having or developing decubitus. At step 1305, input data is obtained. For example, data is obtained from an IoT device, as discussed with respect to FIGS. 1, 2, 3A-3E, 4A-4C, 5A-5F, and 6A-6E. In some instances, the input data also includes prediction(s) made by predictions models. For example, predictions regarding one or more of: (1) a non-event, (2) an incontinence event, (3) a saturated undergarment or absorption pad, (4) an unsaturated undergarment or absorption pad, (5) moisture event, (6) total liquid volume for the collection device, (7) a full collection device, (8) a dehydrated subject, (9) an abnormal liquid volume over time, (10) a normal volume over time, (11) absence of activity, (12) rolling over in bed activity, (13) getting out of bed activity, (14) fallen on the floor activity, and (15) entering the bathroom, as described with respect to FIGS. 8, 9, and 12 and obtained over a period time for a subject may be used as part of the input data. At step 1310, a pattern of activity (e.g., urination or incontinence events) may be identified within the input data by a prediction model (e.g., trained activity identification models 770 used in the activity identification stage 720 described with respect to FIG. 7). In some instances, the pattern of activity predicted is one or more of: frequency of urinary incontinence events, duration of incontinent events (duration being how long the subject remained with contaminated undergarment or absorbent pad), mean patient movement in bed over a window of time, frequency of fecal incontinence event, and duration of fecal incontinence event (duration being how long the subject remained with contaminated undergarment or absorbent pad).

At optional step 1315, additional data may be obtained for input into one or more prediction models. Additional data inputs which could be used to create a determination of a decubitus risk include frequency of staff engagement (measured by staff RFID/Bluetooth proximity data). In some instances, the staff engagement may be weighted differently depending on whether incontinence has not occurred indicating patient being turned or repositioned in bed.

At step 1320, features from the activity predicted and optionally the additional data are extracted and used to make a prediction regarding the health or wellbeing of the subject by a prediction model (e.g., trained health or wellbeing prediction models 775 used in the health or wellbeing determination stage 735 described with respect to FIG. 7). In some instances, the prediction regarding the health or wellbeing includes a decubitus risk score indicative of the subject having a urinary tract infection or developing a urinary tract infection. For example, frequency of staff engagement (measured by staff RFID/Bluetooth proximity data) indicating patient being turned or repositioned in bed (could be a feature that reduces the risk score), frequency of urinary incontinence events (more events and more sitting or lying in urine could be a feature that increases the risk score), duration of incontinent events (longer duration for sitting or lying in urine could be a feature that increases the risk score), mean patient movement in bed over a window of time (more movement could be a feature that reduces the risk score), frequency of fecal incontinence event (more events and more sitting or lying in feces could be a feature that increases the risk score), and duration of fecal incontinence event (longer duration for sitting or lying in feces could be a feature that increases the risk score). At step 1330, a user interface is provided displaying the prediction of the health or wellbeing of the subject as part of a service of a management program based on the predictions by the prediction models. At step 1335, a notification may be provided to an end user as a result of the prediction of the health or wellbeing of the subject as an additional part of a service of the management program.

Figure 14:
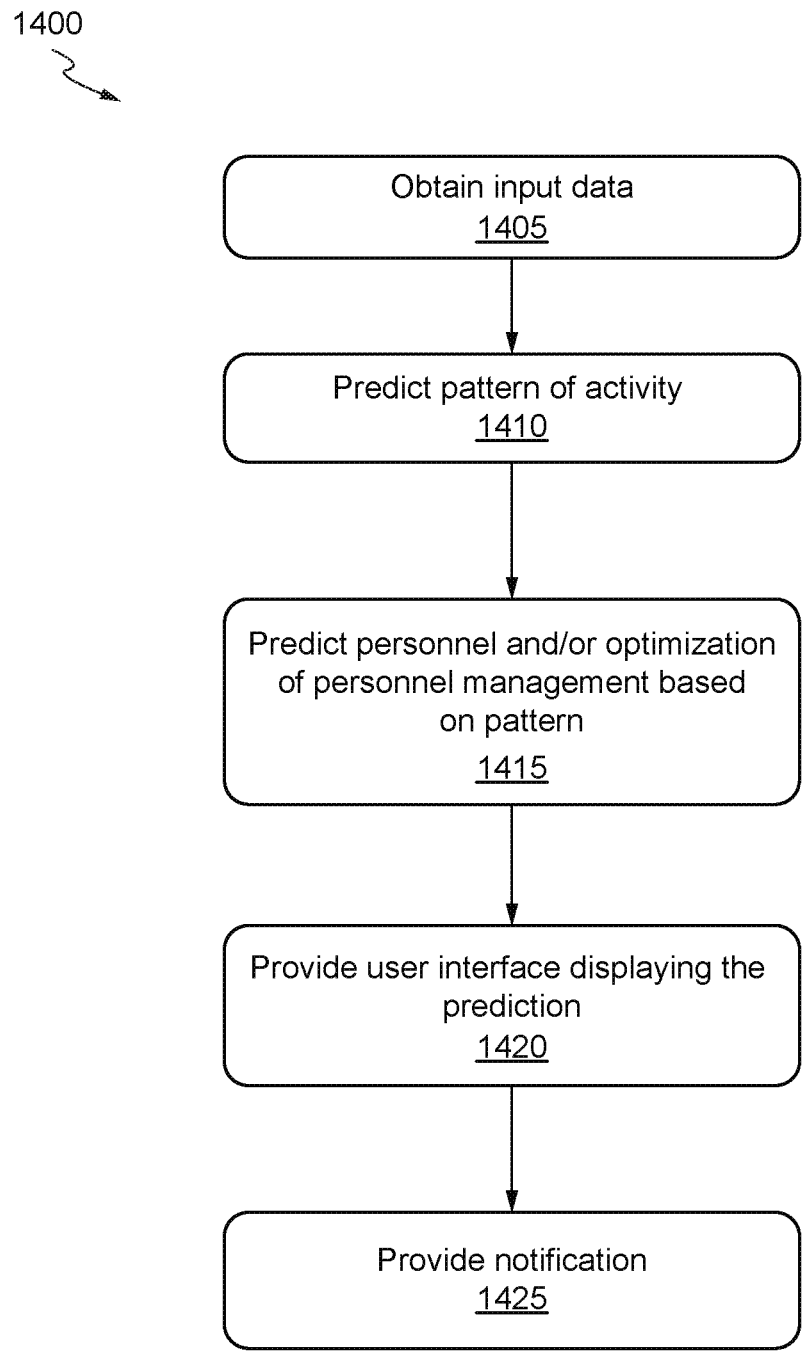
FIG. 14 shows a flowchart illustrating a process for predicting personnel and optimizing personnel management in accordance with various embodiments.

FIG. 14 illustrates a method 1400 for predicting personnel and optimizing personnel management. At step 1405, input data is obtained. For example, data is obtained from an IoT device, as discussed with respect to FIGS. FIGS. 1, 2, 3A-3E, 4A-4C, 5A-5F, and 6A-6E. In some instances, the input data also includes prediction(s) made by predictions models. For example, predictions regarding one or more of: (1) a nonevent, (2) an incontinence event, (3) a saturated undergarment or absorption pad, and (4) an unsaturated undergarment or absorption pad, (5) absence of activity, (6) rolling over in bed activity, (7) getting out of bed activity, (8) fallen on the floor activity, (9) entering the bathroom activity, and (10) the health or wellbeing of subject, as described with respect to FIGS. 8, 9, and 10 and obtained over a period time for one or more subjects may be used as part of the input data. At step 1410, a pattern of activity (e.g., increased activity by subjects including incontinence between 6 am and 9 am) is identified within the input data by a prediction model (e.g., trained activity identification models 770 used in the activity identification stage 720 described with respect to FIG. 7). At step 1415, features from the pattern of activity are extracted and used to make a prediction regarding the personnel and/or optimizing personnel management by a prediction model (e.g., trained personnel management models 780 used in the personnel management stage 740 described with respect to FIG. 7). At step 1420, a user interface is provided displaying the prediction of the personnel and/or optimizing personnel management as part of a service of a management program based on the predictions by the prediction models. At step 1425, a notification may be provided to an end user as a result of the prediction of the personnel and/or optimizing personnel management as an additional part of a service of the management program.

In an exemplary use case, data analytics for moisture sensing events relating to cumulative wetting events within a facility may be used for logistics purposes for personnel management. Peak time requirements for nursing assistants may be determined to optimize staffing ratios to accommodate these events. Data analytics for use of an additional RFID sensor worn by the clinical staff, which would be read by the in-room IoT devices, could be used to document clinical staff assisting with a wetting event. This could be used to provide clinical staff tracking and greater efficiency for logistics purposes for personnel management.

Figure 15:
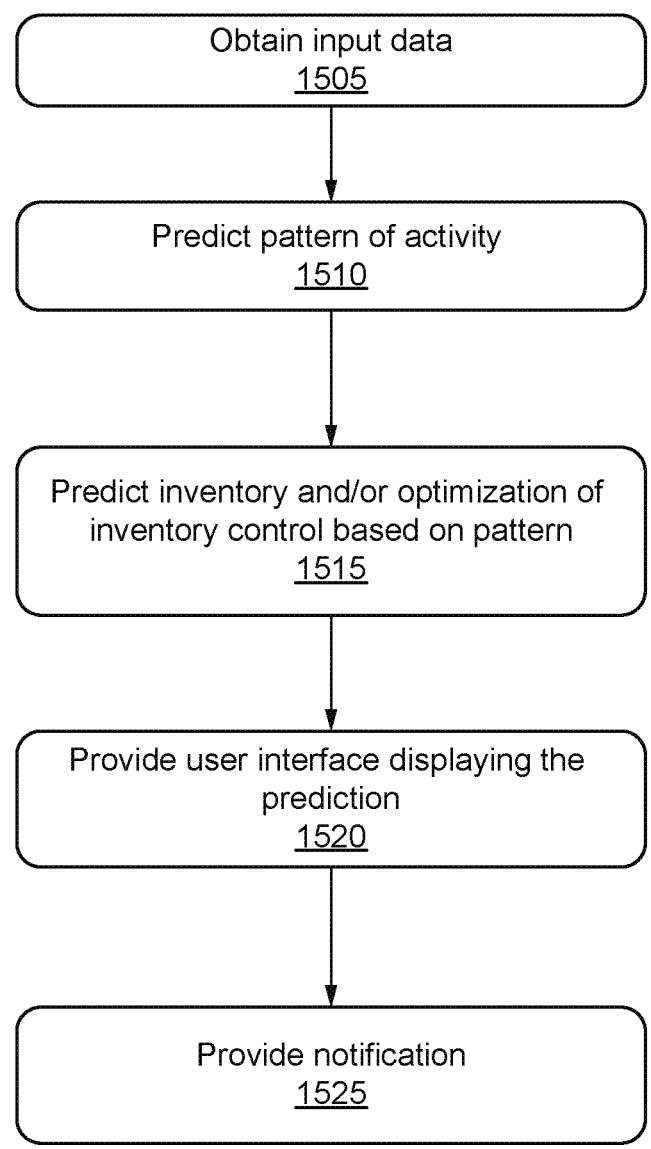
FIG. 15 shows a flowchart illustrating a process for predicting inventory and optimizing inventory control management in accordance with various embodiments.

FIG. 15 illustrates a method 1500 for predicting inventory and optimizing inventory control management. At step 1505, input data is obtained. For example, data is obtained from an IoT device, as discussed with respect to FIGS. FIGS. 1, 2, 3A-3E, 4A-4C, 5A-5F, and 6A-6E. In some instances, the input data also includes prediction(s) made by predictions models. For example, predictions regarding one or more of: (1) a nonevent, (2) an incontinence event, (3) a saturated undergarment or absorption pad, and (4) an unsaturated undergarment or absorption pad, (5) absence of activity, (6) rolling over in bed activity, (7) getting out of bed activity, (8) fallen on the floor activity, (9) entering the bathroom activity, (10) the health or wellbeing of subject, and (11) personnel, as described with respect to FIGS. 8, 9, 10, and 11 and obtained over a period time for one or more subjects may be used as part of the input data. At step 1510, a pattern of activity (e.g., increased use of absorbent pads during the summer) is identified within the input data by a prediction model (e.g., trained activity identification models 770 used in the activity identification stage 720 described with respect to FIG. 7). At step 1515, features from the pattern of activity are extracted and used to make a prediction regarding the inventory and optimizing inventory control management by a prediction model (e.g., trained inventory control models 785 used in the inventory control stage 745 described with respect to FIG. 7). At step 1520, a user interface is provided displaying the prediction of the inventory and optimizing inventory control as part of a service of a management program based on the predictions by the prediction models. At step 1525, a notification may be provided to an end user as a result of the prediction of the inventory and optimizing inventory control as an additional part of a service of the management program.

In an exemplary use case, data analytics for moisture sensing events relating to cumulative wetting events within a facility to be used for logistics purposes for management of undergarment or absorbent pad inventory, including direct ordering through commercial partners. Peak time requirements for undergarments or absorbent pads may be determined to optimize inventory to accommodate these events.

Figure 16:
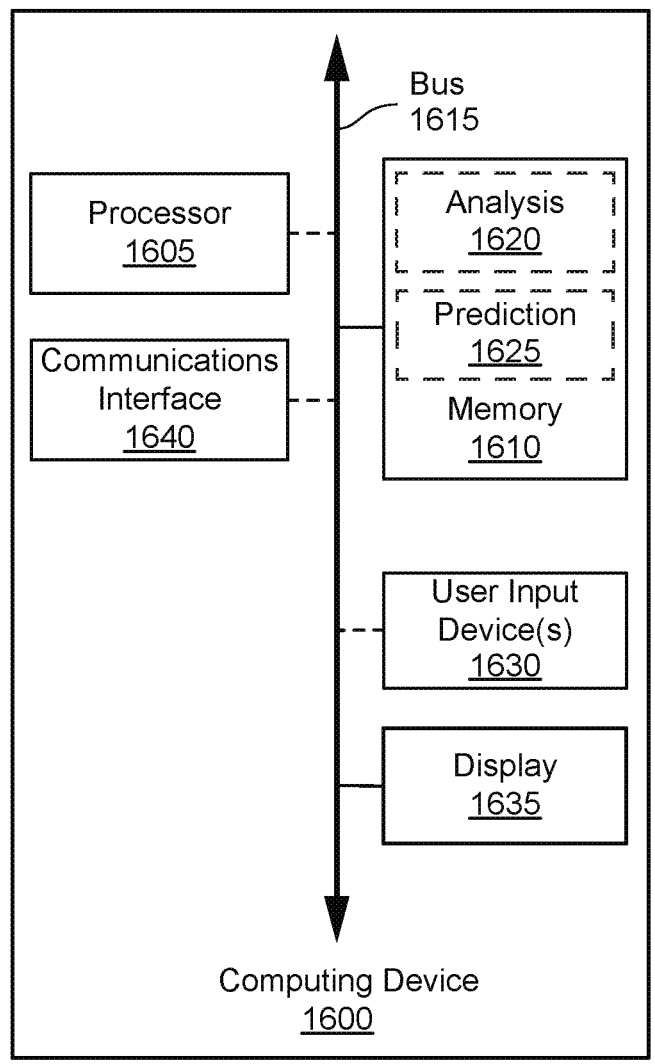
FIG. 16 an exemplary computing device in accordance with various embodiments.

FIG. 16 illustrates an example computing device 1600 (e.g., a client device 105 described with respect to FIG. 1) suitable for use with systems and methods for analyzing and tracking metrics of health and wellbeing of one or more subjects according to this disclosure. The example computing device 1600 includes a processor 1605 which is in communication with the memory 1610 and other components of the computing device 1600 using one or more communications buses 1615. The processor 1605 is configured to execute processor-executable instructions stored in the memory 1610 to perform one or more methods for analyzing and tracking metrics of health and wellbeing of one or more subjects according to different examples, such as part or all of the example method 800 described above with respect to FIG. 8. In this example, the memory 1610 stores processor-executable instructions that provide content data analysis 1620 and metric and optimization prediction 1625, as discussed above with respect to FIGS. 1, 2, 3A-3E, 4A-4C, 5A-5F, 6A-6E, and 8-15. The computing device 1600, in this example, also includes one or more user input devices 1630, such as a keyboard, mouse, touchscreen, microphone, etc., to accept user input. The computing device 1600 also includes a display 1635 to provide visual output to a user such as a user interface.

The computing device 1600 also includes a communications interface 1640. In some examples, the communications interface 1640 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

While some examples of methods and systems herein are described in terms of software executing on various machines, the methods and systems may also be implemented as specifically-configured hardware, such as field-programmable gate array (FPGA) specifically to execute the various methods according to this disclosure. For example, examples can be implemented in digital electronic circuitry, or in computer hardware, firmware, software, or in a combination thereof. In one example, a device may include a processor or processors. The processor comprises a computer-readable medium, such as a random access memory (RAM) coupled to the processor. The processor executes computer-executable program instructions stored in memory, such as executing one or more computer programs. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example one or more non-transitory computer-readable media, that may store processor-executable instructions that, when executed by the processor, can cause the processor to perform methods according to this disclosure as carried out, or assisted, by a processor. Examples of non-transitory computer-readable medium may include, but are not limited to, an electronic, optical, magnetic, or other storage device capable of providing a processor, such as the processor in a web server, with processor-executable instructions. Other examples of non-transitory computer-readable media include, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code to carry out methods (or parts of methods) according to this disclosure.

V. Consolidated User Interfaces

Figure 17:
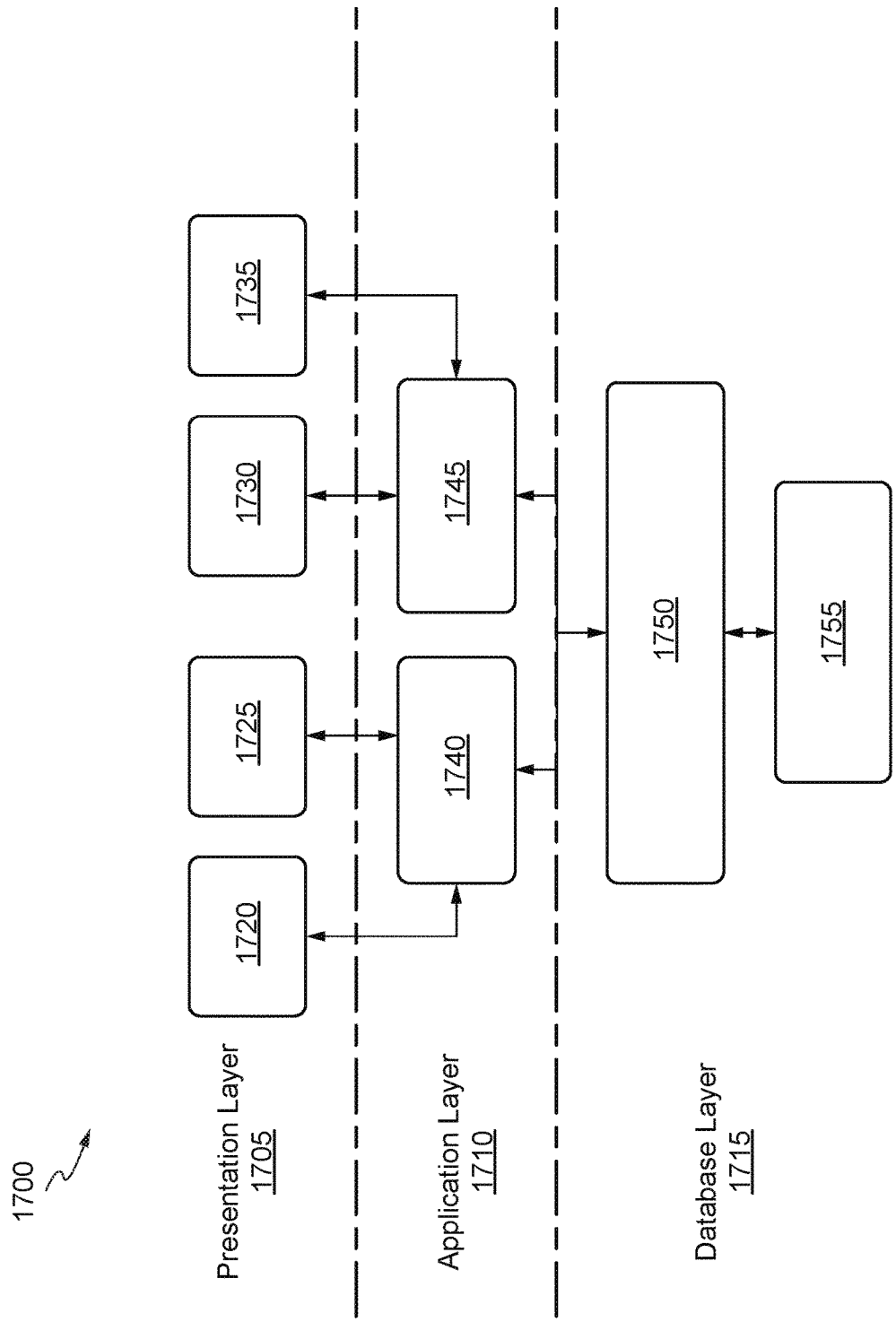
FIG. 17 shows a block diagram illustrating some of the functional components of a IoT solution visualization system in accordance with various embodiments.

FIG. 17 is a block diagram illustrating some of the functional components of a IoT solution visualization system 1700 in accordance with various embodiments. The illustrated system includes three layers: a presentation layer 1705, application layer 1710 and database layer 1715. The presentation layer 1705 includes a plurality of user interfaces (e.g., graphical user interfaces (GUIs)) through which users (e.g., customers or administrators) monitor subject activity using a network of sensors and IoT devices in order to detect activity and events of the subjects in real-time based. These include a plurality of Us 1720, 1725, 1730, and 1735 (e.g., consolidated user interface). In some embodiments, UIs 1720, 1725, 1730, and 1735 reside on one or more workstations or client devices. In other embodiments, UIs 1720, 1725, 1730, and 1735 reside on one or more personal computers. In general, UIs 1720, 1725, 1730, and 1735 can reside on any computational system, and although four UIs are shown in FIG. 17 it should be understood that any number of UIs can be developed and provide in accordance with the aspects described herein.

UIs 1720, 1725, 1730, and 1735 are coupled to one or more application servers 1740 and 1745 (e.g., data analysis module 275 and remote servers 265 as described with respect to FIG. 2) within application layer 1710. Application servers 1740 and 1745 implement the operations to facilitate monitoring and assessment of subject activity in real-time on the underlying communication network, in doing so they communicate and process information between UIs 1720, 1725, 1730, and 1735 and the communication network. In various embodiments, the application servers 1740 and 1745 facilitate monitoring and assessment of subject activity through a set of mechanisms described herein. Application servers 1740 and 1745 may be located at a number of locations in a distributed computing system, including at a computational server or a database server, and may be in communication with any of the UIs in the presentation layer.

Application servers 1740 and 1745 are coupled to database management system 1750 (e.g., data store 270 as described with respect to FIG. 2) within the database layer 1715. Database management system 1750 can be any type of custom-made or commercially available database system for managing storage and retrieval of data. In some embodiments, database management system 1750 includes database servers, and the like. Exemplary database servers include without limitation those commercially available from Oracle, Microsoft, Sybase, IBM and the like. Database management system 1750 is coupled with caches and databases 1755 (e.g., data store 270 as described with respect to FIG. 2). Caches and databases 1755 can be any type of caches or databases which data can be stored and retrieved. This includes, but is not limited to, hierarchical databases and relational databases.

Figures 18A, 18B:
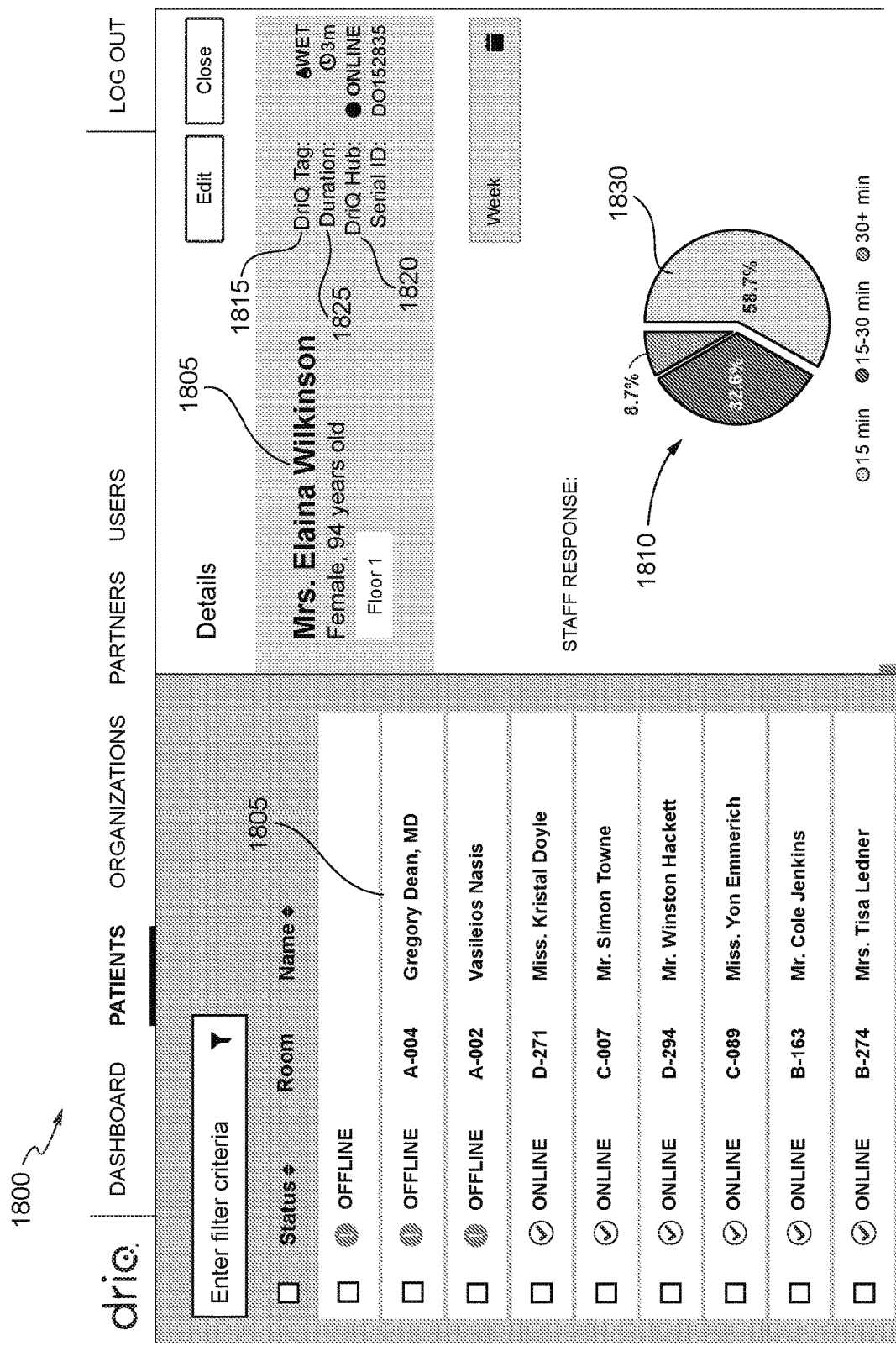
FIGS. 18A and 18B show a consolidated graphic user interface for sensor and IoT device data for various subjects in accordance with various embodiments.

In various embodiments, the presentation layer 1705, application layer 1710 and database layer 1715 operate to provide UIs 1720, 1725, 1730, and 1735, which comprise subject identifiers, raw sensor and IoT device data, determined or predicted activities, device online status, associated trends, and the like. As shown in FIGS. 18A and 18B, some embodiments may provide a consolidated UI 1800 of clinical staff response 1805 for various subjects 1810 based on sensor and IoT device data and temporal data. As discussed herein, sensor and IoT device data and temporal data may be classified or used to make predictions. For example, the data analysis module 275 and data analysis system 700 can dynamically determine incontinence, duration of moisture detection, staff response to incontinence events and predict health or wellbeing of the subject based on a pattern of staff response to incontinence events. This determination of incontinence, duration of moisture detection, determination of staff response to incontinence events, and prediction of health or wellbeing of the subjects can be used by the application layer 1710 to display a dashboard 1702 of consolidated UI 1800 having various information including the current moisture status of a sensor 1815, the online status of a IoT device 1820, the duration of the moisture event 1825, and classification of staff responses 1830 based on time intervals. Some embodiments may also include the predictive models in making the determination for health or wellbeing of the subjects. Furthermore, providing the consolidated UI 1800 of the present status of a sensor and current duration for an event along with associated staff response time as opposed to simply providing data indicating a subject is wet may help clinical staff to focus on identified events and subjects based on their classification and associated response time to improve response time and lower duration of wetness rather than simply informing the clinical staff that a patient is wet.

Figure 19A:
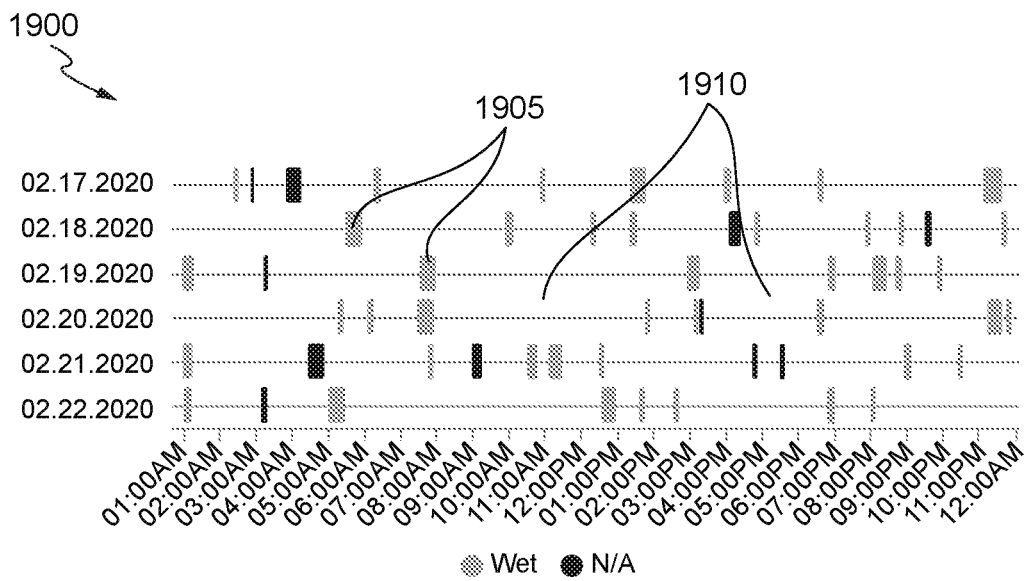
FIGS. 19A and 19B show a consolidated graphic user interface for sensor and IoT device data for a subject in accordance with various embodiments.
Figure 19B:
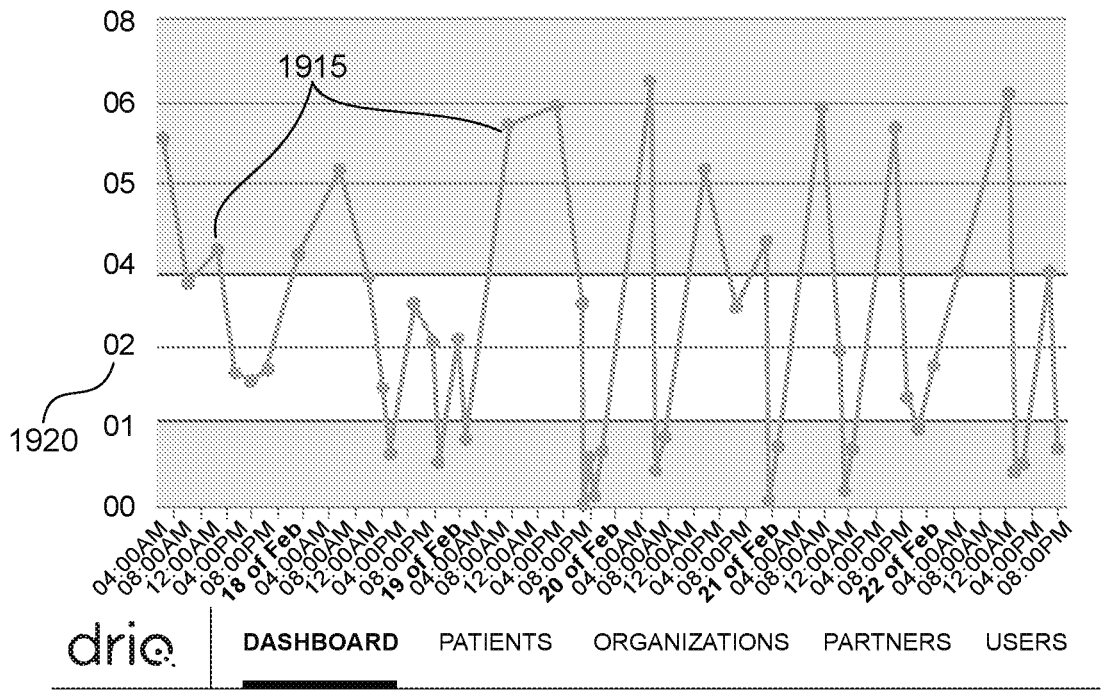

As shown in FIGS. 19A and 19B, some embodiments may provide a consolidated UI 1900 of wetness and voiding intervals for a subject based on sensor and IoT device data and temporal data. As discussed herein, sensor and IoT device data and temporal data may be classified or used to make predictions. For example, the data analysis module 275 and data analysis system 700 can dynamically determine incontinence, duration of moisture detection, and patterns of incontinence events and predict health or wellbeing of the subject based on a pattern of incontinence events. This determination of incontinence, duration of moisture detection, patterns of incontinence events, and prediction of health or wellbeing of the subjects can be used by the application layer 1710 to display a dashboard 1702 of consolidated UI 1900 having various information including the moisture status 1905 of a subject over time versus dry status 1910 of the subject over time, and voiding events 1915 plotted based on time between voids 1920. Some embodiments may also include the predictive models in making the determination for health or wellbeing of the subjects. Furthermore, providing the consolidated UI 1900 of the moisture status and voiding intervals as opposed to simply providing data indicating a subject is wet may help clinical staff to focus on identified subjects based on typical voiding times and frequency of voiding to improve wet time and identification of possible health concerns such as a decrease in voiding interval consistent with a urinary tract infection rather than simply telling the clinical staff that a patient is wet.

Figure 20:
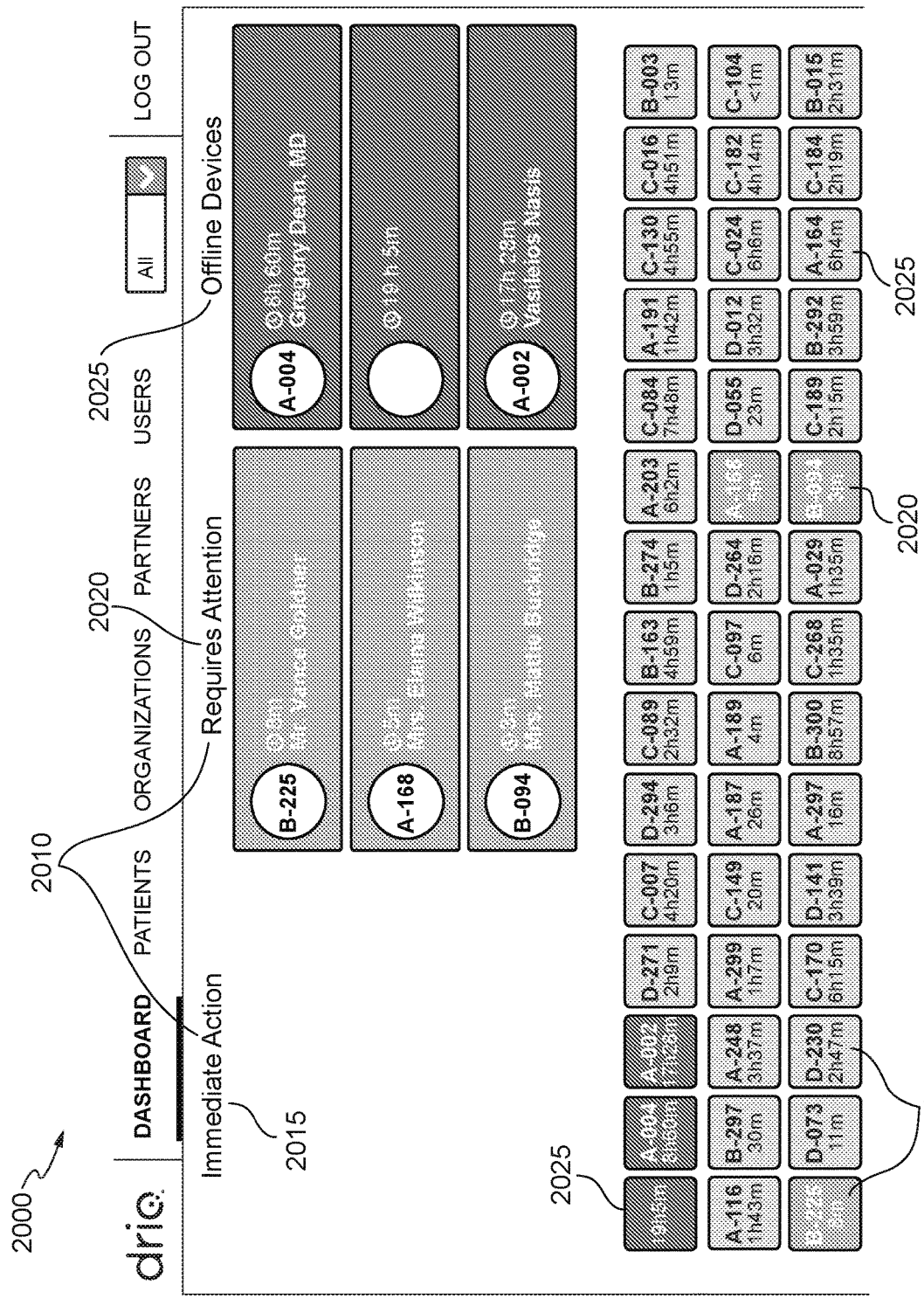
FIG. 20 shows a consolidated graphic user interface for sensor and IoT device data for various subjects in accordance with various embodiments.

As shown in FIG. 20, some embodiments may provide a consolidated UI 2000 of the current status of subjects overlaid with temporal constraints based on sensor and IoT device data and temporal data. As discussed herein, sensor and IoT device data and temporal data may be classified or used to make predictions. For example, the data analysis module 275 and data analysis system 700 can dynamically determine incontinence, duration of moisture detection, and optimal response time for removing a subject from wetness to maintain health and wellbeing and predict health or wellbeing of the subject based on a pattern of incontinence events. This determination of incontinence, duration of moisture detection, optimal response time for removing a subject from wetness, and prediction of health or wellbeing of the subjects can be used by the application layer 1710 to display a dashboard 1702 of consolidated UI 2000 having various information including the moisture status 2005 of multiple subjects overlaid with temporal constraints 2010. For example, a predictive model may determine that the optimal response time for an incontinence event is 15 minutes, and use this predicted time as a threshold to place incontinence events of various subjects into buckets including immediate action required 2015 (>15 min), requires attention 2020 (<15 min), and no action required or offline devices 2025. Some embodiments may also include the predictive models in making the determination for health or wellbeing of the subjects. Furthermore, providing the consolidated UI 2000 of the moisture status with temporal constraints as opposed to simply providing data indicating a subject is wet may help clinical staff to focus on identified events and subjects based on their classification and associated level of action required to improve response time and lower duration of wetness rather than simply informing the clinical staff that a patient is wet.

Figure 21:
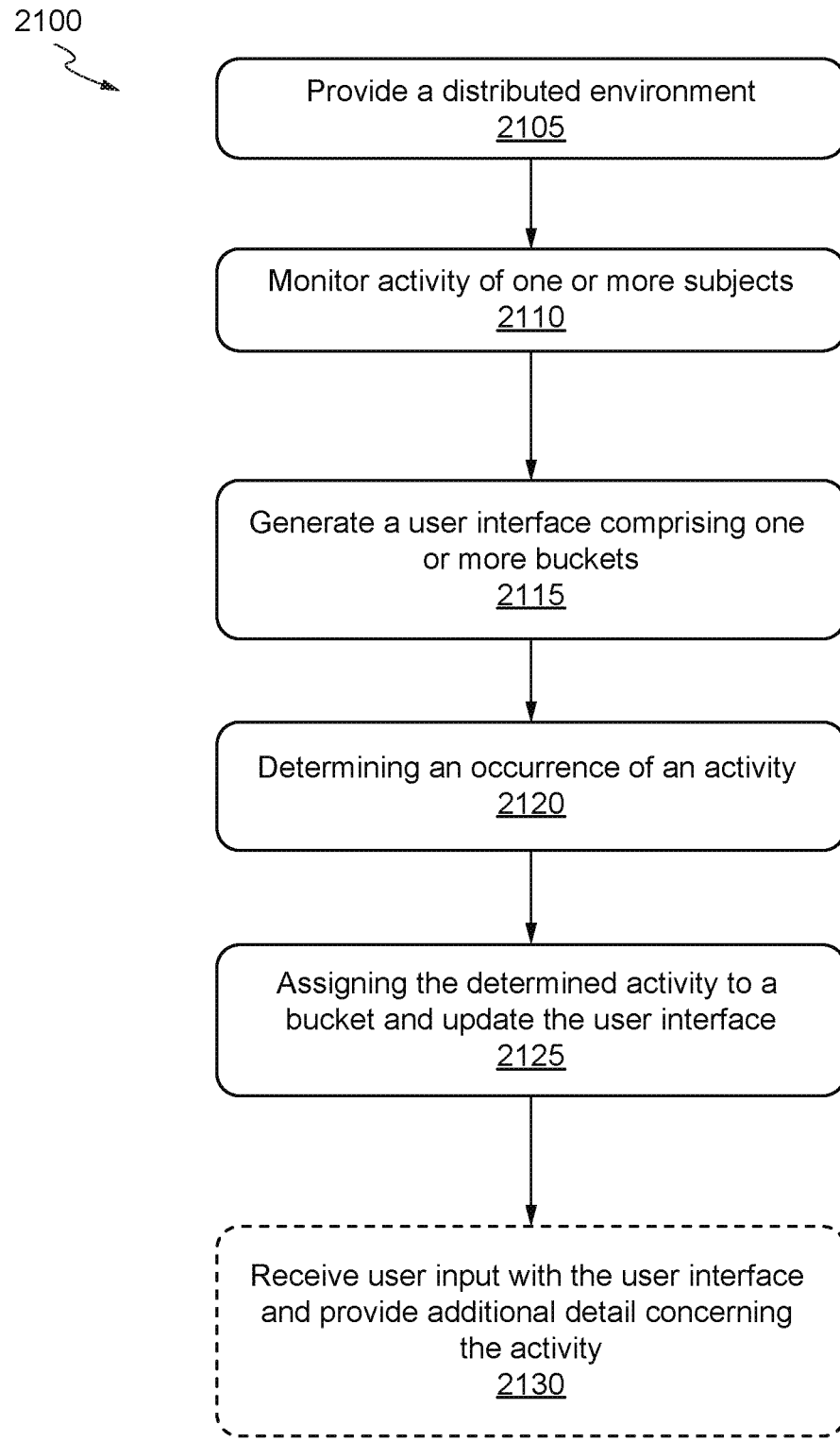
FIG. 21 shows a flowchart illustrating a process for providing a consolidated view of incontinent events for a plurality of subjects in accordance with various embodiments.

FIG. 21 shows a flowchart 21 that illustrates a process for providing a consolidated view of incontinent events for a plurality of subjects. In some embodiments, the processes depicted in flowchart 2100 may be implemented by the management platform 100 discussed with respect to FIG. 1. At step 2105, a distributed environment is provided or instantiated that includes a user device, a plurality of sensors, and one or more IoT devices. In some embodiments, the distributed environment further includes an analytics server and a prediction model component, and trained models created by the analytics server and prediction model component. In certain embodiments, the distributed environment further includes memory for storing the sensor and IoT data received in one or more live information flows and the analysis and prediction results, and historically data.

At step 2110, one or more subjects may be monitored using the plurality of sensors and the one or more IoT devices for activity including incontinence events. At step 2115, a user interface may be provide that includes a plurality of buckets. Each bucket may be associated with an attention level, and each bucket displays the activity including incontinence events presently triggered in real-time. In essence, the buckets are graphical silos of activity classified in accordance with the a scheme defined based on a prediction models prediction of optimal response time to the activity (e.g., incontinence event, fall event, etc.). Providing the consolidated UI of the of activity based on attention level buckets as opposed to simply displaying the activity may help clinical staff to focus on identified events and subjects based on their classification and associated level of action required to improve response time and lower duration of wetness rather than simply informing the clinical staff that a patient is wet.

At step 2120, an occurrence of an activity is determined within the one or more live information flows based on a determination from the analytics server or prediction models. At step 2125, the user interface may be updated to reflect the occurrence of the activity by identifying a bucket from the plurality of buckets that is associated with the attention level required for the activity and assigning the determined activity to the bucket. Optionally, at step 2130, a user input may be received corresponding to a selection of a bucket from the plurality of buckets. In some embodiments, in response to the selection, an expanded UI may be displayed showing detail concerning the activity, e.g., saturation level of the undergarment or absorbent pad.

VI. Additional Considerations

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium", "storage" or "memory" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A method for determining urinary incontinence, comprising:
   electronically determining, by a radio frequency identification (RFID) system, a first energy level that is measured by an RFID sensor disposed on or in an exterior side or nonabsorbent side of a liquid impermeable barrier of an undergarment or absorbent pad worn by a patient based on first energy level data, wherein:

the RFID system comprises (i) an RFID reader comprising a first programmable integrated circuit with a first storage medium and first memory for data storage and processing, and a first data transceiver, and (ii) the RFID sensor;

the RFID sensor comprises a second programed integrated circuit with a second storage medium and second memory for data storage and processing, the RFID sensor does not directly contact moisture or liquid from the undergarment or absorbent pad, and wherein the electronically determining comprises:

electronically transmitting, by the RFID reader at a first time, a first radio frequency (RF) signal to the RFID sensor to cause the RFID sensor to collect the first energy level data in the RFID system;

electronically harvesting or collecting, by the RFID sensor, the first energy level data;

electronically reflecting and/or transmitting, by the RFID sensor, the first RF signal further comprising the first energy level data back to the RFID reader, wherein the reflected first RF signal comprises the first energy level data; and electronically processing, by the RFID system, the reflected first RF signal comprising the first energy level data to determine the first energy level, wherein first energy level corresponds to a change in energy levels proximate to the RFID sensor via energy state changes at the first time, and wherein the first energy level is determined based on an impedance change evaluated by a difference between the first RF signal and the reflected first RF signal;

electronically determining, by the RFID system, that the first energy level is associated with a dry or normalized condition in the undergarment or absorbent pad, based on a comparison between the first RF signal and the reflected first RF signal comprising the first energy level data;

electronically determining, by the RFID system, a second energy level that is measured by the RFID sensor based on second energy level data, wherein the determining comprises:

electronically transmitting, by the RFID reader at a second time that is after the first time, at least one second RF signal to the RFID sensor to cause the RFID sensor to collect the second energy level data in the RFID system;

electronically harvesting or collecting, by the RFID sensor, the second energy level data;

electronically reflecting and/or transmitting, by the RFID sensor, the second RF signal comprising the second energy level data back to the RFID reader, wherein the reflected first RF signal comprises the first energy level data; and electronically processing, by the RFID system, the reflected second RF signal comprising the second energy level data to determine the second energy level, wherein the second energy level corresponds to a change in energy levels proximate to the RFID sensor via energy state changes at the second time, and wherein the second energy level is determined based on an impedance change evaluated by a difference between the at least one second RF signal and the reflected at least one second RF signal;

electronically determining, by the RFID system, that the second energy level associated with a moisture event in the undergarment or absorbent pad is an incontinence event by the patient, based on a comparison between the second RF signal and the reflected second RF signal comprising the second energy level data;

electronically determining, by the RFID system, that the patient has had the incontinence event based on the determining of the first and second energy levels; and electronically generating and transmitting, by the RFID system, a notification to a user interface comprising information concerning the incontinence event associated with the patient.

2. The method of claim 1, wherein the RFID system comprises multiple RFID sensors, each RFID sensor associated with a unique identifier.

3. The method of claim 1, further comprising electronically determining that a change between the first energy level and the second energy level exceeds a predetermined energy threshold associated with the moisture event or the second energy level exceeds a predetermined energy threshold associated with the moisture event, thereby determining the second energy level is associated with the moisture event in the undergarment or absorbent pad.

4. The method of claim 1, wherein the first energy level is a first impedance value and the second energy level is a second impedance value different from the first impedance value.

5. A radio frequency identification (RFID) system comprising:

an RFID sensor disposed on or in an exterior side or nonabsorbent side of a liquid impermeable barrier of an undergarment or absorbent pad worn by a patient, the RFID sensor does not directly contact moisture or liquid from the undergarment or absorbent pad;

an RFID reader comprising a first programmable integrated circuit with a first storage medium and first memory for data storage and processing, and a first data transceiver;

one or more data processors; and a non-transitory computer readable storage medium containing instructions which, when executed on the one or more data processors, cause the one or more data processors, the RFID sensor, or the RFID reader to perform actions including:

electronically determining a first energy level that is measured by the RFID sensor based on first energy level data, comprising:

electronically transmitting, by the RFID reader at a first time, a first radio frequency (RF) signal to the RFID sensor to cause the RFID sensor to collect the first energy level data in the RFID system;

electronically harvesting or collecting, by the RFID sensor, the first energy level data;

electronically reflecting and/or transmitting, by the RFID sensor, the first RF signal further comprising the first energy level data back to the RFID reader, wherein the reflected first RF signal comprises the first energy level data; and electronically processing the reflected first RF signal comprising the first energy level data to determine the first energy level, wherein first energy level corresponds to a change in energy levels proximate to the RFID sensor via energy state changes at the first time, and wherein the first energy level is determined based on an impedance change evaluated by a difference between the first RF signal and the reflected first RF signal;

electronically determining, that the first energy level is associated with a dry or normalized condition in the undergarment or absorbent pad, based on a comparison between the first RF signal and the reflected first RF signal comprising the first energy level data;

electronically determining, by the RFID system, a second energy level that is measured by the RFID sensor based on second energy level data, comprising:

electronically transmitting, by the RFID reader at a second time that is after the first time, at least one second RF signal to the RFID sensor to cause the RFID sensor to collect the second energy level data in the RFID system;

electronically harvesting or collecting, by the RFID sensor, the second energy level data;

electronically reflecting and/or transmitting, by the RFID sensor, the second RF signal comprising the second energy level data back to the RFID reader wherein the reflected first RF signal comprises the first energy level data; and electronically processing the reflected second RF signal comprising the second energy level data to determine the second energy level, wherein the second energy level corresponds to a change in energy levels proximate to the RFID sensor via energy state changes at the second time, and wherein the second energy level is determined based on an impedance change evaluated by a difference between the at least one second RF signal and the reflected at least one second RF signal;

electronically determining that the second energy level associated with a moisture event in the undergarment or absorbent pad is an incontinence event by the patient, based on a comparison between the second RF signal and the reflected second RF signal comprising the second energy level data;

electronically determining that the patient has had the incontinence event based on the determining of the first and second energy levels; and electronically generating and transmitting a notification to a user interface comprising information concerning the incontinence event associated with the patient.

6. The system of claim 5, further comprising the undergarment or absorbent pad, wherein the undergarment or absorbent pad comprises:
a liquid permeable top sheet;
an absorbent material disposed under the liquid permeable top sheet;
a nonabsorbent material disposed adjacent to at least a portion of the liquid permeable top sheet or the absorbent material;
a liquid impermeable back sheet disposed over the absorbent material such that the absorbent material is disposed between the liquid permeable top sheet and the liquid impermeable back sheet; and
an attachment structure attached to the liquid impermeable back sheet, wherein the attachment structure is structured to hold the RFID sensor.

7. The system of claim 6, wherein the attachment structure is a sleeve structure.

8. The system of claim 7, wherein the attachment structure is attached to the liquid impermeable back sheet on an anterior side of the liquid impermeable back sheet over an interface between the underlying absorbent material and the nonabsorbent material.

9. The system of claim 6, wherein the actions further include electronically determining that a change between the first energy level and the second energy level exceeds a predetermined energy threshold associated with the moisture event or the second energy level exceeds a predetermined energy threshold associated with the moisture event, thereby determining the second energy level is associated with the moisture event in the undergarment or absorbent pad.

10. The system of claim 5, further comprising the undergarment or absorbent pad, wherein the undergarment or absorbent pad comprises:
a liquid permeable top sheet;
an absorbent material disposed under the liquid permeable top sheet;
a nonabsorbent material disposed adjacent to at least a portion of the liquid permeable top sheet or the absorbent material;
a liquid impermeable back sheet disposed over the absorbent material such that the absorbent material is disposed between the liquid permeable top sheet and the liquid impermeable back sheet; and
the RFID sensor attached to the liquid impermeable back sheet.

11. The system of claim 10, wherein the actions further include electronically determining that a change between the first energy level and the second energy level exceeds a predetermined energy threshold associated with the moisture event or the second energy level exceeds a predetermined energy threshold associated with the moisture event, thereby determining the second energy level is associated with the moisture event in the undergarment or absorbent pad.

12. The system of claim 10, wherein the RFID sensor is attached to the liquid impermeable back sheet on an anterior side of the liquid impermeable back sheet over an interface between the underlying absorbent material and the nonabsorbent material.

13. The system of claim 10, wherein the one or more data processors are in wireless communication with the RFID sensor.

14. The system of claim 13, wherein the RFID system comprises multiple RFID sensors, each associated with a unique identifier.

15. The system of claim 6, wherein the RFID system comprises multiple RFID sensors, each associated with a unique identifier.

16. The system of claim 15, wherein each of the multiple RFID sensors is attached to the liquid impermeable back sheet on an anterior side of the liquid impermeable back sheet over an interface between the underlying absorbent material and the nonabsorbent material.

* * * * *